(12) United States Patent
Kenedy et al.

(10) Patent No.: US 8,386,519 B2
(45) Date of Patent: Feb. 26, 2013

(54) PANGENETIC WEB ITEM RECOMMENDATION SYSTEM

(75) Inventors: Andrew Alexander Kenedy, Sugar Land, TX (US); Charles Anthony Eldering, Furlong, PA (US)

(73) Assignee: Expanse Networks, Inc., Furlong, PA (US)

( * ) Notice: Subject to any disclaimer, the term of this patent is extended or adjusted under 35 U.S.C. 154(b) by 816 days.

(21) Appl. No.: 12/346,707

(22) Filed: Dec. 30, 2008

(65) Prior Publication Data

US 2010/0169340 A1 Jul. 1, 2010

(51) Int. Cl.
*G06F 17/30* (2006.01)

(52) U.S. Cl. .......................................................... 707/784

(58) Field of Classification Search ................... 707/609, 707/705, 767, 784; 705/7.29
See application file for complete search history.

(56) References Cited

U.S. PATENT DOCUMENTS

| | | | |
|---|---|---|---|
| 5,301,105 A | 4/1994 | Cummings, Jr. | |
| 5,446,886 A | 8/1995 | Li | |
| 5,551,880 A | 9/1996 | Bonnstetter et al. | |
| 5,649,181 A | 7/1997 | French et al. | |
| 5,660,176 A | 8/1997 | Iliff | |
| 5,752,242 A | 5/1998 | Havens | |
| 5,860,917 A | 1/1999 | Comanor et al. | |
| 6,063,028 A | 5/2000 | Luciano | |
| 6,108,647 A | 8/2000 | Poosala et al. | |
| 6,131,092 A | 10/2000 | Masand | |
| 6,216,134 B1 | 4/2001 | Heckerman et al. | |
| 6,253,203 B1 | 6/2001 | O'Flaherty et al. | |
| 6,266,649 B1 * | 7/2001 | Linden et al. | 705/7.29 |
| 6,269,364 B1 | 7/2001 | Kennedy | |
| 6,285,999 B1 | 9/2001 | Page | |
| 6,303,297 B1 | 10/2001 | Lincoln et al. | |
| 6,321,163 B1 | 11/2001 | Graham et al. | |
| 6,393,399 B1 | 5/2002 | Maslyn et al. | |
| 6,457,001 B1 | 9/2002 | Ishida | |
| 6,493,637 B1 | 12/2002 | Steeg | |
| 6,507,840 B1 | 1/2003 | Ioannidis et al. | |
| 6,519,604 B1 | 2/2003 | Acharya et al. | |
| 6,539,377 B1 | 3/2003 | Culliss | |
| 6,596,488 B2 | 7/2003 | Pfeifer et al. | |

(Continued)

FOREIGN PATENT DOCUMENTS

| | | |
|---|---|---|
| WO | WO02080079 A2 | 10/2002 |
| WO | WO03060652 A2 | 7/2003 |

(Continued)

OTHER PUBLICATIONS

Glaser et al., "Advancing Personalized Health Care through Health Information Technology: An Update from the American Health Information Community's Personalized Health Care Workgroup", Journal of the American Medical Informatics Association, Jul. 2008, pp. 391-396, 15 (4), American Medical Informatics Association, USA.

(Continued)

*Primary Examiner* — Cheryl Lewis

(57) ABSTRACT

Computer based systems, methods, software and databases are presented in which correlations between web item preferences and pangenetic (genetic and epigenetic) attributes of individuals are used for pangenetic based web item recommendation in which a user can request and receive personalized online recommendations of web items that are based on the user's pangenetic makeup. Data masking can be used to maintain privacy of sensitive portions of the pangenetic data.

25 Claims, 18 Drawing Sheets

U.S. PATENT DOCUMENTS

| | | |
|---|---|---|
| 6,601,059 B1 | 7/2003 | Fries |
| 6,629,097 B1 | 9/2003 | Keith |
| 6,629,935 B1 | 10/2003 | Miller et al. |
| 6,640,211 B1 | 10/2003 | Holden |
| 6,687,696 B2 | 2/2004 | Hofmann et al. |
| 6,694,311 B1 | 2/2004 | Smith |
| 6,730,023 B1 | 5/2004 | Dodds |
| 6,738,762 B1 | 5/2004 | Chen et al. |
| 6,799,176 B1 | 9/2004 | Page |
| 6,873,914 B2 | 3/2005 | Winfield |
| 6,912,492 B1 | 6/2005 | Johnson |
| 6,931,326 B1 | 8/2005 | Judson |
| 6,947,174 B1 | 9/2005 | Chen et al. |
| 6,993,532 B1 | 1/2006 | Platt et al. |
| 7,054,758 B2 | 5/2006 | Gill-Garrison |
| 7,069,308 B2 | 6/2006 | Abrams |
| 7,072,794 B2 | 7/2006 | Wittkowski |
| 7,107,155 B2 | 9/2006 | Frudakis |
| 7,127,355 B2 | 10/2006 | Cox |
| 7,162,471 B1 | 1/2007 | Knight |
| 7,271,243 B2 | 9/2007 | Dumas Milne Edwards et al. |
| 7,289,983 B2 | 10/2007 | Best |
| 7,305,348 B1 | 12/2007 | Brown |
| 7,392,175 B2 | 6/2008 | Kawatani |
| 7,406,484 B1 | 7/2008 | Srinivasan et al. |
| 7,426,472 B2 | 9/2008 | Fitzpatrick et al. |
| 7,572,603 B2 | 8/2009 | Small et al. |
| 7,592,910 B2 | 9/2009 | Tuck et al. |
| 7,668,738 B2 | 2/2010 | Wiggins |
| 7,739,247 B2 | 6/2010 | Mount et al. |
| 7,752,215 B2 | 7/2010 | Dettinger et al. |
| 7,769,740 B2 | 8/2010 | Martinez et al. |
| 7,809,716 B2 | 10/2010 | Wang et al. |
| 7,877,398 B2 | 1/2011 | Kroeschel et al. |
| 7,904,511 B2 | 3/2011 | Ryan et al. |
| 7,917,374 B2 | 3/2011 | Walker |
| 8,200,509 B2 * | 6/2012 | Kenedy et al. .................. 705/3 |
| 2001/0000810 A1 | 5/2001 | Alabaster |
| 2002/0010552 A1 | 1/2002 | Rienhoff |
| 2002/0048763 A1 | 4/2002 | Penn et al. |
| 2002/0052761 A1 | 5/2002 | Fey et al. |
| 2002/0064792 A1 | 5/2002 | Lincoln et al. |
| 2002/0095585 A1 | 7/2002 | Scott |
| 2002/0120623 A1 | 8/2002 | Vivier et al. |
| 2002/0126545 A1 | 9/2002 | Warren et al. |
| 2002/0128860 A1 | 9/2002 | Leveque |
| 2002/0133299 A1 | 9/2002 | Jacob |
| 2002/0169793 A1 | 11/2002 | Sweeney |
| 2002/0179097 A1 | 12/2002 | Atkins |
| 2002/0183965 A1 | 12/2002 | Gogolak |
| 2003/0009295 A1 | 1/2003 | Markowitz et al. |
| 2003/0030637 A1 | 2/2003 | Grinstein et al. |
| 2003/0046114 A1 | 3/2003 | Davies |
| 2003/0065241 A1 | 4/2003 | Hohnloser |
| 2003/0115193 A1 | 6/2003 | Okamoto et al. |
| 2003/0130873 A1 | 7/2003 | Nevin |
| 2003/0135488 A1 | 7/2003 | Amir et al. |
| 2003/0154104 A1 | 8/2003 | Koningsberg |
| 2003/0163340 A1 | 8/2003 | Fitzpatrick et al. |
| 2003/0167260 A1 | 9/2003 | Nakamura et al. |
| 2003/0171876 A1 | 9/2003 | Markowitz et al. |
| 2003/0195706 A1 | 10/2003 | Korenberg |
| 2003/0203008 A1 | 10/2003 | Gunasekaran |
| 2003/0212579 A1 | 11/2003 | Brown et al. |
| 2003/0233377 A1 | 12/2003 | Kovac |
| 2004/0006488 A1 | 1/2004 | Fitall et al. |
| 2004/0009495 A1 | 1/2004 | O'Malley et al. |
| 2004/0014097 A1 | 1/2004 | McGlennen et al. |
| 2004/0015337 A1 | 1/2004 | Thomas |
| 2004/0019598 A1 | 1/2004 | Huang |
| 2004/0019688 A1 | 1/2004 | Nickerson et al. |
| 2004/0030697 A1 | 2/2004 | Cochran et al. |
| 2004/0034652 A1 | 2/2004 | Hofmann et al. |
| 2004/0093331 A1 * | 5/2004 | Garner et al. .................. 707/3 |
| 2004/0111410 A1 | 6/2004 | Burgoon et al. |
| 2004/0172287 A1 | 9/2004 | O'Toole et al. |
| 2004/0172313 A1 | 9/2004 | Stein et al. |
| 2004/0175700 A1 | 9/2004 | Gessaman |
| 2004/0193019 A1 | 9/2004 | Wei |
| 2004/0197799 A1 | 10/2004 | Williamson |
| 2004/0219493 A1 | 11/2004 | Phillips |
| 2004/0221855 A1 | 11/2004 | Ashton |
| 2004/0242454 A1 | 12/2004 | Gallant |
| 2004/0243545 A1 | 12/2004 | Boone et al. |
| 2004/0254920 A1 | 12/2004 | Brill et al. |
| 2005/0021240 A1 | 1/2005 | Berlin |
| 2005/0026119 A1 | 2/2005 | Ellis et al. |
| 2005/0032066 A1 | 2/2005 | Heng |
| 2005/0060194 A1 | 3/2005 | Brown |
| 2005/0086260 A1 | 4/2005 | Canright et al. |
| 2005/0090718 A1 | 4/2005 | Dodds |
| 2005/0120019 A1 | 6/2005 | Rigoutsos et al. |
| 2005/0143928 A1 | 6/2005 | Moser |
| 2005/0154627 A1 | 7/2005 | Zuzek et al. |
| 2005/0170321 A1 | 8/2005 | Scully |
| 2005/0170528 A1 | 8/2005 | West |
| 2005/0176057 A1 | 8/2005 | Bremer |
| 2005/0191678 A1 | 9/2005 | Lapointe |
| 2005/0203900 A1 | 9/2005 | Nakamura et al. |
| 2005/0208454 A1 | 9/2005 | Hall |
| 2005/0216208 A1 | 9/2005 | Saito |
| 2005/0260610 A1 | 11/2005 | Kurtz |
| 2005/0278125 A1 | 12/2005 | Harwood et al. |
| 2005/0278317 A1 | 12/2005 | Gross |
| 2006/0052945 A1 | 3/2006 | Rabinowitz |
| 2006/0059159 A1 | 3/2006 | Truong et al. |
| 2006/0064415 A1 | 3/2006 | Guyon et al. |
| 2006/0129034 A1 | 6/2006 | Kasabov |
| 2006/0184557 A1 | 8/2006 | Pollack et al. |
| 2006/0195335 A1 | 8/2006 | Christian et al. |
| 2006/0206483 A1 | 9/2006 | Knepper et al. |
| 2006/0206569 A1 | 9/2006 | Heidloff et al. |
| 2006/0235881 A1 | 10/2006 | Masarie et al. |
| 2006/0240862 A1 * | 10/2006 | Neven et al. .................. 455/550.1 |
| 2006/0293921 A1 | 12/2006 | McCarthy et al. |
| 2007/0016568 A1 | 1/2007 | Amir et al. |
| 2007/0027636 A1 | 2/2007 | Rabinowitz |
| 2007/0027850 A1 | 2/2007 | Chan et al. |
| 2007/0050354 A1 | 3/2007 | Rosenberg |
| 2007/0061166 A1 | 3/2007 | Ramasubramanian et al. |
| 2007/0067297 A1 | 3/2007 | Kublickis |
| 2007/0106536 A1 | 5/2007 | Moore |
| 2007/0106754 A1 | 5/2007 | Moore |
| 2007/0116036 A1 | 5/2007 | Moore |
| 2007/0122824 A1 | 5/2007 | Tucker |
| 2007/0150464 A1 | 6/2007 | Brave |
| 2007/0220017 A1 | 9/2007 | Zuzarte et al. |
| 2007/0260128 A1 | 11/2007 | Hogan et al. |
| 2007/0271247 A1 | 11/2007 | Best |
| 2008/0004848 A1 | 1/2008 | Avey |
| 2008/0040151 A1 | 2/2008 | Moore |
| 2008/0059431 A1 | 3/2008 | Aoki et al. |
| 2008/0208840 A1 | 8/2008 | Zhang et al. |
| 2008/0215581 A1 | 9/2008 | Messing |
| 2008/0228706 A1 | 9/2008 | Kenedy et al. |
| 2008/0228797 A1 | 9/2008 | Kenedy et al. |
| 2008/0235046 A1 | 9/2008 | Fitzpatrick et al. |
| 2008/0256023 A1 | 10/2008 | Nair |
| 2008/0256052 A1 | 10/2008 | Kar et al. |
| 2008/0294607 A1 * | 11/2008 | Partovi et al. .................. 707/3 |
| 2009/0048997 A1 | 2/2009 | Manickam et al. |
| 2009/0083654 A1 | 3/2009 | Nickerson et al. |
| 2009/0094261 A1 | 4/2009 | Jung et al. |
| 2009/0209270 A1 * | 8/2009 | Gutierrez et al. .......... 455/456.3 |
| 2009/0234878 A1 * | 9/2009 | Herz et al. .................. 707/102 |
| 2009/0271375 A1 | 10/2009 | Hyde et al. |
| 2010/0027780 A1 | 2/2010 | Jung et al. |
| 2010/0041958 A1 | 2/2010 | Leuthardt et al. |
| 2010/0063930 A1 | 3/2010 | Kenedy et al. |

FOREIGN PATENT DOCUMENTS

| | | |
|---|---|---|
| WO | WO03076895 A2 | 9/2003 |
| WO | WO2005/086891 | 9/2005 |
| WO | WO2006052952 A2 | 5/2006 |

OTHER PUBLICATIONS

Peedicayil, "Epigenetic Therapy—A New Development in Pharmacology", Indian Journal of Medical Research, Jan. 2006, pp. 17-24, 123 (1), Council of Medical Research, India.

Carson et al., Abnormal Psychology and Modern Life, 8th edition, 1988, pp. 56-57, Scott Foresman and Company, Glenview, IL, USA.

Harvard School of Public Health / Harvard Center for Cancer Prevention, "Your Disease Risk" website for calculating disease risk, 34 exemplary pages submitted including heart disease risk estimation and listings of risk factors, last accessed via the World Wide Web on Apr. 30, 2007, at the URL address: <<http://www.yourdiseaserisk.harvard.edu/english/index.htm>>.

Mostafa, "Seeking Better Web Searches", Scientific American, Feb. 2005, pp. 67-73, 292 (2), Scientific American Inc., USA.

Brin et al., "The Anatomy of a Large-Scale Hypertextual Web Search Engine", pp. 1-20, last accessed via the World Wide Web on Nov. 21, 2008, at the URL address: <<http://infolab.stanford.edu/pub/papers/google.pdf>>.

Dhyani et al., "A Survey of Web Metrics"—Note: Galley Proof Document, pp. 1-42, last accessed via the World Wide Web on Dec. 29, 2008, at the URL address: <<http://www.cais.ntu.edu.sg/~assourav/papers/ACMCS-02-Metric.pdf>>.

Jiawei Han; Discovery of Multiple-Level Association Rules from Large Database' 1995; pp. 1-12.

Serafim Batzoglou, Lior Pachter, Jill P. Mesirov, et al. "Human and Mouse Gene Structure: Comparative Analysis and Application to Exon Prediction." Genome Research. 2000 10: 950-958. Copyright 2000, Cold Spring Harbor Laboratory Press.

Klein, T. E. et al. Integrating genotype and phenotype information: an overview of the PharmGKB project. The Pharmacogenomics Journal 1, 167-170 (2001).

Das, S. Filters, wrappers and a boosting-based hybrid for feature selection. In Proceedings of the Eighteenth International Conference on Machine Learning, 74-81 (Morgan Kaufmann Publishers Inc., San Francisco, CA, USA, 2001).

Duan, K.-B. B., Rajapakse, J. C., Wang, H. & Azuaje, F. Multiple svm-rfe for gene selection in cancer classification with expression data. IEEE transactions on nanobioscience 4, 228-234 (2005).

Nielsen, T. et al. Molecular characterisation of soft tissue tumours: a gene expression study. The Lancet 359, 1301-1307 (2002).

Cooper, D. N. & Krawczak, M. The mutational spectrum of single base-pair substitutions causing human genetic disease: patterns and predictions. Human Genetics 85, 55-74 (1990).

Wagner, SF. Introduction to Statistics. Harper Collins Publishers (1992). pp. 23-30.

Prakash M. Nadkarni, et al. "Data Extraction and Ad Hoc Query of an Entity-Attribute-Value Database", Journal of the American Medical Informatics Association, vol. 5, No. 6, Nov./Dec. 1998, pp. 511-527.

Mani et al., Causal Discover From Medical Textual Data, Fall 2000, Hanley and Belfus Publishers, pp. 542-546.

Roddick et al., Exploratory Medical Knowledge Discover: Experiences and Issues, Jul. 2003, ACM, vol. 5, Issue 1, pp. 94-99.

Prather et al., Medical data mining: knowledge discovery in a clinical data warehouse, Fall 1997, Proceedings of the AMIA Annual Fall Symposium, pp. 101-105.

Cespivova et al., Roles of Medical Ontology in Association Mining CRISP-DM Cycle, Proceedings of the ECML/PKDD04 Workshop on Knowledge Discovery and Ontologies, PISA 2004, 12 pages.

Abe et al., Implementing an Integrated Time-Series Data Mining Environment Based on Temporal Pattern Extraction Methods: A Case Study of an Interferon Therapy Risk Mining for Chronic Hepatitis, 2006, New Frontiers in Artificial Intelligence, Lecture Notes in Computer Science, vol. 4012/2006, pp. 425-435.

Hitsch et al., "What Makes You Click?—Mate Preference and Matching Outcomes in Online Dating", MIT Sloan Research Paper No. 4603-06, Apr. 2006. 62 pages.

Vrbsky, S.V. & Liu, J.W.S. "APPROXIMATE—A Query Processor That Produces Monotonically Improving Approximate Answers." IEEE Transactions on Knowledge and Data Engineering 5, 1056-1068 (1993).

Anonymous, "Frequency" (Web Definition), Feb. 24, 2011, Wikipedia, p. 1.

"Unimobile Launches Advanced Wireless Data Platform and Services to Extend the Reach of Enterprise Applications'—PRNEWSWIRE, Feb. 13, 2001".

"Syed Sibte Raza Abidi; Leveraging XML-Based electronic medical records to extract experiental clinical knowledge. Anautomated approach to generate cases for medical case-based reasoning systems; Syed Sibte Raza Abidi; 2002; InformationJournal of Medical Information; 68; pp. 187-203".

* cited by examiner

A.

| doc_ID = 101 | word_ID = cystic | # of hits = 4 | hit hit hit hit |
|---|---|---|---|
| | word_ID = fibrosis | # of hits = 4 | hit hit hit hit |
| | pangenetic_ID = CFTR F508 mutation | # of hits = 1 | hit |

B.

| doc_ID = 101 | word_ID = cystic | # of hits = 4 | hit hit hit hit |
|---|---|---|---|
| | word_ID = fibrosis | # of hits = 4 | hit hit hit hit |
| | pangenetic_ID = CFTR F508 mutation | # of hits = 4 | hit hit hit hit |

C.

| Plain hit: | capitalization | relative font size | word position in text | |
|---|---|---|---|---|

| Fancy hit: | capitalization | relative font size | type | word position |
|---|---|---|---|---|

| Anchor hit: | capitalization | relative font size | type | doc_ID | word position |
|---|---|---|---|---|---|

*Fig. 1*

|  | Item 1 | Item 2 | Item 3 |
|---|---|---|---|
| User 1 | Like | Dislike | Like |
| User 2 | Like | Dislike | Like |
| User 3 | Dislike | Like | Dislike |
| User 4 | Dislike | Like | Dislike |
| User 5 | Dislike | Like | Like |
| User 6 | Dislike | Like | Like |
| User 7 | Like | Dislike | Dislike |
| User 8 | Like | Dislike | Dislike |

*Fig. 2*

|  | Item 1 | Item 2 | Item 3 |
|---|---|---|---|
| Rs4961 = (T;T)<br>Rs5186 = (C;C) | Like | Dislike | Like |
| Rs4961 = (T;T)<br>Rs5186 = (C;C) | Like | Dislike | Like |
| Rs3865418 = (T;C)<br>Rs6997709 = (G;G) | Dislike | Like | Dislike |
| Rs3865418 = (T;C)<br>Rs6997709 = (G;G) | Dislike | Like | Dislike |
| Rs11110912 = (G;C)<br>Rs1937506 = (G;G) | Dislike | Like | Like |
| Rs11110912 = (G;C)<br>Rs1937506 = (G;G) | Dislike | Like | Like |
| Rs3755351 = (C;A)<br>Rs3794260 = (G;G) | Like | Dislike | Dislike |
| Rs3755351 = (C;A)<br>Rs3794260 = (G;G) | Like | Dislike | Dislike |

Pangenetic Cluster 1: rows 1–2
Pangenetic Cluster 2: rows 3–4
Pangenetic Cluster 3: rows 5–6
Pangenetic Cluster 4: rows 7–8

|  | Item 1 | Item 2 | Item 3 |
|---|---|---|---|
| Pangenetic Cluster 1 — Rs4961 = (T;T), Rs5186 = (C;C) | 5 | 2 | 4 |
| Pangenetic Cluster 1 — Rs4961 = (T;T), Rs5186 = (C;C) | 5 | 1 | 5 |
| Pangenetic Cluster 2 — Rs3865418 = (T;C), Rs6997709 = (G;G) | 3 | 5 | 1 |
| Pangenetic Cluster 2 — Rs3865418 = (T;C), Rs6997709 = (G;G) | 2 | 3 | 2 |
| Pangenetic Cluster 3 — Rs11110912 = (G;C), Rs1937506 = (G;G) | 1 | 5 | 3 |
| Pangenetic Cluster 3 — Rs11110912 = (G;C), Rs1937506 = (G;G) | 3 | 4 | 3 |
| Pangenetic Cluster 4 — Rs3755351 = (C;A), Rs3794260 = (G;G) | 4 | 2 | 1 |
| Pangenetic Cluster 4 — Rs3755351 = (C;A), Rs3794260 = (G;G) | 4 | 4 | 1 |

B.

|  |  | Item 1 | Item 2 | Item 3 |
|---|---|---|---|---|
| Pangenetic Cluster 1 | Rs4961 = (T;T), Rs5186 = (C;C) | 5 | 1.5 | 4.5 |
| Pangenetic Cluster 2 | Rs3865418 = (T;C), Rs6997709 = (G;G) | 2.5 | 4 | 1.5 |
| Pangenetic Cluster 3 | Rs11110912 = (G;C), Rs1937506 = (G;G) | 2 | 4.5 | 3 |
| Pangenetic Cluster 4 | Rs3755351 = (C;A), Rs3794260 = (G;G) | 4 | 3 | 1 |

| | | Item 1 | Item 2 | Item 3 |
|---|---|---|---|---|
| Pangenetic Cluster 1 — Subgroup 1 | Rs4961 = (T;T) Rs5186 = (C;C) | 5 | 2 | 3 |
| | Rs4961 = (T;T) Rs5186 = (C;C) | 5 | 1 | 3 |
| Pangenetic Cluster 1 — Subgroup 2 | Rs4961 = (T;T) Rs5186 = (C;C) | 4 | 1 | 5 |
| | Rs4961 = (T;T) Rs5186 = (C;C) | 2 | 1 | 5 |
| Pangenetic Cluster 2 — Subgroup 1 | Rs11110912 = (G;C) Rs1937506 = (G;G) | 1 | 5 | 3 |
| | Rs11110912 = (G;C) Rs1937506 = (G;G) | 3 | 5 | 3 |
| Pangenetic Cluster 2 — Subgroup 2 | Rs11110912 = (G;C) Rs1937506 = (G;G) | 2 | 4 | 1 |
| | Rs11110912 = (G;C) Rs1937506 = (G;G) | 3 | 4 | 1 |

B.

| | | Item 1 | Item 2 | Item 3 |
|---|---|---|---|---|
| Pangenetic Cluster 1 Subgroup 1 | Rs4961 = (T;T) Rs5186 = (C;C) | 5 | 1.5 | 3 |
| Pangenetic Cluster 1 Subgroup 2 | Rs4961 = (T;T) Rs5186 = (C;C) | 3 | 1 | 5 |
| Pangenetic Cluster 2 Subgroup 1 | Rs11110912 = (G;C) Rs1937506 = (G;G) | 2 | 5 | 3 |
| Pangenetic Cluster 2 Subgroup 2 | Rs11110912 = (G;C) Rs1937506 = (G;G) | 2.5 | 4 | 1 |

*Fig. 5*

Data Mask # 1:  U U U M M M U U U M M M M M U U U U U U U M M U M M U U U M M M M U M U U Data Mask # 2:  U U U U U U U M M M M M M U U M M U U U U M M M M U U U U U U U U U U Data Mask # 3:  U U U M M M U U U M M U M M U U U U U M U M M U M M U U U M M M M U U U U Consensus :    U U U M M M U U M M M M M M U U M M U U M U M M M M U U U M M M M U M U U

Fig. 7

PANGENETIC WEB ITEM RECOMMENDATION SYSTEM

FIELD OF THE INVENTION

The invention relates to methods, systems, software and databases for delivering personalized web search results and online recommendations based on the pangenetic attributes of individuals. More particularly, these approaches rely on correlations determined between specific pangenetic attributes—also referred to in this disclosure as pangenetic data—and historical online behavior and preferences of users with respect to information and offerings contained in webpages.

BACKGROUND OF THE INVENTION

Internet search engines generally rely on the preprocessing of webpage information prior to performing a user specified search. At some time prior to the search, the web content is crawled by a 'spider' module (web crawler) which logs and retrieves webpages while an indexer module analyzes the word and syntactic content of each webpage in order to index and store content. This information correlates to an index of relevance based on a comparison of the search terms and what is indexed. In addition to an IR score, the above search engine can compute a page ranking score using an algorithm which evaluates the quantity and quality of inbound hyperlinks of each webpage. No correlation of the genetic characteristic of the searcher and the web content is used.

SUMMARY OF THE INVENTION

The methods, systems, software and databases in this application are for delivering personalized web search results and online recommendations based on the pangenetic attributes of individuals. The approach relies, in part, on correlations determined between specific pangenetic attributes and historical online behavior and preferences of users with respect to information and offerings contained in webpages. These correlations between pangenetic attributes and web behavior can be used to predict future behavior and preferences of users and others like them. By linking known genetic attributes to webpages, search engines can efficiently retrieve information and offerings that better satisfy the user's interests, preferences and needs.

BRIEF DESCRIPTION OF THE DRAWINGS

The following detailed description will be better understood when read in conjunction with the appended drawings, in which there is shown one or more of the multiple embodiments of the present invention. It should be understood, however, that the various embodiments are not limited to the precise arrangements and instrumentalities shown in the drawings.

FIG. 1 illustrates examples of document index entries, word hit lists, and hit types;

FIG. 2 illustrates an item feedback matrix containing descriptive binary ratings;

FIG. 3 illustrates a pangenetic based item feedback matrix containing descriptive binary ratings and identified pangenetic clusters;

FIG. 4 illustrates pangenetic based item feedback matrices containing numerical ratings and identifiable pangenetic clusters;

FIG. 5 illustrates pangenetic based item feedback matrices containing numerical ratings and identifiable pangenetic clusters and rating subgroups;

FIG. 7 illustrates abstract representations of data masks;

DETAILED DESCRIPTION

Figure 6:
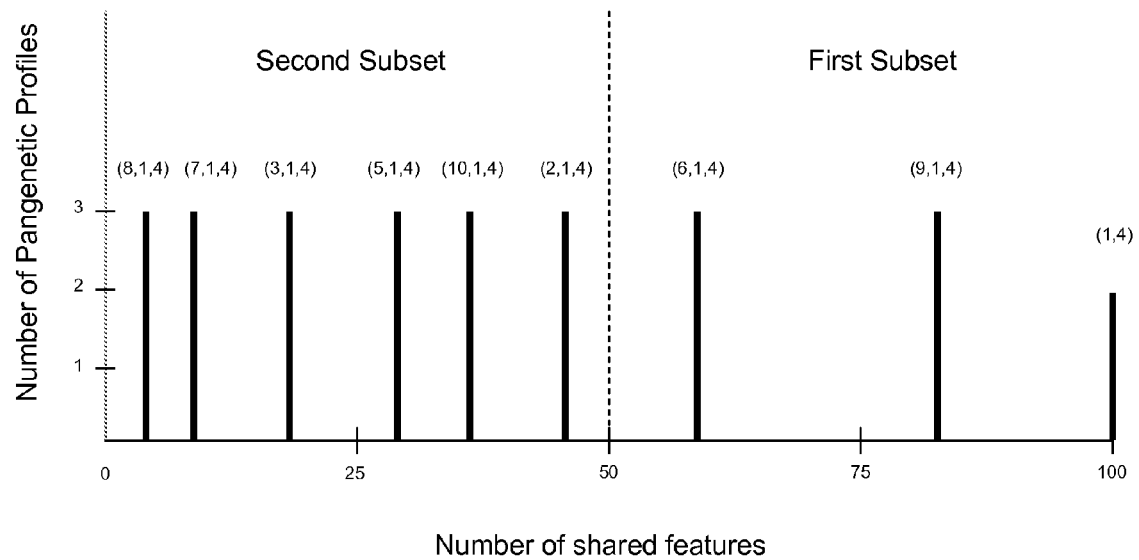
FIG. 6 illustrates one step of a computationally efficient method for compiling co-associating attributes.

With the recent introduction and successes of single nucleotide polymorphism (SNP) sequencing, full genomic sequencing and epigenetic sequencing in humans, wide ranging applications that utilize the pangenetic attributes (genetic and epigenetic attributes) of individuals become possible. Herein we disclose methods, systems, software and databases for delivering personalized web search results and online recommendations based on the pangenetic attributes of individuals. These approaches rely on correlations determined between specific pangenetic attributes—also referred to in this disclosure as pangenetic data—and historical online behavior and preferences of users with respect to information and offerings contained in webpages. These correlations can be used to predict the future behavior and preferences of users. By linking pangenetic attributes to webpages as metadata, for example, and then comparing that metadata to the pangenetic profile of a user, web search engines can be enabled to retrieve information and offerings that better satisfy the user's interests, preferences and needs.

In one embodiment, the present invention is designed to utilize correlations between pangenetic attributes of users of the World Wide Web (WWW or web) and the feedback and behaviors they express with respect to web items (objects and content of the web) to improve the relevancy of web items retrieved and/or recommended for future users. More specific applications include those within the healthcare field involving medical information retrieval for diagnosis and treatment of patients whose pangenetic attributes are known. Personalization of information retrieval using pangenetic attributes of individuals has the potential to greatly increase efficiency and accuracy by minimizing resources that are spent retrieving less relevant results.

In another embodiment, a pangenetic based search and recommendation system has potential benefits for many applications, not the least of which is in providing user recommendations for online shopping. Take for example, a search for music earphones. The human ear exhibits great variability from individual to individual with respect to internal ear canal size and shape, external ear size and shape, and perception of sound frequencies across the audible range. Consequently, user ratings and preferences of earphones vary greatly, so that while many individuals may give the highest possible rating to a particular make and model of earphone, other individuals may find the frequency response and/or physical fit of that earphone to be unacceptable. So despite the availability of user feedback through existing online rating and recommendation systems, a future consumer (i.e., user) may be unable to identify the best product for themselves based on existing search and recommendation systems because they have little or no information regarding how similar they are to other consumers that rated the product highly. Since the individual characteristics of each person's hearing response (in the normal undamaged state) and ear structure are dictated predominantly by information encoded in their genome, a comparison of the relevant genetic and epigenetic attributes responsible for particular variations in ear morphology and frequency sensitivity of a current consumer with that of past consumers who found particular earphones to be outstanding can enable a much more reliable recommendation to guide the consumer directly to those earphones that will provide them with the highest level of satisfaction in terms of sound quality and fit. While the user may direct a search using keywords that specify what type of earphone is desired—earbud vs. in-ear canal earphone vs. ear-clip earphone vs. neck-band earphone vs. head-band earphone, etc.—incorporating a pangenetic similarity comparison between the current consumer and past consumers who found particular types of earphones most satisfactory can dramatically narrow down the selection of possible recommendations within any particular earphone category.

This approach helps ensure that the best choices for an individual consumer are recommended and also enables avoiding choices which would likely prove unsatisfactory. Benefits extend to others including product sellers who typically loose both time and money when a consumer purchases a product based on current recommender systems, is dissatisfied with the product, and then returns the product for a refund. Many other aspects of human perception and sensory preferences are dictated at least in part by individual pangenetic characteristics. Individual differences in taste, smell, and color perception, as well as preferences for certain types of melodies and instrument tonalities in music and particular thematic subject matter in movies and books, are associated with and can be extracted from our genetic and epigenetic makeups. Consequently, web based search and recommendation of a wide variety of items including foods, wines, perfumes, colons, music, movies and books can be significantly enhanced with respect to both efficiency and consumer satisfaction by evaluating consumers' pangenetic attributes. We envision a Pangenetic World Wide Web, or simply Pangenetic Web, in which search, navigation, online user behavior, item recommendation, and social networking are all guided by the pangenetic profiles of users.

Existing internet search engines rely on the preprocessing of webpage information prior to performing a user specified web search, in which nearly the entire content of the WWW is crawled by a 'spider' module (web crawler) which logs and retrieves webpages while an indexer module analyzes the word and syntactic content of each webpage in order to index and store that content in various datasets for rapid access during a user query. Words occurring in a webpage can be represented as word_IDs (word identifiers) which can be linked (using a lexicon hash table, for example) to doc_IDs (document identifiers) that represent the webpage documents in which those words occur. The doc_IDs may be stored a doclist index containing additional information which identifies the total number of occurrences of a word within a webpage and the context of each occurrence. The web search engine can then retrieve and rank webpages in part by matching user queried keywords to the respective word_IDs and following pointers (i.e. links) into the doclist index which contains word hitlists providing the number and context of occurrences of each keyword within each webpage document that is a hit for (i.e., contains) that keyword. The higher the number of occurrences and the more significant the context of each occurrence of a keyword in a webpage, the higher the relevancy score computed for the webpage, which can be referred to as an Information Retrieval (IR) score. Also, webpages that contain hits for a greater number of the user's query keywords receive a higher IR score than those that hit on fewer keywords. While the term webpage is used, the above and following concepts apply more broadly to web items that may not be webpages, such as indexes, data files and other documents. The term 'web items' refers to data contents of the internet and WWW.

One prominent internet search engine design can store a lexicon dataset representing millions of words using word_IDs and a hash table of pointers indicating which webpage documents each of the words occurs in. The search engine has access to forward index and inverted index datasets which record the total number of occurrences of each of the words in the respective webpages, as well as hitlist datasets which contain context information indicating the type of word occurrence in addition to the number of hits. Type of occurrence includes information such as whether the word occurs in the URL, title, body, or anchor hypertext of a particular webpage, as well as position of occurrence, font style, and relative font size of each occurrence of the word on the webpage. These context attributes are incorporated into a computation of a type-weight for each occurrence of a word. The type-weights make up a vector that is indexed by type. Also, the search engine counts the number of hits (i.e., number of occurrences) of each type in the hit list and then converts every count into a count-weight. Count-weights increase linearly with counts at first but quickly taper off, so that beyond a certain point increasing counts no longer contribute to the count-weight. The IR score for the document is computed as the dot product between the vector of count-weights and the vector of type-weights.

In addition to an IR score, the above search engine can compute a page ranking score using an algorithm which evaluates the quantity and quality of inbound hyperlinks of each webpage. The higher the quality and quantity of the inbound hyperlinks pointing to a webpage, the higher the page ranking score will be for that webpage. The search engine combines the hyperlink-based page ranking score with the IR score to derive a final rank for a webpage which determines whether that webpage will be listed in the Search Engine Results Page (SERP), and where in the listing it will appear based on its rank relative to other webpages listed in the SERP.

Herein we disclose that information retrieval systems, methods, software and databases, especially those involving web search engines, can be enhanced by incorporating an individual's pangenetic attributes to personalize results, thereby providing greater relevancy and accuracy of results for a particular user. The methods and systems disclosed herein can be used as stand alone methods and systems for pangenetic based web searching, or alternatively, as complementary methods and systems to more traditional methods and systems, such as those described above, to enable incorporation of pangenetic based web search as an add-on functionality. Pangenetic attributes can be contained within the source code of a webpage, or they may be externally associated with a webpage by storing them within a search engine lexicon and linking them to the webpage. The latter can require the parsing and indexing of a webpage in a first step, comparing the content of the compiled index from the webpage with a pangenetic correlation table to determine pangenetic attributes that should be linked to the webpage in a second step, and storing the relevant pangenetic attributes from the correlation table in association with the webpage in a third step.

Within this disclosure, the term 'attribute' refers a quality, trait, characteristic, feature relationship, property, factor, object, or data associated with or possessed by an individual, a group of individuals, an activity, a state, or datum. The term 'pangenetic attribute' refers to genetic and epigenetic attributes. The term 'non-pangenetic attribute' refers to attributes other than genetic or epigenetic attributes. In one embodiment, non-pangenetic attributes can be selected from the group consisting of physical attributes (i.e., attributes describing any material quality, trait, characteristic, property or factor of an individual present at the atomic, molecular, cellular, tissue, organ or organism level, excluding genetic and epigenetic attributes), behavioral attributes (i.e., attributes describing any singular, periodic, or aperiodic response, action, opinion or habit of an individual with respect to internal or external stimuli, including but not limited to an action, reflex, emotion or psychological state that is controlled or created by the nervous system on either a conscious or subconscious level), and situational attributes (i.e., attributes describing any object, condition, influence, or milieu that surrounds, impacts or contacts an individual). Examples of non-pangenetic attributes of a user include demographics such as their age, gender, ethnicity, marital status, and zip code.

Within this disclosure, the term 'genetic attribute' refers to attributes relating to a genome, genotype, haplotype, chromatin, chromosome, chromosome locus, chromosomal material, deoxyribonucleic acid (DNA), allele, gene, gene cluster, gene locus, genetic polymorphism, genetic mutation, genetic mutation rate, nucleotide, nucleotide base pair, single nucleotide polymorphism (SNP), restriction fragment length polymorphism (RFLP), variable tandem repeat (VTR), microsatellite sequence, genetic marker, sequence marker, sequence tagged site (STS), plasmid, transcription unit, transcription product, gene expression level, genetic expression (i.e., transcription) state, ribonucleic acid (RNA), or copy DNA (cDNA), including the nucleotide sequence and encoded amino acid sequence associated with any of the above.

Within this disclosure, the term 'epigenetic attribute' refers to attributes relating to modifications of genetic material that affect gene expression in a manner that is heritable during somatic cell divisions and sometimes heritable in germline transmission, but that is nonmutational to the DNA sequence and is therefore fundamentally reversible, including but not limited to methylation of DNA nucleotides and acetylation of chromatin-associated histone proteins.

The attribute profile of an individual, which can be a pangenetic profile, a non-pangenetic profile or a hybrid (combined) attribute profile containing both pangenetic and non-pangenetic attributes, is preferably provided to embodiments of the present invention as a dataset record whose association with the individual can be indicated by a unique identifier contained in the dataset record. An actual attribute of an individual can be represented in data form as an attribute descriptor in attribute profiles, records, datasets, and databases. Herein, both actual attributes and attribute descriptors may be referred to simply as attributes. In one embodiment, statistical relationships and associations between pangenetic and non-pangenetic attributes as determined by the methods disclosed herein are a direct result of relationships and associations between actual attributes of an individual, including behavioral attributes they exhibit (e.g., online computing and web surfing behaviors). Individuals, attribute profiles and attributes can be real and/or measurable, or they may be hypothetical and/or not directly observable.

To provide the pangenetic data needed for pangenetic based web searching, genetic and/or epigenetic sequencing of an individual can be performed, typically through SNP sequencing or genomic sequencing methods, and the pangenetic data obtained through sequencing can be associated with the individual as a pangenetic data profile (pangenetic profile), for example, that can be subsequently accessed by web search engines during a search query. Access and reading of an individual's pangenetic profile may involve various security measures such as authentication verification, as well as masking of certain pangenetic attributes to maintain anonymity of the individual with respect to identification by third parties or to maintain privacy with respect to particular pangenetic attributes which could reveal health conditions or traits that the individual desires to keep confidential.

Additionally, pangenetic attributes need to be linked or associated with webpages to enable retrieval of webpages that best match the individual's pangenetic profile. More specifically, in one embodiment pangenetic attributes can be linked to a webpage as a whole, based on the categories, topics or product offerings of the webpage. In another embodiment, pangenetic attributes can be linked to a webpage through associations with particular words or phrases in the text of a webpage. For example, the specific gene mutation responsible for the majority of cystic fibrosis disease cases is the 'CFTR gene F508 mutation' which can be linked to the phrase 'cystic fibrosis' appearing in text content of web pages. Similarly, other pangenetic attributes known to cause cystic fibrosis can simultaneously be linked to the same 'cystic fibrosis' phrase. While pangenetic attributes can exist as text on a webpage, it is expected that pangenetic attributes will be linked to webpages as hidden attributes in the form of metadata, such as meta-tags and meta-keywords that provide an additional layer of meaning and interpretation to the explicit content of webpages, consistent with visions for a semantic web. The pangenetic metadata associated with a webpage can be used to indicate that a user sharing some or all of those pangenetic attributes will be more likely to benefit or be satisfied with the content offered by that webpage, and it should therefore receive a higher rank or higher listing position in the search results presented to the user.

As an example, where a particular combination of pangenetic attributes are found to be causally associated with a subtype of multiple sclerosis (MS), each of those pangenetic attributes can be stored as meta-keywords linked to websites providing information about the that MS subtype, healthcare provider websites that advertise specialized treatment for that MS subtype, pharmacy websites that offer medications for treating that MS subtype, and website support groups that offer help and information for people suffering with that MS subtype. Despite the existence of several subtypes of the disease, when a user performs a web search regarding MS, the particular pangenetic attributes of the user (or an individual represented by a user, such as a patient represented by a healthcare professional who acts as the user) can be utilized by the search engine to ensure that the subset of websites offering information, products and services associated with the pertinent genetic subtype of MS are retrieved and presented with higher rank and listing position, regardless of whether the user knows or is even aware of the relevant subtype of the disease. In one embodiment, the search results listed on a SERP can include the pangenetic attributes of the user that were a match for each of the webpage documents listed in the SERP.

In one embodiment, knowing which specific pangenetic attributes should be linked to a webpage requires knowing which pangenetic attributes historically correlate with satisfaction and/or utility (i.e., relevance) of the webpage's content offerings for at least one subgroup of users. Data for correlations between consumers' pangenetic attributes and their preferences and satisfaction with webpage content offerings can be obtained through at least two approaches. One approach is to obtain the data by monitoring and recording the behaviors and feedback of consumers and then determining correlations of those behaviors and feedback ratings with pangenetic attributes of the consumers using pattern finding methods known to those of skill in the art. Passive collaborative filtering methods can be used to monitor the online behavior of users and then determine correlations between subsets of their pangenetic attributes and particular behaviors, while active collaborative filtering methods can be used to record feedback from users and then determine correlations between subsets of their pangenetic attributes and their self-reported feedback (e.g., preferences and satisfaction levels) with respect to online information and offerings. Data for determining correlations can also be derived from consumer purchasing behavior at bricks-and-mortar stores by analyzing frequent shopper (club member) card data and/or credit card purchase history data, also through passive filtering. Once correlations are determined, they can be stored in a database and later accessed to extract information that can be used to predict an individual consumer's online behavior, preferences, and feedback based on their pangenetic attributes alone or in combination with non-pangenetic attributes of the consumer such as demographics. The population of consumers from which this data is obtained can be a designated test population, or it can a group of individuals in a user population that have consented to having at least a portion of their pangenetic data accessed for the purpose of receiving personalized information search capabilities and content recommendations in the future. Cross-system collaborative filtering can be used to combine user behavior and preference data compiled across multiple recommender systems in a privacy preserving manner.

A second approach for acquiring pangenetic based correlations is to obtain the correlation data from professionals such as scientists, researchers, and healthcare providers who evaluate and publish associations between pangenetic data and health conditions, behaviors, products, and services for purposes such as disease diagnosis and treatment, scientific research, and product development (e.g., pharmaceutical development). Data from these and similar sources can be further analyzed and refined for extracting information for web search applications. In certain instances, third parties may have collections of pangenetic and non-pangenetic information, without having attempted to determine correlations between the data. Such data can be subsequently processed with pattern finding methods to derive correlations that can be also used for web search based information retrieval. The correlations acquired by any of the above approaches can be derived from either rigorous statistical associations, or less desirably from non-statistical (i.e., informal) trends and inferences.

Many of the embodiments of the inventions of the present disclosure involve the comparison of pangenetic data, often the pairwise comparison of individual genetic attributes, to determine pangenetic matches, overall quantity of pangenetic matches between pangenetic datasets, and pangenetic similarity scores. In one or more embodiments, pangenetic data can be identified as being a match (i.e., equivalent) if they are identical. In one or more embodiments, pangenetic data can be identified as being a match if they are different pangenetic attributes known to be statistically associated with the same item or item preference (e.g., the same level of satisfaction with a particular item). In one or more embodiments, pangenetic data can be identified as being a match if they differ only with respect to one or more silent pangenetic variations (i.e., pangenetic variations those that do not impact a phenotype, outcome or item preference).

In order to link pangenetic attributes to webpage content, pangenetic based correlations can be processed by one or more software modules designed to recognize webpages containing informational content represented by the correlations and then store links between those webpages and the respective pangenetic attributes represented by the correlations. Linking can be accomplished by storing word_IDs representing the pangenetic attributes within datasets accessed by search engines, such as the lexicon dataset compiled from webpages and later read by the search engine upon receiving a user query, and then creating pointers from the word_IDs to the doc_IDs, contained within document index datasets (i.e., indexes), which represent the webpages that contain the content or concepts represented by those word_IDs. So while the pangenetic data can be external metadata that is not contained within the webpage document itself, it can be represented and stored for utilization by search engines in the same manner as both visible webpage text and non-displayed internal metadata contained within the webpage document source code. This allows pangenetic attributes to be incorporated into existing search engine systems used by Google, Yahoo!, Microsoft Network and others. In one embodiment, pangenetic attributes can be represented with word_IDs in a single lexicon dataset which also contains word_IDs representing non-pangenetic words, wherein the word_IDs can be hash values. In one embodiment, pangenetic attributes can be represented with word_IDs in a separate lexicon dataset devoted solely to pangenetic attributes, wherein the word_IDs representing the pangenetic attributes can be hash values. In one or more embodiments, word_IDs representing pangenetic attributes can be referred to as pangenetic_IDs.

Typically, the user would not be expected to enter pangenetic data into their search query as keywords. The search engine can have the ability to identify and/or authenticate the user and then read at least a portion of their pangenetic profile (masked or otherwise). As such, the pangenetic attributes can be hidden from view as metadata associated with the user and as metadata associated with webpages. These pangenetic attributes can be treated as secondary keywords by the search engine. In one embodiment, pangenetic attributes of a user (or another individual for whom the user is performing a web search on behalf of) are used as a secondary means of selecting and ranking webpages. In this particular approach, webpages can be initially retrieved based on user queried keywords or topics, and then pangenetic_IDs that were previously stored in the lexicon and document index datasets can be used to compute pangenetic based scores for the respective webpages they are associated based on matches with the pangenetic profile of the user. More specifically, once a set of webpages have been retrieved based on user query keywords, the doc_IDs of the retrieved webpages can be used for a reverse lookup of pangenetic_IDs associated with those webpages. The associated pangenetic_IDs can be identified and counted for each webpage and then compared to the pangenetic profile of the user to determine the number of pangenetic hits (i.e., quantity of pangenetic matches) that the pangenetic profile has for each webpage. The total number of pangenetic hits recorded between the user's pangenetic profile and a webpage can be divided by the total count of pangenetic word_IDs associated with the webpage to produce a pangenetic score in the form of percent match, for example. The pangenetic score can then be normalized to any scale, for example, a scale of 1 to 10 as used by the ranking system of one prominent web search engine. Following normalization, it is possible to generate a consolidated score by combining the pangenetic score with an IR score, a PageRank or a final SERP rank by averaging, weighted averaging or other mathematical computations known to those of skill in the art. In one embodiment, the resulting composite score can be used as a final rank for determining the selection and ordering of one or more webpages in the SERP.

In one embodiment, the results presented on a SERP can be grouped into separate areas to allow the user to delineate between those results that were selected and ranked based on pangenetic data and those results which were not derived based on pangenetic data. By creating separate groups of results in the SERP, the user is able to save time that would otherwise be spent sifting through less relevant results by focusing their attention on the group of results that best satisfies their needs. In one embodiment, the user is able to indicate to the search engine which group of results in the SERP they are more satisfied with. This user feedback can be used by the search engine in subsequent searches to further refine the results by learning what best meets the needs of the user. For example, if the user prefers the results obtained using pangenetic attribute matching, then the search engine can forego the presentation of webpages based solely on non-pangenetic keywords and only present webpage links on the SERP that were selected and ranked, at least in part, based on pangenetic attributes associated with user and the pangenetic attributes associated with webpages.

FIG. 1A and FIG. 1B illustrate embodiments of partial pangenetic web search engine document indexes for two webpage documents having document identifier numbers 101 and 102, respectively. For illustrative purposes, only the two words 'cystic' and 'fibrosis' from the text of the document are shown. Additionally, the pangenetic word 'CFTR F508 mutation' is shown as an example of a meta-tag that is not contained within the text or source code of the original webpage. It is known that the CFTR F508 mutation occurring within the Cystic Fibrosis Transmembrane Conductance Regulator (CFTR) gene is the most frequent cause of the disease. Note that, in this example, the word_IDs in the index entries were selected to be the same as the actual words themselves. The number of occurrences of each of these words within the text of the webpage or linked to the webpage as metadata is entered in the third field as the number of hits. The fourth field is a hitlist which contains one entry (i.e., hit) for each occurrence of the corresponding word. Each of the 'hit' entries in the hitlist contains additional information not shown, including context of occurrence information for each respective occurrence of the corresponding word. FIG. 1A is designed to illustrate a circumstance where the pangenetic attribute is linked in a simple 1:1 association with the webpage document, and would therefore be counted as a single hit when a user's pangenetic profile matches with that particular pangenetic attribute. FIG. 1B is designed to illustrate a circumstance where a pangenetic attribute is linked to the webpage as multiple occurrences, in this case corresponding with each of the four co-occurrences of the words 'cystic' and 'fibrosis'. For this example, it was found upon parsing the webpage that the words 'cystic' and 'fibrosis' appear juxtaposed as the phrase 'cystic fibrosis' in all four occurrences within the document. Since the CFTR F508 mutation is the most common cause of the disease, it was linked to the webpage for every occurrence of the phrase 'cystic fibrosis'. So when a user's pangenetic profile contains the pangenetic attribute 'CFTR F508 mutation', four hits would be tallied for that webpage with respect to that user and that pangenetic attribute in the process of determining search result rankings.

As indicated, FIG. 1B depicts a scenario where pangenetic attributes can be given additional weight by allowing a pangenetic attribute to be treated like a text word and counted as multiple hits for a single webpage based on multiple 'virtual' occurrences via associations with text words or meta-keywords that occur multiple times within the source code of the webpage. As such, each pangenetic attribute can be assigned the same context information as the text word, phrase or meta-keyword that it is associated with. As illustrated in FIG. 1C, in one embodiment hits can be of three different types depending on context: plain hit, fancy hit, or anchor hit. And as can be seen from the illustration, the information stored for each type of hit record differ slightly. An anchor hit refers to a hypertext that points to the webpage from another webpage, so that the anchor word actually does not appear in the source code of the webpage for which it is counted as a hit. The information stored for the anchor hit, as illustrated, can include a capitalization feature which indicates whether the anchor text is capitalized; a relative font size feature which indicates the size of the anchor text font relative to the other font sizes within the document in which the anchor text appears; a type feature which indicates whether the anchor text appears Uniform Resource Locator (URL), title, or plain text, or whether it is colored, bolded, underlined, italicized or highlighted, for example; a document identifier feature which identifies the webpage document that contains the anchor text; and a word position feature which identifies where in the document the anchor text occurs (for example, a number indicating it is the nth word from the beginning of the document). A fancy hit refers to a hit occurring in a URL, title or meta-tag of the webpage. It contains the same information as an anchor hit with the exception of omission of the doc_ID feature. A plain hit encompasses all other types of hits and contains the same features as a fancy hit with the exception of omission of the type feature. When a pangenetic attribute is assigned context of occurrence information through association with text or meta-tags contained in a webpage, a hit record can be generated for that pangenetic attribute by simply copying the context feature values of the associated text or meta-tag to the hit record for the pangenetic attribute, where the hit type (plain hit, fancy hit, or anchor hit) for the pangenetic attribute can be selected as either the same or different than that of the associated text or meta-tag. The pangenetic attribute, when hit on by a user search, can then contribute to the calculation of an IR score just like traditional keyword hits.

Referring again to the circumstance illustrated in FIG. 1A, where a pangenetic attribute is linked to the webpage as a whole and not to occurrences of particular words or metatags, there may be no relevant hit values to simply copy and transfer to the hit record of the pangenetic attribute. In this case, it is possible to have the system choose both the type of hit and the hit feature values in order to generate the desired weight for a hit on the that pangenetic attribute. For example, a pangenetic attribute that is has a strong association (e.g., statistical correlation) with content of a webpage can be recorded as a fancy hit, and can also be assigned hit feature values that maximize the weight of the hit in an IR score computation. Whereas a pangenetic attribute having a weak association with content of a webpage can be recorded as a plain hit and can be assigned hit feature values that minimize the weight of the hit in an IR score computation. A pangenetic attribute having a moderately strong association can be typed as either a fancy hit with low weight feature values or as a plain hit with high weight feature values, for example, to create a moderate weight for the hit in an IR score computation. If pangenetic hits are not included in a traditional IR score calculation, then a separate calculation can be used which, as previously described, computes the degree of matching between a user's pangenetic profile and the pangenetic attributes linked to a webpage and then normalizes and combines this 'pangenetic score' with an IR score, a page rank score or a final SERP rank by averaging, weighted averaging or other mathematical computations known to those of skill in the art.

As mentioned previously, determining correlations between pangenetic attributes and webpage content can be based on recording the online behaviors and feedback of users whose pangenetic attributes are accessible to a search engine. In one embodiment, a user can login to a search engine which either has access to a stored copy of their pangenetic profile in an associated database server or can be authorized to access the pangenetic data on another database server dedicated to storing pangenetic data of individuals (e.g., a pangenetic server). In another embodiment, users can store a copy of the pangenetic profile as a secure file on the desktop or storage device of a computing device that was used to connect to the web search engine, and the file can be uploaded or accessed by the web search engine upon receiving authorization by the user through the computing device.

Active collaborative filtering can then be used to provide a peer-to-peer approach for deriving correlations between user satisfaction with online content and one or more pangenetic attributes by first gathering explicit feedback from users. Explicit feedback can be obtained by recording the rating of a webpage by a group of users and then correlating rating scores one at a time with the pangenetic attributes that statistically segregate with each score. For example, if users having a particular combination of pangenetic attributes are observed to predominantly rate a particular webpage as a score of 5 on a scale of 1-5, then that combination of pangenetic attributes can be linked to that webpage so it will be more highly ranked and/or more frequently recommended to a user who possesses some or all of those particular pangenetic attributes. Active feedback for the purpose of developing correlations can also be collected by asking a user to rank a collection of webpage items on a qualitative scale (e.g., favorite to least favorite), presenting a user with two or more webpage offerings and asking the user to choose the best one, or asking a user to choose a list of webpage items that they like, for example. Software methods and systems designed for active collaborative filtering to collect explicit feedback from users can incorporate feedback input fields on the webpages in which the pertinent web content appears, interactive pop-up windows, or questionnaires integrated into the web browser.

Passive collaborative filtering is an alternative to active filtering for collecting data on user behavior and preferences that can be used to derive correlations between pangenetic attributes of users and relevant webpage offerings. Passive filtering is based on the assumption that the preferences and opinions of users can be implied by their actions and requires observing and recording online user behavior to determine user feedback implicitly without necessitating user inputs to acquire feedback ratings and opinions. This has the result of reducing demands on the user while reducing variability and information biases that afflict other types of feedback systems, such as surveillance bias (e.g., only certain types of people are willing to take the time to provide active feedback, thereby potentially skewing feedback data so that it may be unrepresentative of the general population of users as a whole) and reporting bias (e.g., users may provide insincere or inaccurate feedback in an active peer-to-peer system where they aware that others can view their feedback). More specifically, passive feedback can be obtained by recording what webpages and content a user viewed, listened to, or otherwise interacted with; how long a user viewed, listened to or interacted with a webpage or specific content (i.e., user dwell time); how much scrolling a user did on a webpage; what items a user bookmarked, printed out or saved (e.g., in shopping cart) for later consideration; what items a user purchased; what items a user recommended to others; the number of times a user queried particular topics or clicked on particular links; and details of a user's social network to discover interests, likes and dislikes. Methods for collecting implicit feedback can utilize software operating through a web browser to record the above behaviors as well as for collecting characteristics of the user's social network. In one embodiment, the software for passively recording user behaviors and/or social network characteristics can be applets running in the web browser and communicating with an external or remote database server.

Both active and passive collaborative filtering can be implemented through social networking applications and websites. A version of social networking can be provided to enable participants to share their pangenetic data with others in the network, or designated subgroups within the network such as friends, friends of friends, or business contacts. The system can correlate patterns of those users' pangenetic attributes with their behaviors, interests, needs and goals as expressed through the network. Subsequently, the identified pangenetic patterns can be used as the basis for inviting new friends or contacts into a user's network or group of friends, for example, under the premise that possession of certain pangenetic attribute patterns will help ensure that the newly invited friend or contact will have compatible behaviors, interests, needs and goals. The pangenetic associated information collected from social networks can be used to provide necessary data to enable web searching systems and item recommender and prediction systems.

Web based recommender systems can be enabled using the same basic principles as web search methods and systems. However, instead of linking pangenetic data in association with webpages through a document index, as in a pangenetic web search system, in pangenetic based recommender and prediction systems the pangenetic data can be associated with specific items within an item feedback matrix. While some of the items represented in the matrix may be webpage links or webpage information content, at least some of the represented items can be physical products, establishments, or tangible services indicated by descriptors. The matrix can also contain feedback data (e.g., scores, ratings, preferences) derived from explicit or implicit user feedback. Feedback data contained in the matrix can be represented as values which are consistent with various kinds of rating scales and scoring systems that provide an indication of the level of user satisfaction, interest or preference for the items represented in the matrix. Feedback data can include item descriptors and item identifiers in addition to item ratings. Feedback data can also include non-pangenetic attribute descriptors that provide an indication of user behaviors, such as whether a link or ad was clicked on, whether an item was placed in a shopping cart or purchased by the user, or how long a user spent interacting with (i.e., dwelling on) a particular web based item. All of the above feedback data can be referred to collectively as 'item preferences'. Within this disclosure, the phrase 'item preferences' also refers to indications of item type, item category, item class, item manufacturer, item name, item brand, item model designation, item size, item shape, item color, item usage, an item feature, an item function, an item design, an item accessory, item price, item vendor, item return policy, item warranty, an item advertisement, an item promotion, a website, a webpage, a document, and a level of satisfaction with respect to any of the above.

In one embodiment, an item preference can, either implicitly or explicitly, provide an indication of the user's attitude, interest, opinion, relationship, or behavior toward the corresponding web based item. For example, an item preference can potentially be positive (e.g., long dwell time on webpage X), negative (e.g., short dwell time on webpage X) or neutral (e.g., average dwell time on webpage X). Alternatively, an item preference may provide no indication of the user's attitude, interest, opinion, relationship, or behavior toward the corresponding web based item, so that the item feedback table simply indicates the existence (or absence) of correlations between web items and users, or between web items and pangenetic data associated with users, without indicating the underlying basis of the correlations.

Initially an item preference or a query request for a particular item or type of item (category of item) can be received as input from the user or, alternatively, provided by the system from a stored dataset such as a non-pangenetic profile of the user or the user's saved shopping cart, for example. The system can then access a separate table, such as an item index or classification table, to identify a set of items that are similar or related to the item preference of the user (e.g., fall into the same item category). Information contained in the item table which enables identification of items that are similar/related as well as which items fit into particular categories can be implemented in the form of keys, references, pointers, associated data links, lists, or hashes. The relationships between items can be previously determined by a variety of methods, and can even be based on correlations and data collected by an item recommender system such as those disclosed herein. In one embodiment, an item feedback matrix can serve as an item index by containing keys, references, pointers, associated data links, lists, or hashes that indicate the identities of similar and related items and even which item classes or item categories they fall into. Once a set of items has been identified using either the item feedback matrix or a dedicated item index, those items can be looked up in the feedback matrix to retrieve corresponding ratings and correlated pangenetic attributes.

FIG. 2 illustrates one embodiment of an item feedback matrix that does not contain pangenetic data. An item feedback matrix can be implemented as a table, for example as a table in a relational database, or in other forms such as a part of search engine document index. In the example of FIG. 2, ratings provided by eight individuals for three different items are indicated, where the items can be web items, including webpages, items on webpages, or other internet content. While ratings are often selected from a range such as a scale of 1-5, for simplicity the rating choices in this example are limited to a binary system having the binary indicators {like, dislike}, which instead could have been the binary indicators {purchased, not purchased}, {saved, not saved}, {good, bad}, {satisfactory, unsatisfactory}, {would recommend, would not recommend}, {selected, not selected}, {clicked, not clicked}, {yes, no}, or {1, 0}, for example. A binary system can also be used to indicate either the existence of an association (e.g., a statistical association) or the absence of an association between an item and a user (or a user's pangenetic attributes) when storing correlation results in an item feedback matrix. Based on the available data in the matrix, which can be used to compute simple probabilities that can be converted to percentages, it can be predicted from the matrix that a user who likes item 1 would have a 0% chance of liking item 2 (computed as the number of individuals that like both item 1 and item 2 divided by the total number of individuals that like item 1, times 100%), and a 50% chance of liking item 3 (computed as the number of individuals that like both item 1 and item 3 divided by the total number of individuals that like item 1, times 100%). A user who likes item 2 would be predicted to have a 0% chance of liking item 1 and a 50% chance of liking item 3. Finally, a user that likes item 3 would have a 50% chance of liking item 1 and a 50% chance of liking item 2. In this example, there are many instances in which the prediction certainty is no better than random chance, in other words the chance outcome of dictated by flipping a coin. It should be noted that the feedback matrix illustrated in FIG. 2, as well as the feedback matrices of FIGS. 3, 4 and 5 which follow, are abstract representations of item feedback matrices. Item feedback matrices incorporated by the methods, systems, databases, and software disclosed herein may take a variety of forms in which data therein may be represented by descriptive or non-descriptive alphanumeric and non-alphanumeric identifiers, including cryptic and masked data representations and hashes. In one embodiment, item feedback matrices can also contain hypertext, hypertags, hyperlinks, and/or metadata (i.e., meta-tags, meta-text, meta descriptors, meta information).

FIG. 3 illustrates one embodiment of an item feedback matrix (i.e., table) in which user pangenetic data correlated with the items is revealed and replaces the user identifiers, thereby creating a pangenetic based item feedback matrix. As indicated in the figure, users can be clustered according to subcombinations of their pangenetic attributes which have been determined to correlate with particular item rating patterns. The first two rows associated with users 1 and 2 show that they are pangenetically similar, in this case pangenetically identical with respect to possession of two pangenetic attributes, a pair of SNPs having the designations Rs4961(T; T) and Rs5186(C;C), that have been correlated with a specific preference pattern for the three items. The 3rd and 4th individuals share a second preference pattern and the pangenetic attributes Rs3865418(T;C) and Rs6997709(G;G) that correlate with that pattern. The 5th and 6th share a third preference pattern and the pangenetic attributes Rs11110912(G;C) and Rs1937506(G;G) that correlate with that pattern. The 7th and 8th individuals share a fourth preference pattern and the pangenetic attributes Rs3755351(C;A) and Rs3794260(G;G) that correlate with that pattern. From the data of this pangenetic based item feedback matrix, which contains exactly the same feedback data as in the item feedback matrix of FIG. 2, it can be easily determined due to the inclusion of correlated pangenetic data in the matrix that a consumer who likes item 1 and possesses pangenetic attributes Rs4961(T;T) and Rs5186(C;C) is predicted to have a 0% chance of liking item 2 and a 100% chance of liking item 3. A consumer that likes item 1 and possesses pangenetic attributes Rs3755351(C;A) and Rs3794260(G;G) is predicted to have a 0% chance of liking either item 2 or item 3. A consumer that likes item 2 and possesses pangenetic attributes Rs3865418(T;C) and Rs6997709(G;G) is predicted to have a 0% chance of liking item 1 or item 2. A consumer that likes item 2 and possesses pangenetic attributes Rs11110912(G;C) and Rs1937506(G; G) is predicted to have a 0% chance of liking item 1 and a 100% chance of liking item 3. A consumer that likes item 3 and possesses pangenetic attributes Rs4961(T;T) and Rs5186 (C;C) is predicted to have a 100% chance of liking item 1 and a 0% chance of liking item 2. And finally, an individual that likes item 3 and possesses pangenetic attributes Rs11110912 (G;C) and Rs1937506(G;G) is predicted to have a 0% chance of liking item 1 and a 100% chance of liking item 2. Similar analyses can be made beginning based on beginning with dislikes.

The above predictions based on FIG. 3, which incorporate the comparison and clustering of individuals based on relevant pangenetic similarity, have a much higher degree of certainty, namely certainties of 0% or 100% (complete confidence that an equivalent user will not experience the indicated item preference or complete confidence that an equivalent user will experience the indicated item preference, respectively) as opposed to several instances of 50% certainty (random chance) in the circumstance illustrated in FIG. 2 in which pangenetic matching (i.e., filtering) is not utilized. In one embodiment the clusters referred to as pangenetic clusters can be more diverse so that both pangenetic attributes and non-pangenetic attributes, for example age and zip code, can help to characterize the clusters. In the various embodiments disclosed herein, a group of individuals or data records can be referred to as a cluster, subcluster, group, or subgroup, and when including pangenetic data can be referred to as a cluster, subcluster, group, subgroup, pangenetic cluster, pangenetic subcluster, pangenetic group, pangenetic subgroup, pangenetic based cluster, pangenetic based subcluster, pangenetic based group, or pangenetic based subgroup.

FIG. 4A illustrates one embodiment of a pangenetic based item feedback matrix containing feedback in the form of numerical ratings, where higher rating numbers indicate higher satisfaction levels. Various types of numerical rating scales can be potentially used, and for this example, a rating scale of 1 to 5 has been chosen where scores of 1 and 2 indicate two different levels of dissatisfaction, a score of 3 is neutral, and scores of 4 and 5 are two different levels of satisfaction (i.e., the scores 1, 2, 3, 4 and 5 can be interpreted as bad, poor, fair, good, and excellent, respectively). This particular rating system provides more information than the simple binary rating system presented in FIG. 3. Also, note that FIG. 3 represents an idealistic case in which the ratings by individuals within the same pangenetic cluster are identical with respect to the three items, so that a prediction made solely on the pangenetic attributes has the same level of certainty as a prediction which incorporates knowing both the pangenetic attributes of a user plus one or more of their past item preferences/ratings (e.g., knowing only that an individual possesses pangenetic attributes Rs4961(T;T) and Rs5186(C;C) yields the same prediction certainty of liking item 3 as knowing that an individual possesses pangenetic attributes Rs4961(T;T) and Rs5186(C;C) and likes item 1). In contrast to FIG. 3 however, FIG. 4A illustrates a more realistic scenario in which there is some variation between the item ratings by individuals grouped within the same pangenetic cluster. To increase the certainty of recommendations and predictions, rating records can be clustered as needed (and in real time) based on the rating patterns of only those items pertinent to the query. This can be accomplished by determining the similarity between sets of rating data (scoring data). This similarity can be quantified as degrees of similarity (i.e., levels of similarity) using quantitative similarity measures known to those of skill in the art including, but not limited to, percent identity, cosine similarity, Slope One (for non-binary data values), Hamming distance, Jaccard index (a.k.a., Jaccard similarity index), Jaccard distance, Levenshtein distance, and Dice's coefficient. One or more predetermined thresholds can be used to determine which individual rating records should be grouped into particular clusters. Predetermined thresholds that are appropriate for application to the results of these measures can be selected by the system or a user of the system based on the type of measure that was used for the comparison and the levels of either sensitivity and specificity or type I error (i.e., probability of making a false determination of dissimilarity or non-match) and type II error (i.e., probability of making a false determination of similarity or match) that are acceptable. A predetermined threshold can set the boundary between rating patterns (or pangenetic attribute combinations, as discussed below) that are considered to be similar and those that are considered to be dissimilar, or between those that are considered to be matching (i.e., equivalent) and those that are considered to be non-matching (i.e., non-equivalent). A predetermined threshold can comprise a quantitative value, qualitative value, conditional statement or conditional expression (e.g., if-then construct), and/or mathematical statement (e.g., equality statement, inequality statement) to indicate the actual value and boundary characteristic(s) of the threshold.

Once similar rating records have been clustered, pattern finding methods known to those of skill in the art can be used to determine correlations been each rating pattern and one or more combinations of pangenetic attributes. This approach creates the pangenetic clusters illustrated in FIG. 4A. FIG. 4B illustrates that, in one embodiment, the ratings for each pangenetic cluster can be averaged with respect to each item to produce average item rating values for each pangenetic cluster. A user can be matched to the most pangenetically similar cluster by comparing the user's pangenetic profile to the pangenetic attributes of each cluster to determine the degree of similarity with respect to each cluster. The degree of similarity between sets of pangenetic attributes can be quantified using any of several measures including, but not limited to, percent identity, Hamming distance, Jaccard index, Jaccard distance, Levenshtein distance, and Dice's coefficient. The magnitude of the similarity values (similarity scores) derived from a quantitative measure can be used to identify the most similar pangenetic cluster to the user based on the best score in a set (e.g., the largest percent identity, the smallest Hamming distance, the largest Jaccard index, the smallest Jaccard distance, the smallest Levenshtein distance, or the largest Dice's coefficient). Once a user's pangenetic profile has been matched to the most similar pangenetic cluster, the average rating values that were computed for that cluster can be transmitted as the predicted levels of satisfaction that the user is most likely to experience with the respective items. Alternatively, the user's pangenetic profile can be considered to be a match for all clusters whose similarity scores exceed a predetermined threshold and the rating values (or average rating values) for those clusters averaged and then transmitted as the predicted levels of satisfaction that the user is most likely to experience with the respective items. Generally, pangenetic similarity measures are based on the numerical quantity of pangenetic matches determined by performing comparisons of pangenetic data.

FIG. 5A illustrates one embodiment of a pangenetic based item feedback matrix which contains numerical ratings similar to FIG. 4A. The purpose of this figure is to illustrate that, while a group of users can be clustered based on a particular combination of pangenetic attributes that correlate with a particular rating pattern, there can be enough variation within a pangenetic cluster to allow subgrouping (subclustering) individuals that share more similar rating patterns than others within a particular pangenetic cluster. By identifying a subgroup of individuals that are even more similar to a future consumer with respect to item preferences than the entire group of individuals comprising the pangenetic cluster, significantly more certain and accurate predictions can be made for the user. To illustrate this approach, FIG. 5A contains rating records corresponding to four individuals in a pangenetic cluster 1, and another four individuals in a pangenetic cluster 2. As can be seen from FIG. 5A, the ratings in pangenetic cluster 1 predominantly indicate satisfaction with items 1 and 3 and dissatisfaction for item 2, and this overall rating patter is associated with the pair of pangenetic SNP attributes Rs4961(T;T) and Rs5186(C;C). In contrast, the ratings in pangenetic cluster 2 predominantly indicate satisfaction with item 2 and dissatisfaction with items 1 and 3, and this rating pattern is associated with a different pair of pangenetic SNP attributes Rs11110912(G;C) and Rs1937506(G;G). Analyzing the ratings data more closely for more subtle variations using similarity measures, it can be determined that the four records of pangenetic cluster 1 can be partitioned into two subgroups. With respect to pangenetic cluster 1, the subcluster labeled 'subgroup 1' shows higher satisfaction with item 1 than the subcluster labeled 'subgroup 2', as can be clearly seen from the average subgroup ratings presented in FIG. 5B. Subgroup 1 and subgroup 2 both show high dissatisfaction with item 2. However, subgroup 1 shows neutrality toward item 3 while subgroup 2 shows satisfaction with item 3. Similarly, it can be determined that the four records of pangenetic cluster 2 can be partitioned into two subgroups. As shown in FIG. 5B, subgroup 1 and subgroup 2 of pangenetic cluster 2 are differentiated by moderate variations in their rating values, particularly with respect to item 3 where subgroup 1 is neutral and subgroup 2 is highly dissatisfied.

Similar individuals share greater similarity of preferences and opinions (i.e., ratings) with respect to particular items as well as a higher degree of similarity at the pangenetic level, and a comparison of a new user's pangenetic attributes and previous item ratings with those of each of the clusters contained in the feedback matrix can be performed to identify the particular cluster that is most similar to the new user and will provide the greatest accuracy and certainty in predicting their preferences and satisfaction with other items. It should be noted that determination of clusters (subgroups) can be performed in steps, each step involving either clustering based on rating similarities or clustering based on pangenetic similarities. Each step refines the results, creating clusters that are more homogeneous with respect to the individual records they contain. And the order of the clustering steps can be varied when involving selection based on pangenetics versus selection based on item rating patterns, so as to either place priority on creating clusters having greater internal pangenetic similarity, or alternatively, creating clusters having greater internal item ratings similarity. For example, as described in the example with respect to FIGS. 5A and 5B, the process can begin with a first round of clustering based on similarity of item preference (e.g., rating) patterns, then a second round of clustering based on pangenetic similarity, and if desired, a third round of clustering based on items preference patterns. Alternatively, clustering can begin with a first round of clustering based on pangenetic similarity, then one or more additional rounds of clustering based on similarity of item preference patterns.

The approaches described herein enable greater certainty in making predictions about what items users will prefer in the future by forming clusters of similar individuals from which to derive those predictions, the clustering being based on pangenetic similarities as well as previous item preference/rating similarities. With respect to predicting satisfaction with products and services offered online, this enables both item-centric and user-centric approaches for application to item selection, rating and recommendation for a user (e.g., a consumer). An item-centric approach predicts a user's level of satisfaction with a particular item that the user indicated. A user-centric approach recommends, based on a first item indicated by the user, additional items that are likely to satisfy the user.

An item-centric method of web based item rating and recommendation relies on selection of a specific product by a user, either directly through a keyword query input, selection from a product listing, or through a series of dropdown menus (i.e., pull-down menus) which guide the user to select a particular product. Based at least in part on a comparison of the user's relevant pangenetic attributes with those of other users that have provided feedback directly or indirectly for the item, the system can predict 1) the level of satisfaction the user will experience with the item, and 2) the probability or likelihood that the user will achieve that level of satisfaction. More specifically, the system receives at least one item preference of the user and accesses their pangenetic profile (i.e., pangenetic data associated with the user). The system can then access a dataset (e.g., a feedback matrix dataset) containing one or more satisfaction levels associated with the item along with pangenetic data corresponding to each of the one or more satisfaction levels, where the pangenetic data is derived from a plurality of consumers that indicated their level of satisfaction with the item (e.g., relevant pangenetic attributes of consumers that aggregate (co-occur) with a high level of satisfaction are linked in association with that level of satisfaction in a pangenetic based item feedback matrix). A comparison is performed between the pangenetic profile of the user and the pangenetic data corresponding to each of the one or more satisfaction levels (e.g., contained within the pangenetic based item feedback matrix). To determine the level of satisfaction that the user will most likely experience with the item, probabilities for each of the satisfaction levels can be computed and the satisfaction level corresponding to the highest probability can be selected. For example, past users sharing relevant pangenetic attributes with the user are identified then partitioned into clusters containing users who experienced a particular satisfaction level with the item, one cluster for each possible satisfaction level. To compute each of the probabilities, the numerical count of users in a particular satisfaction level cluster are divided by the total number of pangenetically matched users (i.e., the sum of all individuals in all satisfaction level groups associated with the set of relevant pangenetic attributes). At an extreme where only a single satisfaction level is correlated with the relevant pangenetic attributes, the probability that the user will also experience that level of satisfaction with the item will be 1.0 (i.e., 100% chance). The system can transmit an indication that the user will have a 100% chance of experiencing that satisfaction level. In most cases due to real world variability, there will likely be two or more possible satisfaction levels that the user may experience. In those cases, the system can transmit output indicating that the user will experience the satisfaction level corresponding with the highest probability, along with that numerical probability or another useful statistical measure result that provides an indication of the degree of certainty of that outcome. In another embodiment, a plurality of satisfaction levels can be output along with numerical probabilities or other statistical measure results that provide an indication of the degree of certainty of each of those potential outcomes. The output can be transmitted to at least one destination selected from the group consisting of a user, a database, a dataset, a computer readable memory, a computer readable medium, a computer processor, a computer network, a printout device, a visual display, and a wireless receiver.

A user-centric method of web based item recommendation relies on specification of a product, product class or product category by a user (e.g., consumer), either directly through a keyword query input, a recommendation from a social network or traditional recommender system, selection from a product listing, or selection from a series of dropdown menus (i.e., pull-down menus) which guide the user to make the selection. Based at least in part on a comparison of the user's relevant pangenetic attributes against those of other users that have provided direct or indirect feedback for items similar to the one indicated by the user, the system can 1) identify one or more specific items for consideration by the user, and 2) indicate the likely satisfaction level that the user will experience with each item as well as the associated probabilities, likelihoods, or percent chance that the user will achieve those satisfaction levels. An example of a suitable application for a user-centric item recommendation system is recommendation of music earphones as disclosed previously.

Another exemplary application is a web based restaurant recommendation guide which provides personalized restaurant recommendations based on, for example, both a user's query for a certain type of cuisine (e.g., Chinese, Cuban, French, Italian, Mexican, etc.) and their pangenetic attributes which inherently determine their preferences for certain tastes and smells that at least partially dictate the overall experience that an individual has at a restaurant. The feedback that users provide can even be linked in association with specific dishes on the menus of those restaurants to further refine the recommendation system. By incorporating or interfacing with a social network system that permits the feedback and recommendation system to access the pangenetic profiles of friends and acquaintances, a pangenetic based online restaurant guide can be enabled that is capable of making restaurant recommendations based on the pangenetic traits of all of the individuals in a dining party, thereby arriving at a restaurant recommendation that will best satisfy the innate preferences of all of the members of that party. In one embodiment, the system can accomplish this task by first accessing a pangenetics-item feedback matrix for restaurant and food preferences in order to identify corresponding pangenetic attributes that are relevant to restaurant and food preferences. The system can then access the pangenetic profiles of the individuals of the dining party to derive a consensus set of pangenetic attributes constituting the intersection of relevant pangenetic attributes for restaurant and food preferences that are shared among the individuals in the dining party. The pangenetic consensus set of attributes for the dining party is then compared with the pangenetic based item feedback matrix to identify the restaurant having associated pangenetic data that best matches the pangenetic consensus of the dining party, thereby resulting in recommendation of a restaurant that will best satisfy the dining party as a whole. Essentially the same approach can be used in the online selection and/or recommendation of numerous products and services including, but not limited to, alcoholic beverages, music, movies, vacation packages, hobbies and gift selection.

In one embodiment of a user-centric approach to web based item recommendation, the specific items identified for the user can include just the best choices, or a full range of choices including those identified as inappropriate for the user. By indicating corresponding satisfaction levels to the user and delineating good, average, and poor choices from each other, a user can clearly and quickly see what items will best meet their needs and which will not. Further groupings can be created based on such parameters as price, availability, and retailer rating/reliability. More specifically, a user-centric system receives at least one item preference of the user and accesses the pangenetic profile of the user (i.e., pangenetic data associated with the user). The system then accesses a dataset (e.g., an item feedback matrix dataset) containing a plurality of items matching the at least one item preference of the user, for example, a variety of brands and models of items falling within the broader item category indicated directly or indirectly by the user. Each of the plurality of items can be associated with (correlated with) pangenetic data derived from previous users that had experience with the items (e.g., pangenetic data correlating with good experiences and/or opinions of each of the items). The system performs a comparison between the pangenetic profile of the user and the pangenetic data corresponding to each of the plurality of items (contained within the pangenetic based item feedback matrix) to identify pangenetic matches. Particular items associated with pangenetic data that best matches the pangenetic data of the user can be transmitted as output, and can include associated probable satisfaction levels. The items can be ordered or ranked based on degree of pangenetic match and/or the relative magnitudes of the associated satisfaction levels. If one or more of the associated satisfaction levels indicate average or poor satisfaction, for example, the items corresponding to those lower satisfaction levels can be delineated from items predicted to provide high levels of satisfaction using visual or localization cues, such as different locations on a SERP, different coloration, highlighting, or symbols (i.e., markers) such as icons or flags. The output can be transmitted to at least one destination selected from the group consisting of a user, a database, a dataset, a computer readable memory, a computer readable medium, a computer processor, a computer network, a printout device, a visual display, and a wireless receiver.

In addition to being used for providing item recommendations to users, the disclosed inventions can also be used to predict which online offerings (i.e., webpage items) a user will ultimately choose to interact with or purchase. As such, the methods, systems, databases and software of the instant disclosure can be used for generating predictions of user behavior and user purchases. As previously described, the items represented in a user based item feedback matrix such as that of FIG. 2, or a pangenetics based item feedback matrix such as that of FIG. 3, can be internet based (internet accessible) items such as webpages, webpage links, and webpage offerings including advertisements, products, services and information content, for example. Additionally, the items in an item feedback matrix can be behavioral descriptors that indicate item preferences in the form of behaviors, both historical and predicted, that a user can exhibit toward an item. The behavioral data contained in a behavioral item feedback matrix can be used to predict a user's series of actions with respect to one or more items, based on an initial reaction to presentation of a first item. For example, if an individual is presented with a web item, the system can monitor the user's response to the presented web item. The user can exhibit many possible responses, such as clicking on the item, reading about the item, clicking on additional links to evaluate the specifications, availability, and options associated with the item, spending a particular amount of time evaluating information about the item, placing the item in a shopping cart, saving the item for later, forwarding the item to a friend, or any of several other responses, including no response. If the user responds by dwelling on the item for a key period of time and then saving the item for later, the system can utilize a behavioral item feedback matrix to predict, based on this initial response and the user's pangenetic makeup, the probability that the user will eventually buy the item, the probability that they will ultimately never purchase the item given that they saved it for later rather than purchasing it now, the probability that the user would respond to a web coupon offer that increases the desirability of the item as opposed to presentation of entirely new item choices, and so on. By using the behavioral item feedback matrix to predict the user's reactions and future behaviors, the system can determine, for example, that this particular user will be induced to purchase the current item if immediately presented with a short-lived coupon which discounts the price of the item (or some other reward determined to achieve the desired purchasing behavior of this user with a high level of certainty). This approach offers a distinct advantage over a system which, for example, makes no attempt to entice the user to purchase until they exhibit a terminal behavior such as navigating away from the item or the website entirely.

When passive data gathering is used to collect data for a behavioral item feedback matrix—wherein passive data gathering entails monitoring users' online behavior to track and record what each user clicks on, opens, reads, plays, views, prints, purchases, recommends, and shares online through the internet—and that data is then correlated with users' pangenetic attributes, a number of different types of predictions can be made about pangenetically similar users including their likelihood of visiting a particular webpage; likelihood of clicking on a hyperlink on a particular webpage; likelihood of clicking on an advertisement on a particular webpage; likelihood of drilling deeper into a website from a landing webpage; likelihood of interacting with audio or video content on a webpage; likelihood of purchasing a product or service offered by a webpage; and likelihood of recommending or forwarding an online offering to someone else. While the term likelihood is used, a variety of statistical association measures can be used for determining level (degree) of certainty or strength of association values including, but not limited to, probability (a.k.a. absolute risk), relative risk, odds (a.k.a. likelihood), and odds ratio (a.k.a. likelihood ratio). Statistical significance of values computed for statistical associations can also be obtained using other statistical measures such as standard error, standard deviation and confidence intervals. Predetermined threshold values can be applied to any of the above in order to limit correlations stored in an item feedback matrix to those that are deemed to have an acceptable or high degree of strength, certainty, and/or statistical significance. Additionally, mathematical measures such as the cosine similarity measure, linear regression and slope one regression can be used to identify the most appropriate items to recommend to an individual based on data contained in a behavioral item feedback matrix (i.e., an item feedback matrix).

Items that are predicted to be of interest to an individual based on the results of one or more of the recommender methods disclosed herein can be used as the basis for going back and selecting pangenetic attributes from the item feedback matrix (those that are correlated with the items of interest), and then associating (linking) those pangenetic attributes with webpages that contain one or more of the items of interest. In one embodiment, correlations between item preferences and pangenetic attributes from an item feedback matrix can be used as the basis for selecting pangenetic attributes for incorporation into web based search indexes and hitlists containing entries that point to webpages containing the items of interest. In one embodiment, a personalized webpage search index can be generated for a user in real time or near real time, upon receiving a user query, by using data and/or results derived from an item feedback matrix. This approach, when conducted with the most recent data available for the current user as well as previous users whose behaviors and preferences comprise the item feedback matrix, has the potential to provide the most relevant and targeted web search results for the current user. As a result, recent trends that cause shifts in correlations between pangenetic makeup and web content can be rapidly detected, predicted and incorporated into personalized webpage searches to generate up-to-date search results having the highest relevance for the user.

One approach for determining pangenetic attributes that correlate (i.e., co-associate, co-occur) with particular web based items, item ratings, and online user behaviors to generate an item feedback matrix can initially involve determining the intersection of pangenetic attributes for every possible combination of pangenetic profiles that can be formed from a set of pangenetic profiles. Briefly, this method requires forming all possible 2-tuple combinations of pangenetic profiles from the set of pangenetic profiles and comparing the pangenetic profiles within each 2-tuple. The largest combination of attributes that occurs within both pangenetic profiles of each 2-tuple is identified and stored as the largest pangenetic attribute combination co-occurring in that 2-tuple. Next, all possible 3-tuple combinations of the pangenetic profiles are formed. For each 3-tuple, the largest pangenetic attribute combination occurring within all three pangenetic profiles of that 3-tuple is identified and stored as the largest pangenetic attribute combination co-occurring in that 3-tuple. Next 4-tuples are formed and the largest co-occurring pangenetic attribute combination within each 4-tuple identified. This approach is repeated for progressively larger tuples by simply increasing the n-tuple size by one at each step. Computational burden can be reduced in part by incorporating a requirement that prevents the formation of any (n+1)-tuple combination from an n-tuple combination for which no co-occurring pangenetic attribute combination was identified. With this requirement, the identification of pangenetic combinations is terminated at the point when every n-tuple generated at a particular step is null for possession of at least one co-occurring pangenetic attribute combination (i.e., not one of the newly generated n-tuple combinations contains pangenetic profiles which share at least pangenetic attribute combination in common).

The shortcomings of the immediately previous method are two-fold. The first shortcoming relates to the very large number of pangenetic comparisons that may be required in the initial step alone. For example, when comparing 1,000 pangenetic profiles comprising 1 million SNPs per pangenetic profile, $5 \times 10^{11}$ individual pangenetic attribute comparisons are required just for the initial step of comparing all possible pairs of the 1,000 pangenetic profiles (($5 \times 10^5$ possible pairings of pangenetic profiles)×($10^6$ attributes per pangenetic profile)=$5 \times 10^{11}$ individual pangenetic attribute comparisons). If each pangenetic profile contained the full complement of 3 billion nucleotides of whole genomic sequence, then $1.5 \times 10^{15}$ individual pangenetic attribute comparisons would be required in the first step of comparing all possible pairs of pangenetic profiles, resulting in a computationally intensive method requiring a supercomputer. The second shortcoming of this particular method is that it only identifies the largest pangenetic combination that is shared within each n-tuple combination of pangenetic profiles. The method does not enable identification of smaller pangenetic combinations, contained within each largest identified pangenetic combination, which may be responsible for the bulk of the strength of association between the larger pangenetic combinations and an indicated item preference of a user. A smaller pangenetic combination would not be identified by this particular method unless there is at least one individual that possesses only that smaller pangenetic combination in their pangenetic profile without having any of the other attributes that are present in the larger pangenetic combination. The above shortcomings limit the usefulness of this approach for determining pangenetic attribute combinations associated with one or more non-pangenetic attributes and make it a nonpreferred method.

It is therefore desirable that a method for determining combinations of pangenetic attributes that correlate with particular items or items ratings be able to identify not only the largest pangenetic combinations shared by pangenetic profiles, but also smaller pangenetic combinations as well, to determine the smallest and most strongly associated core pangenetic combinations that co-associate with a particular item, item rating, or item rating pattern (i.e., item preferences). A core pangenetic combination can, for example, be defined as the smallest subset of attributes having a statistically significant association with one of those entities. An alternative definition of a core pangenetic combination can be the smallest subset of pangenetic attributes that confers an absolute risk of association above a predetermined threshold. Other definitions of a core pangenetic combination can be formulated, for example, based on needs arising from user implementation, population and sample sizes, statistical constraints, or available computing power. Identification of this core pangenetic combination and its pangenetic attribute content is of great importance because a core pangenetic combination should contain pangenetic attributes that directly correlate with (i.e., are strongly associated with) a particular preference or rating pattern for one or more items.

In one embodiment of a computationally efficient method for determining combinations of pangenetic attributes that correlate with particular items, item ratings, or online user behaviors, the pangenetic attribute combinations are identified without the need for supercomputing, even when evaluating populations comprising millions of individuals and pangenetic profiles each comprising billions of attributes. To help reduce computational burden, a representative subset of pangenetic profiles can be selected from a larger set of profiles. The representative subset of pangenetic profiles can be used to identify candidate pangenetic attribute combinations associated with an item or item rating pattern much more efficiently when the full set of pangenetic profiles being considered is large (e.g., thousands or millions of pangenetic profiles). The selection of a subset of pangenetic profiles can be a random selection or another appropriate and/or statistically valid method of selection. The size of this subset can vary, but for example, can comprise as few as 10 or as many as 100 or more pangenetic profiles. There may be several different core pangenetic attribute combinations associated with a particular item preference or rating pattern for a group of items, for example. In a case where three or fewer core pangenetic attribute combinations are expected to be associated with an item or item rating pattern, as few as 10 randomly pangenetic profiles may enable the identification of those pangenetic attribute combinations. If it is expected that more than three core pangenetic attribute combinations are associated with an item or item rating pattern, then selecting a higher number of pangenetic profiles for the subset may be advisable.

In one embodiment of a computationally efficient method for determining pangenetic attribute combinations that correlate with a particular item preference, a beneficial step involves eliminating from consideration those pangenetic attributes which show association with both satisfaction and dissatisfaction for the item, and therefore cannot specifically correlate with item satisfaction over item dissatisfaction. This can be accomplished by comparing a subset of pangenetic profiles associated with item satisfaction to an appropriately selected (e.g., randomly selected) subset of pangenetic profiles associated with item dissatisfaction to eliminate pangenetic attributes that co-occur at a high frequency in association with item dissatisfaction (at a frequency of 80% or greater, for example) and are therefore unlikely to have a direct positive correlation with the desired item or rating pattern. Failure to eliminate these pangenetic attributes may add complexity to a pangenetic attribute combination without increasing its strength of correlation with the desired item or rating pattern, thereby reducing the certainty and accuracy of predictions and recommendations that are based on those pangenetic attribute combinations. It is therefore advantageous to eliminate these pangenetic attributes in an initial step so that the core pangenetic attribute combinations can be determined as quickly, efficiently and accurately as possible. While not absolutely required, this approach greatly increases efficiency when comparing numerous pangenetic profiles each containing large numbers of attributes, as for example when processing whole genomic attribute profiles of a large population where each pangenetic profile can contain 6 billion nucleotide attributes which on average will be 99.9% identical between any given pair of individuals. The subset of pangenetic attributes identified by this approach can be referred to as a set of candidate pangenetic attributes. A set of candidate pangenetic attributes can be further processed to identify combinations of the candidate pangenetic attributes that correlate with the item or rating pattern of interest as described below.

In a further embodiment of a computationally efficient method for compiling co-associating attributes, a divide-and-conquer approach can be used to greatly increase the efficiency of identifying pangenetic attribute combinations that are associated with an item preference. This approach partitions (i.e., subdivides, divides, or segments) a set of pangenetic profiles into subsets of pangenetic profiles, each subset comprising those pangenetic profiles that share the most pangenetic attributes in common. Each iteration of the divide-and-conquer approach partitions the set (or subset) of pangenetic profiles associated with the item preference of interest into at least two subsets, and multiple iterations can be used to generate additional subsets. The pangenetic profiles that comprise each subset are evaluated to identify the largest pangenetic attribute combination that they share in common. Initially a first pangenetic profile is selected from the set of pangenetic profiles associated with the item preference of interest. As an example using a set of 10 pangenetic profiles, a first pangenetic profile is selected from the set of 10 pangenetic profiles. This first pangenetic profile, pangenetic profile #1, can then be used in a series of pairwise comparisons with each of the other pangenetic profiles in the set. In a preferred embodiment, all possible pairwise comparisons of the first pangenetic profile with the other pangenetic profiles are performed. In this example, the possible pairings are {#1, #2}, {#1, #3}, {#1, #4}, {#1, #5}, {#1, #6}, {#1, #7}, {#1, #8}, {#1, #9}, and {#1, #10}, for a total of nine pairwise pangenetic profile comparisons. If each of the 10 individuals has an associated pangenetic profile consisting of $10^6$ pangenetic attributes, then this example would require performing $9 \times 10^6$ individual attribute comparisons (9 paired pangenetic profiles $\times 10^6$ attributes per pangenetic profile). Sets of attributes (i.e., pangenetic attribute combinations) constituting the intersection in content between the two pangenetic profiles of each pairwise comparison can be stored to generate a first set of pangenetic attribute combinations, wherein each pangenetic attribute combination can be stored in association with the pair of pangenetic profiles from which it was generated. The largest pangenetic attribute combination occurring in the first set of pangenetic attribute combinations can be identified and referred to as the primary pangenetic attribute combination. As an example, if the largest intersection of attributes occurs in the paired comparison {#1, #4}, then this intersection produces the primary pangenetic attribute combination for the set of pangenetic profiles #1-#10 under consideration. This primary pangenetic attribute combination can serve as the basis for partitioning the set of pangenetic profiles into subsets of pangenetic profiles, one of which can include pangenetic profiles that are most similar to #1 and #4. This is achieved by using the primary pangenetic attribute combination in a series of pairwise comparisons with each of the other pangenetic attribute combinations previously stored in the first set of pangenetic attribute combinations. Sets of attributes constituting the intersection in content between the two pangenetic attribute combinations of each pairwise comparison are stored to generate a second set of pangenetic attribute combinations, wherein each pangenetic attribute combination is stored in association with the three corresponding pangenetic profiles from it was generated. Continuing from the example above, by using the primary pangenetic attribute combination corresponding to {#1, #4} in pairwise comparisons with each of the other pangenetic attribute combinations in the first set corresponding to {#1, #2}, {#1, #3}, {#1, #5}, {#1, #6}, {#1, #7}, {#1, #8}, {#1, #9}, and {#1, #10}, the resulting eight intersections of attributes corresponding to the triplets of pangenetic profiles {#1, #2, #4}, {#1, #3, #4}, {#1, #4, #5}, {#1, #4, #6}, {#1, #4, #7}, {#1, #4, #8}, {#1, #4, #9}, and {#1, #4, #10} can be stored as a second set of pangenetic attribute combinations. The set of 10 pangenetic profiles can then be divided (i.e., partitioned) into at least two pangenetic profile subsets based on the sizes of the pangenetic attribute combinations in the second set as compared with the size of the primary pangenetic attribute combination. More specifically, the pangenetic profiles which correspond to pangenetic attribute combinations in the second set of pangenetic attribute combinations that are equal to or larger than a predetermined fraction of the size of the primary pangenetic attribute combination, for example those that are at least 50% of the size of the primary pangenetic attribute combination, can be assigned to a first subset of pangenetic profiles, while the pangenetic profiles corresponding to the remaining pangenetic attribute combinations which are less than the predetermined fraction of the size of the primary pangenetic attribute combination, for example those that are less than 50% of the size of the primary pangenetic attribute combination, can be assigned to a second subset of pangenetic profiles. By doing this, the pangenetic profiles that are most similar to the two pangenetic profiles which generated the primary pangenetic attribute combination in the current iteration are clustered together into the first subset of pangenetic profiles. The choice of 50% as the predetermined fraction of the size of the primary pangenetic attribute combination is arbitrary in these examples, and can be adjusted higher or lower to respectively increase or decrease the degree of similarity desired of pangenetic profiles that are partitioned into a subset. As such, the predetermined fraction of the size of the primary pangenetic attribute combination essentially acts as a stringency parameter for including and excluding pangenetic profiles from the subsets, and it can have substantial influence on the number of attributes profiles partitioned into each subset, as well as the number of subsets that will ultimately be formed.

Continuing with the above example in which the primary pangenetic attribute combination derived from comparison of pangenetic profiles #1 and #4, the first subset will include pangenetic profiles #1 and #4 as well as any other pangenetic profiles that correspond with pangenetic attribute combinations in the second set that are at least 50% of the size of that primary pangenetic attribute combination. For this example, assume that pangenetic profile triplets {#1, #4, #6} and {#1, #4, #9} are associated with pangenetic attribute combinations in the second set that are equal to or greater than 50% of the size of the primary pangenetic attribute combination. Pangenetic profiles #6 and #9 would therefore be included in the first subset of pangenetic profiles along with pangenetic profiles #1 and #4 (first subset={#1, #4, #6, #9}). Pangenetic profiles #2, #3, #5, #7, #8, and #10 on the other hand are assigned to the second subset because they each share less than 50% of the attributes in common with the primary pangenetic attribute combination. The above is illustrated graphically in FIG. 6, where the primary pangenetic attribute combination is indicated to contain 100 pangenetic attributes and those pangenetic profiles in the second subset each share less than 50 pangenetic attributes in common with that primary attribute combination. The largest pangenetic attribute combination shared by the pangenetic profiles of the first subset {#1, #4, #6, #9} should then be stored as a candidate pangenetic attribute combination in a set of candidate pangenetic attribute combinations.

The pangenetic profiles in the second subset can then be processed through a reiteration of the method, where the second subset can be redesignated as the subset of pangenetic profiles, a new first pangenetic profile can be selected from this subset of pangenetic profiles, a new first set of pangenetic attribute combinations can be generated from pairwise comparison of the first pangenetic profile with the other pangenetic profiles of this subset, a new primary pangenetic attribute combination can be determined, a new second set of pangenetic attribute combinations can be generated from the pairwise comparison of the primary pangenetic attribute combination with the other pangenetic attribute combinations in the first set of pangenetic attribute combinations, and the current subset of pangenetic profiles can be divided into a new first subset and a new second subset based on the comparison of each of the pangenetic attribute combinations in the second set with the primary pangenetic attribute combination. The largest pangenetic attribute combination occurring in all the pangenetic profiles of the new first subset can be stored as a candidate pangenetic attribute combination in the set of candidate pangenetic attribute combinations. Reiteration can continue in this manner, beginning with the current second subset redesignated as the subset of pangenetic profiles, until an iteration is reached where a new second subset containing one or more pangenetic profiles cannot be formed (i.e., the new second subset formed is an empty/null set).

To exemplify this reiteration process continuing with the pangenetic profiles from the above example, the second subset comprising pangenetic profiles #2, #3, #5, #7, #8, and #10 is redesignated as the subset of pangenetic profiles, and pangenetic profile #2 can be selected as a first pangenetic profile for this subset. The selected pangenetic profile #2 is then used to determine the attribute intersections of the five pairwise pangenetic profile comparisons corresponding to {#2, #3}, {#2, #5}, {#2, #7}, {#2, #8}, and {#2, #10}. Assuming pangenetic profiles #5 and #10 are found to cluster with pangenetic profile #2 as a result of evaluating the intersection in attribute content of the pairwise comparisons as described above, partition of this subset of pangenetic profiles creates a new first subset containing pangenetic profiles #2, #5 and #10, and a new second subset containing pangenetic profiles #3, #7, and #8. The largest pangenetic attribute combination corresponding to the intersection of pangenetic profiles #2, #5 and #10 is stored as a candidate pangenetic attribute combination in the set of candidate pangenetic attribute combinations. Reiterative processing of the second subset comprising pangenetic profiles #3, #7 and #8 proceeds with pangenetic profile #3 selected as the first pangenetic profile, which is then used to perform the two pairwise comparisons {#3, #7} and {#3, #8}. Assuming a comparison finds these three pangenetic profiles to cluster together, no new second subset can be generated. The largest pangenetic attribute combination corresponding to the intersection of pangenetic profiles #3, #7 and #8 is stored as a candidate pangenetic attribute combination in the set of candidate pangenetic attribute combinations. Frequencies of occurrence of each of the candidate pangenetic attribute combinations that were generated and stored in the set of candidate pangenetic attribute combinations can be determined for a set of pangenetic profiles associated with a particular item preference (i.e., a query-attribute-positive set) and in a set of pangenetic profiles that are not associated with a particular item preference (i.e., a query-attribute-negative set) so that strength of association of the candidate pangenetic attribute combinations with the item preference (i.e., the query attribute) can be determined and used as desired for other methods.

By clustering the pangenetic profiles into subsets, the divide-and-conquer approach substantially increases efficiency because no comparisons of pangenetic profiles are performed across subsets. Consequently, the number of pangenetic profile comparisons required by the divide-and-conquer approach is much less than that required by just the first step of the nonpreferred method described previously which compares all possible combinations of pangenetic profiles that can be formed from a set of pangenetic profiles. To demonstrate this, consider again the above example which used the divide-and-conquer approach to partition a set of 10 pangenetic profiles into three nearly equally sized subsets of pangenetic profiles to generate three candidate pangenetic attribute combinations. That example required a total of 16 pairwise comparisons of pangenetic profiles over three iterations (9+5+2=16). In contrast, the nonpreferred method would require 45 pairwise comparisons of pangenetic profiles in its first step (10 choose 2=45). When processing a much larger set, for example a set of 1,000 pangenetic profiles, the divide-and-conquer approach would require 1,996 pairwise pangenetic profile comparisons in a scenario in which the 1,000 pangenetic profiles cluster into three nearly equally sized subsets of pangenetic profiles (999+665+332=1,996), while the nonpreferred method would require 499,500 pairwise comparisons in its first step (1,000 choose 2=499,500). Therefore, as the number of pangenetic profiles in the initial set increases, the computational burden of the divide-and-conquer approach increases linearly, while the computational burden of the nonpreferred method increases exponentially. This represents a tremendous advantage in computational efficiency of the divide-and-conquer approach. While methods for determining co-occurring attribute combinations are primarily described herein with respect to pangenetic attributes and pangenetic profiles, they equally apply to non-pangenetic attributes and non-pangenetic attribute profiles, as well as attribute profiles that contain both non-pangenetic attributes and pangenetic attributes.

In one embodiment, a plurality of sets of attributes (e.g., pangenetic profiles) are evaluated and clustered into subsets according to the divide-and-conquer approach described herein, wherein the subsets formed can be mapped to a first half and second half of the plurality of sets of attributes by clustering the two most similar attribute sets with other attribute sets that are highly similar to those two. Alternatively, other clustering methods which look for similarities and which provide a basis for aggregation of attributes can be used (e.g., seeding). In one embodiment all attributes are given binary values (present or not present) and the clustering is performed based on the presence of combinations of attributes within the group of pangenetic profiles associated with the item preference specified. In an alternate embodiment some attributes are continuous or multi-valued (e.g. obesity) and described on a continuous value or discrete multi-valued basis. A number of clustering algorithms, including but not limited to K-means clustering, as well as determination of similarity measures including geometric distance or angles can be used to determine one or more of the subsets. Additionally, seeding techniques can be used to generate subsets, for example by requiring that one or more pangenetic profiles that nucleate formation of one or more subsets contain a minimal specified or predetermined set of attributes (i.e., a core pangenetic attribute combination). In one embodiment, if a particular attribute or set of attributes is known to be causally associated with a particular outcome (i.e., an item preference), that attribute or set of attributes can be used as the basis for clustering attributes, pangenetic profiles, and/or individuals into subsets (clusters).

Each candidate pangenetic attribute combination generated by the divide-and-conquer approach constitutes the largest combination of attributes occurring within all of the pangenetic profiles of a particular subset of pangenetic profiles. As explained previously, the largest pangenetic attribute combination identified may contain smaller combinations of attributes (i.e., core pangenetic attribute combinations) that also co-associate with specified item preference. A further embodiment of a computationally efficient method for compiling co-associating attributes is able to identify core pangenetic attribute combinations, contained within a larger candidate pangenetic attribute combination for example, using a top-down approach. These smaller core pangenetic attribute combinations, by virtue of the way in which they are identified, can contain attributes which are the most essential attributes for contributing to co-association with the item preference. Candidate pangenetic attribute combinations determined by the divide-and-conquer approach are preferably used as the starting point for identifying core pangenetic attribute combinations. The following top-down approach to identifying a core pangenetic attribute combination begins with generating subcombinations of attributes selected from a candidate pangenetic attribute combination, the number of attributes in each subcombination being less than that of the candidate pangenetic attribute combination. In one embodiment, the number of attributes in each attribute subcombination is one less than the candidate pangenetic attribute combination from which the attributes are selected. In a further embodiment, all possible attribute subcombinations containing one less attribute than the candidate pangenetic attribute combination are generated, so that for every attribute comprising the candidate pangenetic attribute combination there will be exactly one attribute subcombination generated which lacks that attribute. The frequencies of occurrence of each of the candidate pangenetic attribute combinations and attribute subcombinations can be determined in the set of pangenetic profiles associated with the specified item preference (i.e., the query-attribute-positive group) and in the set of pangenetic profiles that are not associated with specified item preference (i.e., the query-attribute-negative group), and based on the frequencies of occurrence, each subcombination having a lower strength of association with the specified item preference than the candidate pangenetic attribute combination from which it was generated is identified. A lower strength of association would be expected to result from an increased frequency of occurrence, in the query-attribute-negative set of pangenetic profiles, of the attribute subcombination relative to the candidate pangenetic attribute combination from which it was generated. Because each attribute subcombination is missing at least one attribute relative to the candidate pangenetic attribute combination from which it was generated, a missing attribute can be readily identified as a core attribute responsible for the lower strength of association since it constitutes the only difference between the attribute subcombination and the candidate pangenetic attribute combination. By evaluating all of the attribute subcombinations that are generated from a particular candidate pangenetic attribute combination with respect to strength of association with the specified item preference as above, a set of attributes constituting a core pangenetic attribute combination can be identified. The identified core attributes can be stored as candidate attributes, or as a combination of candidate attributes (i.e., a candidate pangenetic attribute combination). Various combinations of the core attributes can be independently evaluated for frequencies of occurrence and strength of association with the specified item preference to determine a set containing even smaller pangenetic attribute combinations comprised of subsets of core attributes, each of these even smaller core pangenetic attribute combinations potentially having very different strengths of association with the specified item preference. When compiled into pangenetic attribute combination databases, these numerous small core pangenetic attribute combinations can enable methods of predisposition prediction and predisposition modification to provide considerably more accurate, comprehensive, flexible and insightful results.

In another embodiment of a computationally efficient method for compiling co-associating attributes, a bottom-up approach is used for determining pangenetic attribute combinations that are associated with an item preference. This bottom-up approach generates sets of attributes in stages, starting with small pangenetic attribute combinations and progressively building on those to generate larger and larger pangenetic attribute combinations. At each stage, only the pangenetic attribute combinations that are determined to be statistically associated with the specified item preference are used as building blocks for the next stage of generating larger pangenetic attribute combinations. The attributes used for generating these pangenetic attribute combinations can be selected from an pangenetic profile, from an pangenetic attribute combination, from a set of candidate attributes, or from a candidate pangenetic attribute combination, for example. At each stage, all of the pangenetic attribute combinations that are generated contain the same number of attributes, and can therefore be referred to as a set of n-tuple combinations of attributes, where n is a specified positive integer value designating the number of attributes in each n-tuple combination of attributes. This method can be used for de novo identification of pangenetic attribute combinations that are statistically associated with an item preference, as well as for identifying one or more core pangenetic attribute combinations from a previously identified candidate pangenetic attribute combination. The method can begin by generating n-tuples of any chosen size, size being limited only by the number of attributes present in the pangenetic profile, pangenetic attribute combination, or set of attributes from which attributes are selected for generating the n-tuple combinations. However, it is preferable to begin with small size n-tuple combinations if using this bottom-up approach for the de novo identification of pangenetic attribute combinations because this method typically requires generating all possible n-tuple combinations for the chosen starting value of n in the first step. If the n-tuple size chosen is too large, an unmanageable computational problem can be created. For example, if n=50 is chosen as the starting n-tuple size with a set of 100 attributes, all possible 50-tuple combinations from the 100 attributes would be $1 \times 10^{29}$ combinations, which is a currently unmanageable even with current supercomputing power. Therefore, it is more reasonable to choose 2-tuple, 3-tuple, 4-tuple, or 5-tuple sized combinations to start with, depending on the size of the set of attributes from which the n-tuple combinations will be generated and the amount of computing time and computer processor speed available. Once a first set of n-tuple combinations of attributes is generated, frequencies of occurrence are determined for each n-tuple combination in a set of pangenetic profiles associated with the specified item preference and in a set of pangenetic profiles that is not associated with the specified item preference. Each n-tuple combination that is statistically associated with the specified item preference is identified based on the frequencies of occurrence and stored in a compilation containing pangenetic attribute combinations that are associated with that item preference. If no n-tuple combinations are determined to be statistically associated with the item preference specified, the value of n can be incremented by one and the method can be reiterated, beginning at the first step, for the larger n-tuple size. If, on the other hand, at least one n-tuple was determined to be statistically associated with the specified item preference and stored in the compilation, a set of (n+1)-tuple combinations are generated by combining each stored n-tuple combination with each attribute in the set of attributes that does not already occur in that n-tuple (combining an n-tuple with an attribute from the set that already occurs in that n-tuple would create an (n+1)-tuple containing an attribute redundancy, which is undesirable). Next, frequencies of occurrence of the (n+1)-tuple combinations are determined and those (n+1)-tuple combinations which have a higher strength of association with the specified item preference than the n-tuple combinations from which they were generated are stored in the compilation containing pangenetic attribute combinations that are associated with the specified item preference. Storing an (n+1)-tuple combination that does not have a higher strength of association with the specified item preference than the n-tuple combination from which it is generated effectively adds an pangenetic attribute combination to the compilation which contains an additional attribute that is not positively associated with the specified item preference, something that is undesirable. Provided at least one (n+1)-tuple combination has a stronger statistical association with the specified item preference and was stored, the value of n is incremented by one and a next iteration of the method is performed, so that the (n+1)-tuple combinations generated during the current iteration become the n-tuple combinations of the next iteration. By generating progressively larger n-tuple combinations at each iteration and storing those that have increasingly stronger statistical association with the specified item preference than the ones before, a compilation of pangenetic combinations that are associated with the specified item preference is generated which can be used effectively for methods of web search, web item recommendation, and user satisfaction and behavior prediction.

Confidentiality with respect to personal pangenetic data can be a major concern to individuals that submit their data for use in the disclosed inventions. Embodiments exist in which the identity of an individual can be linked directly or indirectly to their data, masked, anonymized, or provided only by privileged access or through authorization procedures, including but not limited to the embodiments which follow.

In one embodiment the identity of individuals are linked to their pangenetic profiles. In one embodiment the identity of individuals are linked directly to their pangenetic profiles. In one embodiment the identity of individuals are linked indirectly to their pangenetic profiles. In one embodiment the identity of individuals are anonymously linked to their pangenetic profiles. In one embodiment the identity of individuals are linked to their pangenetic profiles using a nondescriptive alphanumeric identifier. In one embodiment the identity of individuals are linked to their pangenetic profiles using a nondescriptive non-alphanumeric identifier. In one embodiment the identity of individuals are linked to the pangenetic attributes they possess as stored in one or more datasets of the methods. In one embodiment the linkage of identity is direct. In one embodiment the linkage of identity is indirect. In one embodiment the linkage of identity requires anonymizing or masking the identity of the individual. In one embodiment the linkage of identity requires use of a nondescriptive alphanumeric or non-alphanumeric identifier.

In one embodiment, an authorization granting access to the pangenetic data can be generated, transmitted and/authenticated if user input is supplied in the form of at least one combination of characters that matches at least one combination of characters (e.g., a user_ID, password, passphrase, passcode, or PIN) previously stored in association with the user, each of the characters being selected from the group consisting of alphanumeric characters and non-alphanumeric characters. For additional security, the combination of characters stored in association with the user can be stored as a cryptographic hash. In another embodiment, the authorization granting access to the pangenetic data can be generated if user input is supplied in the form of at least one combination of characters that matches at least one combination of randomly selected characters (e.g., automatically generated single-use passwords, and CAPTCHA and reCAPTCHA passwords) by software that interacts with the authorization interface, each of the characters being selected from the group consisting of alphanumeric characters and non-alphanumeric characters. In another embodiment, the authorization granting access to the pangenetic data can be generated if user input is supplied in the form of biometric data that matches biometric data previously stored in association with the user.

In one or more embodiments, data masks can be used in the present inventions to block access, reading and/or transmission of at least a portion of the data (i.e., data profile) associated with one or more users. Any type of pangenetic and non-pangenetic data can potentially be masked using data masks. Pangenetic data that can be masked includes, but is not limited to, individual attributes such as nucleotide identities within full or partial genomic sequence, SNP identities contained in genome scans, individual epigenetic modifications, epigenetic patterns (i.e., motifs), genetic or epigenetic regulated gene expression patterns (which can be tissue specific), individual genetic mutations, genetic mutation rates, telomere length (a marker of age and the rate of senescence), and occurrences of genome integrated viruses and virus sequences (such as occurrences of integration of HIV virus into the human genome). A user may want portions of their pangenetic data to be masked to ensure that certain confidential regions cannot be accessed or read by the other users and entities, including the pangenetic web search, recommendation, and prediction system. Confidential regions may include, for example, particular genetic sequences or epigenetic patterns that can reveal the individual's present health conditions, their susceptibilities toward acquiring particular diseases in the future (i.e., disease predispositions), or their predicted lifespan (i.e., longevity predisposition). Also, in instances where a consumer appoints someone else as a user to employ applications of the disclosed invention which use the consumer's pangenetic data, the consumer may want to keep the majority of their pangenetic information inaccessible and only permit access to the minimum amount of pangenetic data necessary for the particular application (e.g., an insurer or administrator looking up information on behalf of the consumer or requesting recommendations for the consumer). However, it should be noted that increased masking of pangenetic attributes may result in decreased certainty and accuracy of search results, recommendations and predictions by the pangenetic based web system.

To enable both individualized and application dependent control of pangenetic data access, one or more data masks (i.e., pangenetic data masks, non-pangenetic data masks) can be used to control access, reading and/or transmission of certain data attributes as specified by an authorized user. In one embodiment, one or more data masks can be associated with (i.e., linked to) one or more sets of data or a data profile (i.e., a pangenetic profile or a non-pangenetic profile) associated with a user. The data masks can be further linked to identifiers of other particular users, such as individuals (e.g., friends, acquaintances, business contacts, secondary users) and organizations (e.g., product and service providers) interacting with or acting on behalf the primary user, and/or they can be associated with particular queries or particular applications (certain web search engine sites or online shopping websites, for example). The data mask can be pre-approved by the consumer associated with the pangenetic data being masked, or the data mask can be pre-approved by a pangenetic based system that had previously identified a minimum set of pangenetic attributes required for accurate and reliable pangenetic based search, recommendation or prediction. When a user, application, website or system attempt to access the user's data, the appropriate mask will be applied to ensure access or transmission of only those portions of the consumer's data for which permission is granted. In another embodiment, data masks can be applied selectively in association with particular queries or applications, without regard to the particular entity (e.g., user, organization, computer system) that is accessing the consumers' data to implement those queries or applications. Generally, pangenetic data masks that are associated with particular users or applications can provide the added benefit of increasing processing efficiency of the disclosed methods by streamlining access and/or reading of consumer data attributes to only the designated portions of their data considered relevant to the particular user, query or application. In one embodiment, a data mask associated with a particular user and a data mask associated with a particular query or application can be applied simultaneously when accessing a consumer's data profile (and can span one or more data records of a data profile). In one or more embodiments, the user approves the data masks that are applied to their pangenetic and/or non-pangenetic data.

In one or more embodiments, a consensus mask (consensus data mask) can be generated from two or more data masks and used to limit access to a portion of the data represented by the intersection between those two or more data masks. In one embodiment, the consensus mask can be a data mask representing a consensus between a plurality of data masks with respect to which data should be unmasked. In another embodiment, a consensus mask can be a data mask that represents a set of attributes (i.e., attribute positions or identifiers, data record positions or identifiers) that a plurality of data masks all agree are permissible for access, reading and/or transmission. In the embodiment disclosed above which describes the simultaneous application of two or more data masks—at least one data mask associated with a consumer or user, and at least one data mask associated with a query or application—a consensus mask can be generated from the intersection of those two or more data masks and applied when accessing and/or transmitting the individual's data, effectively achieving the same result as the simultaneous application of the two or more separate data masks. In one embodiment, the simultaneous application of two of more data masks comprises the generation and application of a consensus mask. Consensus data masks can be applied to the pangenetic and non-pangenetic profiles of an individual.

A consensus mask can also be generated and used in circumstances of pangenetic profiling where, for example, two or more individuals have chosen to make at least a portion of their pangenetic data inaccessible using pangenetic data masks, but those pangenetic masks differ from each other. A consensus mask can be generated from the intersection of the differing data masks and then applied to the data profiles of all of the individuals being considered in that particular instance. With respect to pangenetic data for example, this ensures that the same set of pangenetic attributes, a minimal shared set of attributes, will be accessed for all of the pangenetic profiles associated with a group of individuals. So, by generating and using a consensus mask with respect to a group, inadvertent access to confidential pangenetic data can be prevented for the entire group while at the same time ensuring uniform access to exactly the same pangenetic attributes within each individual's pangenetic profile, thereby providing consistent and valid results when determining statistical association values, as may be required when determining correlations between pangenetic attributes and web items and or item ratings.

FIG. 7 illustrates abstract representations of data masks, more specifically three data masks labeled as data masks #1, #2 and #3 and one consensus mask that was generated from those three data masks. Within each of the masks, the 'M' character represents a mask attribute indicator which indicates that the corresponding attribute is masked and therefore inaccessible for reading or transmission. Within each of the masks, each 'U' character represents an unmask attribute indicator which indicates that the corresponding attribute is unmasked and therefore accessible for reading or transmission. With respect to masking of pangenetic data, each 'M' and 'U' character that is illustrated can correspond to a pangenetic attribute constituting an individual nucleotide, a SNP, a string of nucleotides (i.e., a nucleotide sequence), one or more partial or complete genes, an epigenetic nucleotide modification, or one or more partial or complete epigenetic patterns, for example. With respect to masking of non-pangenetic data, each 'M' and 'U' character that is illustrated can correspond to a variety of non-pangenetic attributes or combinations of non-pangenetic attributes.

Referring again to FIG. 7, the consensus data mask can be generated by at least two approaches. In an embodiment of a first approach, which is based on determining the intersection of unmasked attributes of a set of data masks, every unmasked attribute position that is common to all the data masks is compiled into a singular collective mask in which the remaining positions are designated as masked attribute positions by default, thereby creating the consensus mask. In an embodiment of a second approach, which is based on determining the union of masked attributes of a set of data masks, masked attribute positions that are present in at least one of the data masks are consolidated into a singular collective mask in which the remaining positions are designated as unmasked attributes by default, thereby creating the consensus mask.

Both data masks and consensus data masks should align appropriately to the respective data profiles of the individuals, to ensure that each attribute associated with each of the individuals is handled as masked or unmasked in accordance with the corresponding data mask. In one embodiment, this can be achieved by generating and using data masks (and consensus data masks) that cover the entire data profile of an individual, from beginning to end, such that every attribute or attribute group (an associated set of attributes treated as a single unit) present within the data profile of the individual has a corresponding indicator in the mask (e.g., either a 'M' and 'U' character) which indicates whether that attribute is to be treated as a masked attribute or an unmasked attribute with respect to access and/or transmission. In an alternative embodiment, a data mask does not cover the entire pangenetic or non-pangenetic profile of a individual, but rather, is mapped to corresponding attributes in the profile of the individual using attribute identifiers, indices, addresses, pointers or keys which ensure that the masked and unmasked attribute indicators point to (i.e., map to) the appropriate attributes (i.e., corresponding attribute values) contained in the individual's data profile. In one embodiment, only masked attribute positions are represented in the data mask using attribute identifiers, indices, addresses, pointers or keys which point to the corresponding attributes of the individual's data profile, the unmasked attributes being absent from the data mask. In another embodiment, only the unmasked attribute positions are represented in the data mask using attribute identifiers, indices, pointers or keys which point to the corresponding attributes of the individual's data profile, the masked attributes being absent from the data mask.

There are several different methods by which to apply a data mask to a data profile. In one embodiment, a data mask is merged with a data profile of an individual to generate a temporary data profile (a masked hybrid data profile) of the individual. This can be accomplished by generating a copy of a data profile of the individual and replacing those attribute values which the data mask indicates need to be masked with, for example, nondescriptive placeholders such as an alphanumeric character or a symbol (e.g., 'X', '#', '*', or '$'), or alternatively, deleting the masked attribute values from the temporary data profile. The temporary data profile can then be made available in its entirety for reading or transmission without having to block access or transmission of any of the attributes it contains.

In a different embodiment, a data mask can be applied to a data profile by accessing, reading or transmitting data from the data profile in accordance with the pattern of mask and unmask indicators contained in the data mask. As such, the data mask is executed as a set of instructions, wherein each unmask attribute indicator is interpreted as a read/transmit (i.e., process attribute) instruction with respect to the corresponding attribute value in the individual's data profile, and wherein each mask attribute indicator is interpreted as a non-read/non-transmit (i.e., skip attribute) instruction with respect to the corresponding attribute value in the individual's data profile. In one embodiment, the data mask contains only unmask attribute indicators that provide read/transmit instructions with respect to the corresponding attribute values in the individual's data profile, wherein the unmask attribute indicators are mapped to the corresponding attributes of the individual's data profile using attribute identifiers, indices, addresses, pointers or keys. In another embodiment, the data mask contains only mask attribute indicators that provide non-read/non-transmit instructions with respect to the corresponding attribute values in the individual's data profile, wherein the mask attribute indicators are mapped to the corresponding attributes of the individual's data profile using attribute identifiers, indices, addresses, pointers or keys.

Figure 8:
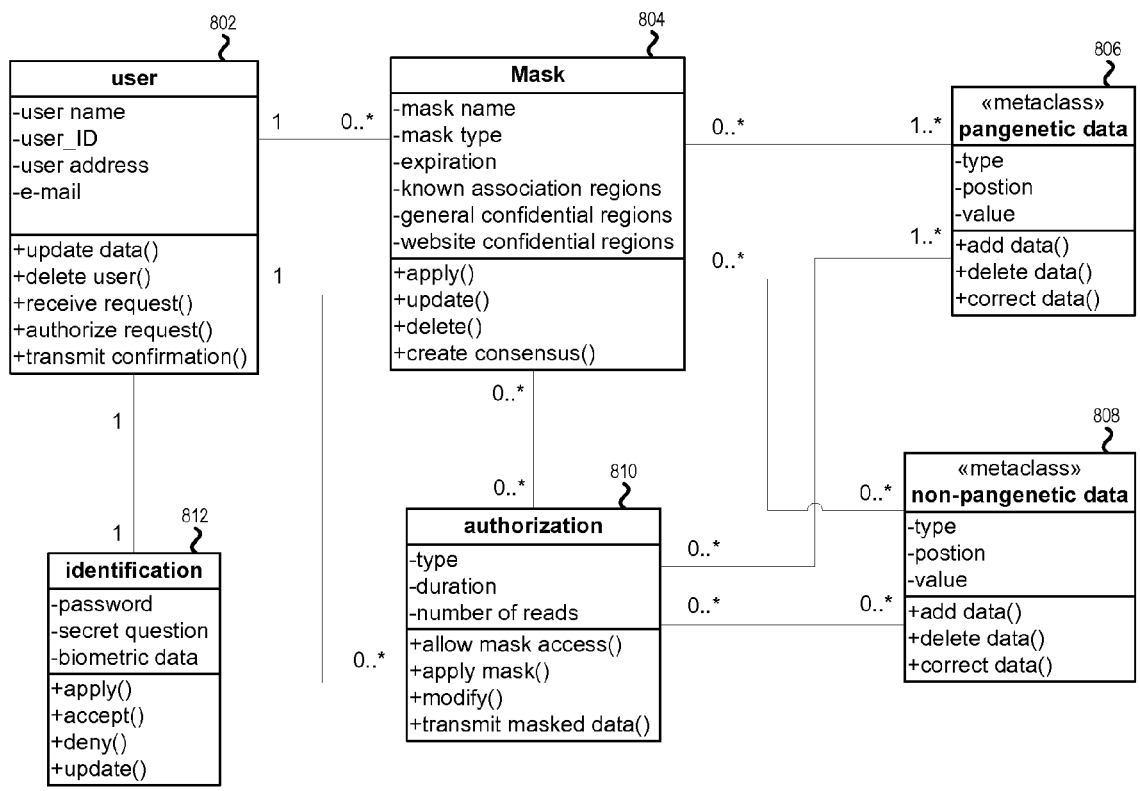
FIG. 8 illustrates a class diagram depicting a pangenetic web database which incorporates masking of pangenetic and non-pangenetic data.

FIG. 8 illustrates a Unified Modeling Language (UML) class diagram depicting one embodiment of a pangenetic web search, recommendation and prediction database system which incorporates masking of pangenetic and non-pangenetic data. The user class 802 can interact indirectly with a pangenetic data metaclass 806 and a non-pangenetic data metaclass 808 (each of which can contain many types of pangenetic data and non-pangenetic data respectively), through an authorization association which can apply masks to the pangenetic data and the non-pangenetic data to obtain appropriately masked data.

As can be seen from FIG. 8, a user that attempts to access the database system can be identified by the system to ensure that they receive the appropriate degree of access, and the ability to add and modify data as appropriate. As illustrated, an identification class 812 which includes security related attributes such as a password, secret question, and biometric data (e.g., fingerprint scan, retinal scan, or facial recognition data) can be used by the system to identify the user provides when the user logs in to gain access to the system, for example. The various operations associated with identification class 812 can include an apply operation in which security related attributes are requested of and received from the user; an accept operation in which the identifying information provided by the user at the time of requested access are determined to match stored identification attributes of the user, resulting in granting of access; a deny operation in which identifying information provided by the user at the time of requested access are determined to differ from stored identification attributes of the user, resulting in denial of access; an update operation in which identifying information stored in association with the user (e.g., an identification profile of the user) can be updated to reflect changes in that information, for example user or system initiated password changes.

As further illustrated in FIG. 8, user class attributes which characterize the user can include a user name, a user_ID, a user address (i.e., mailing, billing, business and/or residential address), and an email address. The user class attributes can be recorded in a user profile contained in a database of the system. Various operations can be associated with user class 802 and, as illustrated, can include an update data operation that enables the system to update user attributes associated with the user; a delete user operation that enables the system to delete a user record from the system database; a receive request operation that enables the user to input a request for implementation of a specific operation (i.e., functionality) of the system, such as a request to create a mask or a request to perform a web search query; an authorize request operation that enables the system to authorize the user's request based on the identifying information associated with the user and any permission profiles and/or masks associated with the user, other users, web items, websites, and particular implementation (i.e., application) or system involved, all of which can be used to determine the level and pattern of data access that is permissible in that instance; and a transmit confirmation operation that enables the system to transmit an indication to the user and other components of the system that access is permitted in accordance with the permission profiles, masks, and the access determination generated for that user for the purpose requested.

As further illustrated in FIG. 8, user class 802 can interact with mask class 804 to create and modify various types of data masks. The user can, for example, initiate the creation of masks having attributes which, as illustrated, can include the mask name; the mask type (e.g., general mask types such as genetic, genetic coding, genetic regulatory, epigenetic, non-pangenetic, demographic, or more specific mask types such as those corresponding to and identified by gene name or corresponding trait/condition, for example); the expiration time/date of the mask; the known association regions (i.e., those portions/regions of the masked data that are known to associate with particular web items, item satisfaction levels or online behaviors); general confidential regions which indicate data that are to be kept private (masked) from others; and website confidential regions which indicate data that are to be masked specifically with respect to access and reading of the data by specific websites or web based applications. Various operations can be associated with mask class 804 and, as illustrated, can include an apply operation in which a mask is applied to a set of data; an update operation in which a mask is updated based on user or system supplied information; a delete operation in which a user can implement deletion of a mask or the system can perform automated deletion of a mask that has reached its expiration date; and a create consensus operation in which a consensus data mask can be generated from two or more masks as disclosed previously and then applied to targeted data in accordance with the apply operation.

As further illustrated in FIG. 8, the user class 802 interacts with authorization class 810 to control access, reading and transmission of consumer associated data (i.e., pangenetic and non-pangenetic data) through application of data masks to the data. Authorization class 810 includes a type attribute which can indicate whether a particular authorization relates to access of pangenetic or non-pangenetic data types, and/or which user, website or application is attempting to receive access to the data; a duration attribute which can specify the amount of time granted for accessing the data and/or can specify the length of time permissible for a user time-out, after which the system can execute an automated logout of the user from the system; and a number of reads attribute which indicates the number of times the data can be accessed during a each user session, or the number of times a particular portion of the data can be transmitted to a particular destination during each user session. Various operations can be associated with authorization class 810 and, as illustrated, an allow mask access operation can enable the user to access a mask for analysis, modification or deletion; an apply mask operation which enables a user to modify an existing mask; and a transmit masked data operation which enables the transmission of masked data to a destination such as a web server.

FIG. 8 further illustrates a pangenetic data metaclass 806 representing various pangenetic data classes, each of which can be characterized by attributes including a type attribute which indicates the type of pangenetic data; a position attribute which indicates the position of the corresponding genetic or epigenetic attribute within the genome and/or within a mask; and a value attribute which indicates the value of the genetic or epigenetic attribute, for example the value of a nucleotide attribute (e.g., C, A, T or G). The pangenetic data metaclass 806 can have various operations including an add data operation which enables the addition of new pangenetic data to a pangenetic profile of the user; a delete data operation which enables the deletion of pangenetic data from the pangenetic profile of a user; and a correct data operation which enables the modification of pangenetic data contained in the pangenetic profile of a user.

FIG. 8 further illustrates a non-pangenetic data metaclass 808 representing various non-pangenetic data classes, each of which can be characterized by attributes including a type attribute which indicates the type of non-pangenetic data; a position attribute which indicates the position of the corresponding non-pangenetic attribute within a dataset and/or a mask, and a value attribute which indicates the value of the non-pangenetic attribute, for example a zip code value which indicates a user location. The non-pangenetic data metaclass 808 can have various operations including an add data operation which enables the addition of new non-pangenetic data to a pangenetic profile of the user; a delete data operation which enables the deletion of non-pangenetic data from the pangenetic profile of a user; and a correct data operation which enables the modification of non-pangenetic data contained in the non-pangenetic profile of a user.

Figure 9:
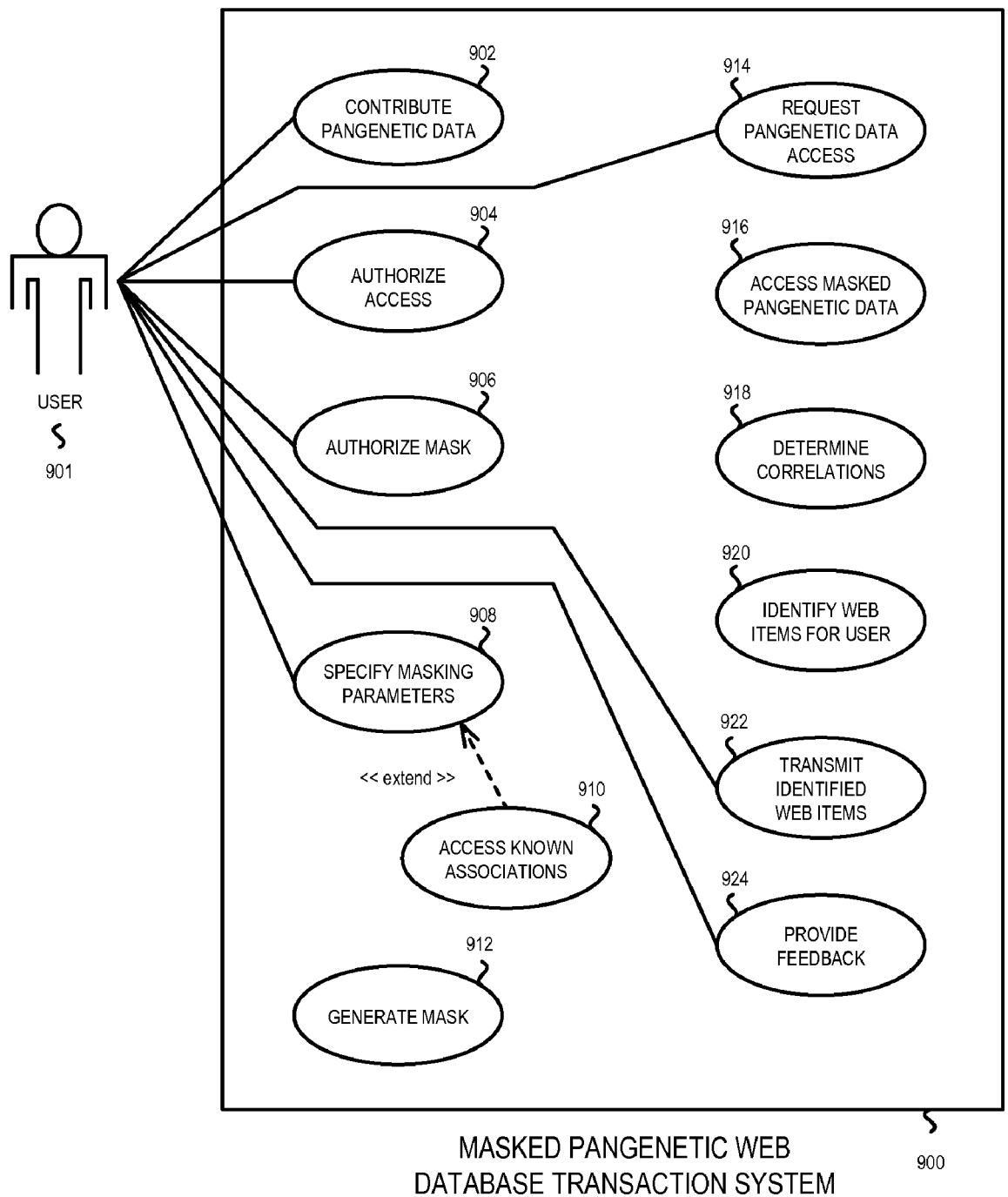
FIG. 9 illustrates a use-case diagram depicting a masked pangenetic web database system.

FIG. 9 illustrates a UML use case diagram depicting one embodiment of a masked pangenetic web database transaction system 900 in which a user can control the masking of their pangenetic data for web based applications. The user 901 (e.g., a consumer) can add pangenetic data to the masked pangenetic web database transaction system 900 through contribute pangenetic data use case 902 in which the user can request import of their pangenetic data from an interface such as their desktop computer, mobile computing device, a remote pangenetic database server or another source; the authenticity of the pangenetic data can be verified; and the data can be reformatted, if necessary, to match a standardized format consistent with requirements for pangenetic masking, and pangenetic based web search and recommendation and user satisfaction and behavior prediction. Through authorize access use case 904, the user 901 can indicate websites, web based applications and other users that are permitted at least some degree of access to the user's pangenetic and non-pangenetic data contained in the database of the system. In authorize mask use case 904, the user 901 can authorize which masks the system should apply when particular websites, web based applications and users attempt to access or receive the user's confidential (i.e., sensitive, private) pangenetic and non-pangenetic data. The user 901 can generate and/or modify masks for application to their pangenetic and non-pangenetic data by indicating which specific attributes they want concealed in each mask through specify masking parameters use case 908. With respect to pangenetic attributes, specify masking parameters use case 908 can further allow user 901 to specify particular pangenetic based diseases and traits for which they wish to keep the corresponding pangenetic attributes concealed. The system can identify the pangenetic attributes associated with those specified disease and traits through access known associations use case 910 and then designate and/or recommend those attributes as parameters to be masked through specify masking parameters use case 908. In generate mask use case 912, the system uses the specified masking parameters and mask authorizations to generate one or more masks that can be linked not only to the user, but to particular websites, web based applications and other users as authorized by the user or as determined by the system.

Further with respect to FIG. 9, user 901 can submit their identifying information (e.g., user_ID and password), requests or authorization for access to their pangenetic data, and queries for web search and recommendation through request pangenetic data access use case 914. Based on the particular query type, website, or application, the system can select and apply the appropriate mask to the pangenetic data if appropriate. Masked pangenetic web database transaction system 900 can access the masked pangenetic data through access masked pangenetic data use case 916. If a query happens to encompass web items for which pangenetic based correlations have not been previously determined, the system 900 can determine correlations between the pangenetic data and feedback of other users with respect to the item through determine correlations use case 918, and store the correlations in an item feedback matrix. The system can then identify the best web items for the user based on the stored correlations and a comparison of the masked pangenetic data of the user with pangenetic data combinations contained an item feedback matrix stored in the system through identify web items for user use case 920. The identified web items can be presented as recommendations to the user in the form of various annotations (e.g., text, tabulations, bars, buttons, icons, hypertext, hyperlinks) through the user's interface in transmit identified web items use case 922. In provide feedback use case 924, the user 901 can provide explicit or implicit feedback to the system (e.g., satisfaction, dissatisfaction) with respect to the recommended web items. For example, if a rank listing of web items was provided by the system, user 901 can select (e.g., click on) one or more web items from the rank listing that they prefer over the others thereby indicating their preferences and providing feedback.

Figure 10:
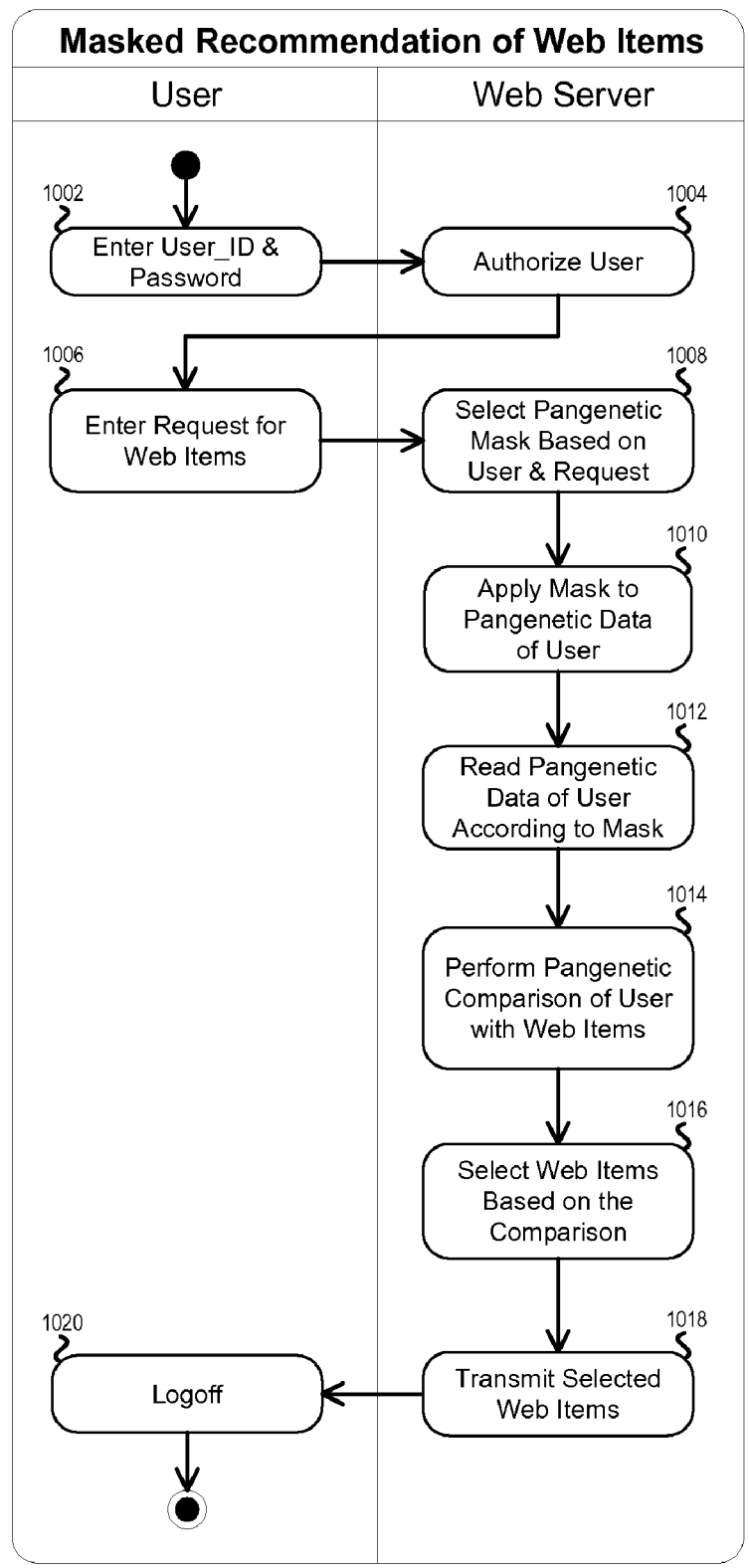
FIG. 10 illustrates an activity diagram depicting masked pangenetic based recommendation of web items.

FIG. 10 illustrates a UML activity diagram depicting one embodiment of a method for masked recommendation of web items for a user in which a mask is applied to pangenetic data of the user prior to using the pangenetic data for determining a recommendation. In enter user_ID & password step 1002, a user gains secure access to a pangenetic based web server (i.e., pangenetic based computer database system) by logging on to the system with their secure personal login identifiers. This login information can alternatively be in the form of other secure login procedures such as retinal or fingerprint scan (i.e., biometric data), or a personal identification card that is based on magnetic or RFID technology. In authorize user step 1004, the user logon information is verified and access is granted if the security information passes verification. In one embodiment, the pangenetic server is under the control of an administrator. In enter request for web items step 1006, the user requests, either explicitly or implicitly, recommendation of one or more web items. In select pangenetic mask based on user & request step 1008, the system selects a pangenetic mask based on the identity of the user and the type request entered by the user.

As previously disclosed, a completely different mask may be applied to the user's pangenetic data depending on who the user is, and whether the request results are to be transmitted as output to the user or a different user or entity such as a website. The nature of the request can also determine the application of additional masks, for example, a mask associated with item type, item provider type or request type which reduce the number pangenetic attributes of the user that need to be read, so that those which are considered by the system to be irrelevant are masked. With respect to FIG. 10, in apply mask to pangenetic data of user step 1010, one or more masks can be applied to the pangenetic data of the user for the purpose of concealing pangenetic attributes that are considered by the user and/or the system to be confidential with respect to the user and the request. In one embodiment this can involve the generation and application of a consensus mask created from two or more masks. In read pangenetic data of user according to mask step 1012, the pangenetic attributes associated with the user are read in accordance with the applied mask (i.e., only the unmasked pangenetic attributes are read). In perform pangenetic based comparison of user with web items step 1014, the system compares the unmasked pangenetic attributes of the user with pangenetic data combinations correlated with web items in an item feedback matrix, for example.

In one embodiment, the unmasked pangenetic attributes associated with the user are compared with the pangenetic data combinations by determining the percent match (one type of pangenetic similarity measure) between each pangenetic data combination and the pangenetic data of the user, and then ranking the pangenetic data combinations based on the percent matching achieved relative to one another. In one embodiment, the rank is also based on satisfaction levels, so that both satisfaction level and percent match are used to determine rank in a concurrent evaluation in which a pangenetic combination associated with a higher satisfaction level than another pangenetic combination will receive the higher rank when both have the same degree of pangenetic similarity to the user. In another embodiment, the percent match and the satisfaction level associated with a correlation are both used to determine rank of the correlation, but are differentially weighted for the purpose of making the determination. With respect to FIG. 10, in select web items based on the comparison step 1016, the most highly ranked (i.e., the best matching) web item for the user can be selected by the system, or alternatively, several of the most highly ranking web items can be selected by the system and presented as a listing to the user, for example. In one embodiment, the number of web items to be selected can be a predetermined parameter set by the user or system, or can be based on a predetermined threshold which specifies a minimum value for the quality or percentage of matching between the pangenetic data associated with the user and a pangenetic data combination associated with a web item. In transmit selected web items step 1018, the one or more web items are transmitted by the system to the user. The destination of the transmission can also be to a database, a dataset, a computer readable memory, a computer readable medium, a computer processor, a computer network, a printout device, a visual display, and a wireless receiver. In one embodiment, the transmission can include ranks of the services or providers and/or the associated satisfaction levels (this is applicable to several embodiments disclosed herein). While not shown in the diagram, optional steps in which the user provides explicit feedback (i.e., active feedback) or implicit feedback (i.e., passive feedback) regarding their satisfaction or perceived relevance of the transmitted web items, and the system receives and stores the feedback, can be included. In logoff step 1020, the user logs out to end the session and terminates secure access to the system. This logoff step can be automated based on closing the application or moving out of range of an optical sensor or RFID sensor which detects the presence of the authorized user to ensure that an unauthorized user does not inadvertently gain access the user's pangenetic data or pangenetic based results, thereby ensuring that privacy can be maintained in a public setting to ensure that others do not gain access to an individual's pangenetic data through an easily captured mobile device, for example.

Figure 11:
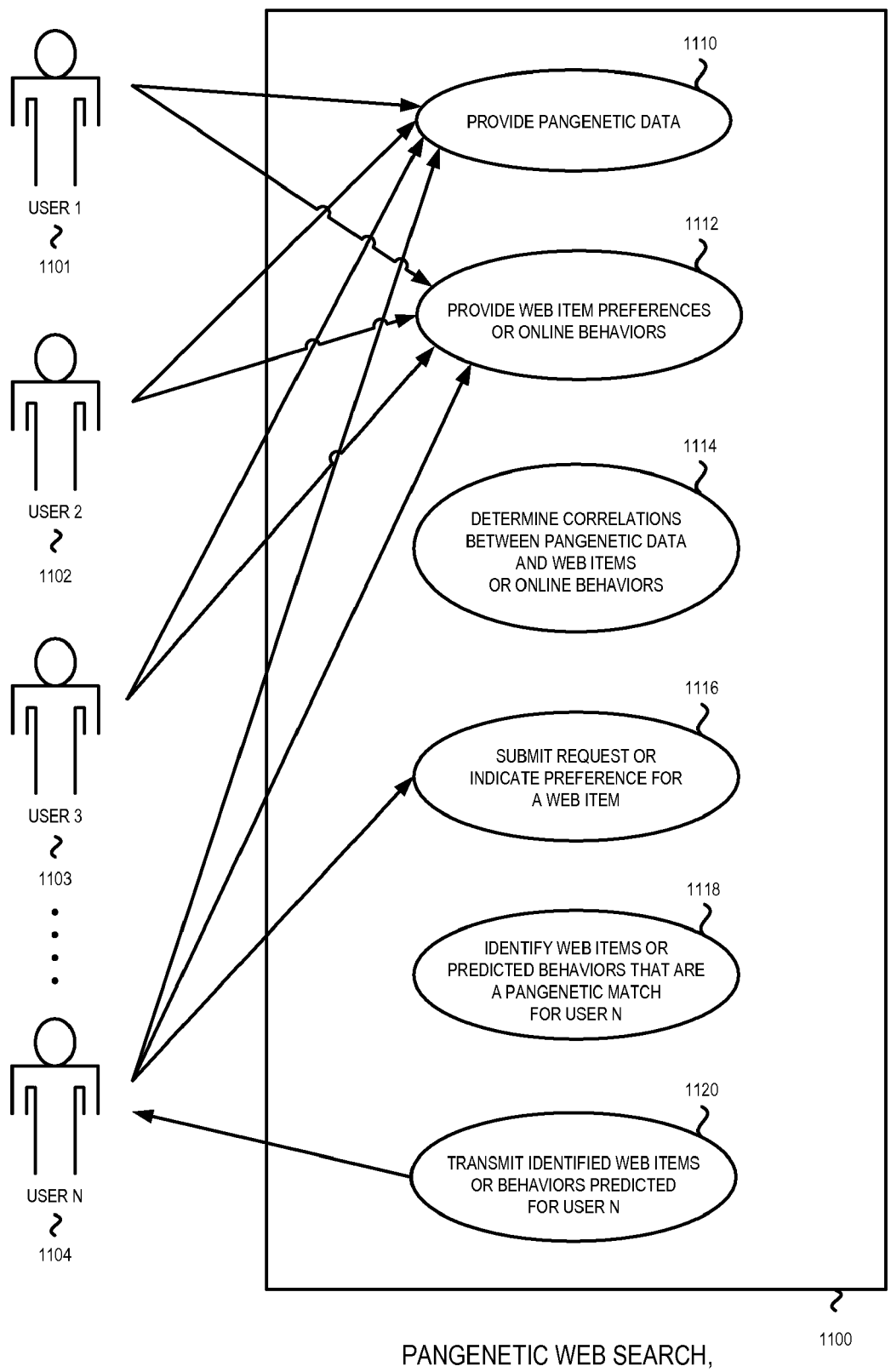
FIG. 11 illustrates a use-case diagram depicting a pangenetic web search, recommendation and prediction database system.

FIG. 11 illustrates a UML use case diagram depicting one embodiment of a pangenetic web search, recommendation and prediction system 1100 which allows a plurality of users—user 1 (1101), user 2 (1102), user 3 (1103) through user N (1104)—to contribute pangenetic data to the system through provide pangenetic data use case 1110 which, in one embodiment, can be accomplished through transfer of pangenetic data associated with the users from electronic files stored in the database of a pangenetic database server, such as that maintained by a web search engine server or a Personal Health Record (PHR) server. In an alternative embodiment, the pangenetic data may be stored as a file (e.g., a portable pangenetic profile stored in computer readable form) in the memory of the users' personal computers or mobile devices which are being used to interface with the system, and the system can access, read, and/or upload all or portions of the file as authorized. Data indicating item preferences (e.g., satisfaction levels) or online behaviors with respect to various web items can be provided to the system through provide web item preferences or online behaviors use case 1112. This data can be provided directly by those individuals through active or passive feedback, or derived indirectly through historical records or profiles associated with those users. In determine correlations between pangenetic data and web items or online behaviors use case 1114, correlations between combinations of the users' pangenetic data and either web based items or user online behaviors are computed by the system using the pangenetic data and user feedback and behavior data. As explained previously, the correlations can be determined using a variety of pattern finding algorithms and statistical association measures. The determined correlations can be stored in an item feedback matrix as previously described. In submit request or indicate preference for a web item use case 1116, the user N 1104 can submit a query for one or more web items or can indicate a potential interest in an item, by explicitly or implicitly expressing a characteristic or preference which can be further interpreted or predicted to be potential interest in a web item or type of web based item. An implicit expression of potential interest could, for example, be used to aid in selecting items for advertisement to the user on a visual display. In identify web items that are a pangenetic match to user N use case 1118, the system uses both the pangenetic data and the submitted request or indicated item preference data of user N 1104 for comparison with the item feedback matrix containing the determined correlations. In one embodiment, the request or item preference data is used to select a subset of items in the item feedback matrix, which are then subjected to a pangenetic similarity comparison between the pangenetic data associated with user N 1104 and the combinations of pangenetic data correlated with web items or user behaviors. In identify web items or predicted behaviors that are a pangenetic match for user N use case 1118, web items or user behaviors that are a pangenetic match for user N 1104, for example those that are an exact match or have a high enough degree of pangenetic similarity as indicated by a predetermined threshold value, can be identified as selections or recommendations for user N 1104. In transmit identified web items or behaviors predicted for user N use case 1120, the web items or behaviors identified by the system as being relevant or appropriate for the user are transmitted to user N 1104 to fulfill their request or implied interest.

In one embodiment, a computer based method for generating a pangenetic based item feedback matrix is provided comprising i) accessing item feedback data from a plurality of individuals with respect to one or more web items; ii) accessing pangenetic data associated with the plurality of individuals; iii) determining, by statistical association based on the item feedback data, correlations between the web items and combinations of the pangenetic data; and iv) storing the correlations between the web items and the combinations of pangenetic data to generate a pangenetic based item feedback matrix. The method can further comprise a step of transmitting one or more of the correlations from the pangenetic based item feedback matrix to at least one destination selected from the group consisting of the user, a database, a dataset, a computer readable memory, a computer readable medium, a computer processor, a computer network, a printout device, a visual display, and a wireless receiver. The method can also further comprise acts of i) transmitting at least one authorization request for access to the pangenetic data associated with the plurality of individuals, and ii) receiving an authorization granting access to the pangenetic data associated with the plurality of individuals.

In one embodiment of a computer based method for generating a pangenetic based item feedback matrix, the pangenetic data is pangenetic metadata. In one embodiment, the content of the item feedback matrix is stored within a dataset selected from the group consisting of an internet search engine document index, an internet search engine hitlist, and an internet search engine lexicon. In one embodiment, the determined correlations are used to generate a dataset selected from the group consisting of an internet search engine document index, an internet search engine hitlist, and an internet search engine lexicon. In one embodiment, the pangenetic data associated with the plurality of individuals constitute a plurality of pangenetic profiles of the individuals.

In one embodiment of a computer based method for generating a pangenetic based item feedback matrix, at least a portion of the correlations stored in the pangenetic based item feedback matrix are used for a method of providing internet search results for a user. In one embodiment, at least a portion of the correlations stored in the pangenetic based item feedback matrix are used for a method of online recommendation of items for a user. In one embodiment at least a portion of the correlations stored in the pangenetic based item feedback matrix are used for a method of online prediction of user satisfaction with an item. In one embodiment at least a portion of the correlations stored in the pangenetic based item feedback matrix are used for a method of predicting user behavior.

In one embodiment of a computer based method for generating a pangenetic based item feedback matrix, the plurality of individuals share one or more non-pangenetic attributes in common. In one embodiment, each correlation stored in the item feedback matrix indicates an association between one of the web items and one of the combinations of pangenetic data. In one embodiment, the correlations that are selected for being stored have one or more corresponding statistical association values, as determined by statistical association, that meet one or more predetermined threshold values, where for example, the statistical association values can indicate a minimum level of statistical significance or a minimum level of statistical certainty. In one embodiment, each correlation stored in the item feedback matrix can include at least one statistical association value, as determined by statistical association, which indicates strength of the association between one of the web items and one of the combinations of pangenetic data. In one embodiment, the correlations that are stored have one or more corresponding statistical association values, as determined by statistical association, which are used to rank web items correlating with the same combination of pangenetic data so that the pangenetic combinations having the strongest association with the web items can be readily identified. In one embodiment, the correlations are indicated by scores derived from the feedback data. In one embodiment, the correlations are indicated by ratings derived from the feedback data. In one embodiment, the correlations are indicated using binary indicators such as {like, dislike}.

In one embodiment of a computer based method for generating a pangenetic based item feedback matrix, accessing of the pangenetic data of the individuals is performed in accordance with at least one data mask applied to the pangenetic data. In one embodiment a different data mask that can be specified by each of the plurality of individuals can be applied to their respective pangenetic profiles (i.e., pangenetic data). In an alternative embodiment, the at least one data mask is a consensus data mask derived from a plurality of data masks and then applied uniformly to each of the plurality of pangenetic profiles of the plurality of individuals. In one embodiment, the pangenetic data of the plurality of individuals is performed in accordance with the steps of i) transmitting an authorization request for access to the pangenetic data associated with the plurality of individuals; ii) receiving an authorization which grants access to the pangenetic data; iii) accessing a data mask, wherein the data mask's parameters are associated with the authorization; and iv) applying the data mask to the pangenetic data. In one embodiment the identities of the individuals are masked or anonymized. In one embodiment, non-pangenetic data associated with the individuals is masked.

In one embodiment, a program storage device is provided that is readable by a machine and contains a set of instructions which, when read by the machine, causes execution of a computer based method for generating a pangenetic based item feedback matrix, the method comprising i) receiving item feedback data from a plurality of individuals with respect to one or more web items; ii) accessing pangenetic data associated with the plurality of individuals; iii) determining, by statistical association based on the item feedback data, correlations between the web items and combinations of the pangenetic data; and iv) storing the correlations between the web items and the combinations of pangenetic data to generate a pangenetic based item feedback matrix.

One embodiment of a computer database system for providing internet search results for a user comprises 1) a memory containing a first data structure containing item feedback data from a plurality of individuals with respect to one or more web items, and a second data structure containing pangenetic data associated with the plurality of individuals; and 2) a processor for: i) accessing the first data structure; ii) accessing the second data structure; iii) determining, by statistical association based on the item feedback data, correlations between the web items and combinations of the pangenetic data; and iv) storing the correlations between the web items and the combinations of pangenetic data to generate a pangenetic based item feedback matrix.

Figure 12:
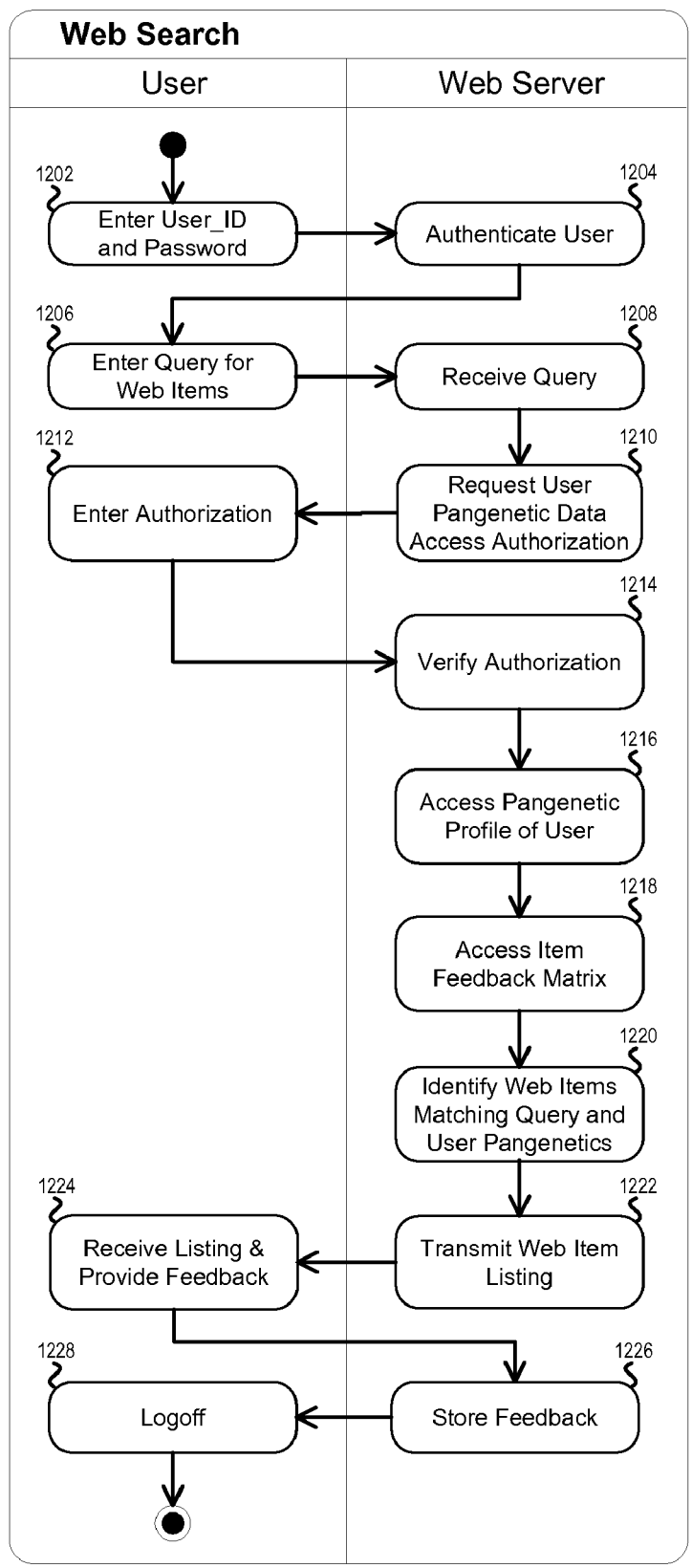
FIG. 12 illustrates an activity diagram depicting pangenetic based web search.

FIG. 12 illustrates a UML activity diagram depicting one embodiment of a method for pangenetic based web search. The method can comprise an enter User_ID and Password step 1202 in which the user can enter information, including biometric information, to logon and authenticate themself to the pangenetic based web server (a pangenetic database system), and an authenticate user step 1204 in which the web server attempts to verify the information entered by the user to authenticate the identity of the user. This secure logon is optional, but can enable access to saved preferences or attributes associated with the user such as those contained in a personal account profile, purchase history or saved shopping cart, for example. It can also serve a dual role and eliminate the need for later security/authorization steps, such as steps 1210-1214, in which security information is again provided to permit the web server to access the user's pangenetic data. In enter query for web items step 1206, the user can enter non-pangenetic information, such as search terms or phrases, to compose a search query for retrieving web based information and documents (e.g., web pages). In receive query step 1208 the web server receives the query data entered by the user. Optionally, the web server may also retrieve additional information about the user such as non-pangenetic user attributes stored in an attribute profile associated with the user, where the attribute profile can be items stored in a shopping cart or personal information stored in a user account profile, for example. Next, in request user pangenetic data access authorization step 1210, the web server can request permission from the user to access their pangenetic profile. In enter authorization step 1212, the user can submit authorization information in the form of clicking an authorize button, entering a User_ID and password which authorizes access, submitting an electronic authorization certificate, or supplying input of biometric information, for example. In verify authorization step 1214, the web server verifies the authenticity or correctness of the authorization information supplied by the user by comparing it with an authorization profile of the user stored in the web server's database. In access pangenetic profile of user step 1216, the web server accesses pangenetic data associated with the user which can either be located in a database of the web server, in a separate pangenetic database server, or in a file contained on a computing device with which the user is interfacing with the web server through a network. In access item feedback matrix step 1218, the web server accesses a dataset (e.g., an item feedback matrix) containing correlations between web items and pangenetic attribute combinations. In identify web items matching query and user pangenetics step 1220, the web server identifies web items represented in the item feedback matrix that have the highest non-pangenetic similarity and pangenetic similarity to data associated with the user and their query. This can be achieved by determining for each web item, the quantity of non-pangenetic matches between the non-pangenetic data correlated with that web item and the non-pangenetic data associated with the user query and the quantity of pangenetic matches between the pangenetic data correlated with that web item and the pangenetic data associated with the user. Based on the non-pangenetic and pangenetic similarities that are determined, the web items can be ranked (or scored), and one or more of web items can be selected based on rank (or score) and then transmitted as output in transmit web item listing step 1222, wherein the selection of items for output can be based on a predetermined threshold value applied to rank (or score). In receive listing and provide feedback step 1224, the user receives the transmission indicating one or more web items as web search results, and optionally provides active or passive feedback with respect to one or more of the web items in the search results listing. In store feedback step 1226 the feedback can be stored by the web server and used in the future to update or generate and item feedback matrix, or simply guide future selection of web items for the user who provided the feedback. In logoff step 1228, the user logs out to end the session and thereby terminates secure access to the web server. This logoff step can be automated based on closing the application, a time-out, or moving out of range of an optical sensor or RFID sensor which detects the presence of the authorized user to ensure that an unauthorized user does not inadvertently gain access the consumer's pangenetic data or pangenetic based results, particularly in a public setting where others might attempt to gain access to an individual's pangenetic data through an easily captured mobile device, for example.

In one embodiment, a method for pangenetic based web search can comprise i) receiving non-pangenetic data associated with a user query; ii) accessing pangenetic data associated with the user; iii) accessing a dataset containing pangenetic data and non-pangenetic data correlated with web items; iv) determining for each web item, the quantity of non-pangenetic matches between the non-pangenetic data correlated with that web item and the non-pangenetic data associated with the user query and the quantity of pangenetic matches between the pangenetic data correlated with that web item and the pangenetic data associated with the user; and v) transmitting as output, based on the quantity of non-pangenetic matches and the quantity of pangenetic matches determined for each web item, a listing of at least a portion of the web items as internet search results for the user. In addition to transmitting a listing of the one or more web items to the user, the system can transmit the listing to one or more other users, a database, a dataset, a computer readable memory, a computer readable medium, a computer processor, a computer network, a printout device, a visual display, and a wireless receiver.

In one embodiment of a method for pangenetic based web search, the method can further comprise acts of transmitting an authorization request for access to the pangenetic data associated with the user, and receiving an authorization granting access to the pangenetic data associated with the user. In one embodiment, the pangenetic data associated with the user constitutes a pangenetic profile of the user. In one embodiment, the pangenetic data correlated with the web items can be pangenetic metadata. In one embodiment, the dataset containing pangenetic data and non-pangenetic data can be selected from the group consisting of an internet search engine document index, an internet search engine hitlist, and an internet search engine lexicon dataset. In one embodiment, the dataset containing pangenetic data and non-pangenetic data is a lexicon dataset with pointers to entries in an internet search engine document index containing a hitlist, wherein determining the quantity of matches comprises identifying, from the hitlist, the quantity of non-pangenetic hits and the quantity of pangenetic hits for each web item with respect to the non-pangenetic data associated with the user query and the pangenetic data associated with the user, wherein hits are matches.

In one embodiment of a method for pangenetic based web search, the portion of the web items transmitted as output in the listing is determined by one or more predetermined thresholds applied to the quantity of non-pangenetic matches and the quantity of pangenetic matches determined for each web item. In one embodiment, each web item represented in the listing was determined to have at least one non-pangenetic match. In one embodiment, the listing is a rank listing wherein the rank of each web item in the rank listing is based on the quantity of non-pangenetic matches and the quantity of pangenetic matches determined for each web item. In one embodiment, the portion of the web items transmitted as output consists of web items having a rank within a range defined by at least one predetermined threshold applied to rank. In one embodiment, the rank listing contains two sets of ranks for the web items in the rank listing, the first set of ranks being based on the quantity of non-pangenetic matches, and the second set of ranks being based on the quantity of non-pangenetic matches and the quantity of pangenetic matches. In one embodiment, the rank of each web item in the rank listing is determined by a score computed for each web item based on the quantity of non-pangenetic matches and the quantity of pangenetic matches for each web item. In one embodiment, a score for a web item is computed by using a quantitative similarity measure to determine a non-pangenetic similarity value based on the quantity of non-pangenetic matches and a pangenetic similarity value based on the quantity of pangenetic matches, and then averaging the non-pangenetic similarity value with the pangenetic similarity value to generate the score for the web item. The averaging can be a weighted averaging computation in which a higher weight is given to either the non-pangenetic similarity value or the pangenetic similarity value depending on the type of search, the particular query terms, or the relative importance of non-pangenetic factors versus pangenetic factors in selecting the most relevant results for a user, which can be based on or learned from user feedback regarding satisfaction with past search results.

In one embodiment of a method for pangenetic based web search, the dataset containing pangenetic data and non-pangenetic data correlated with web items also contains context of occurrence values for the pangenetic data and non-pangenetic data correlated with each web item, and the method further comprises steps of i) identifying, with respect to a web item, the non-pangenetic context of occurrence values for each of the non-pangenetic data correlated with the web item which match non-pangenetic data associated with the user query; ii) computing a non-pangenetic score for the web item by combining the non-pangenetic context of occurrence values with the quantity of matches determined for the corresponding non-pangenetic data; iii) identifying, with respect to the web item, the pangenetic context of occurrence values for each of the pangenetic data correlated with the web item which match pangenetic data associated with the user query; iv) computing a pangenetic score for the web item by combining the pangenetic context of occurrence values with the quantity of matches determined for the corresponding pangenetic data; v) determining a final score for the web item by averaging the non-pangenetic score with the pangenetic score; vi) repeating steps (i) to (v) for each of the web items; and vii) determining the rank of each web item based on the final scores determined for the web items.

In one embodiment of a method for pangenetic based web search, the pangenetic data correlated with the web items are derived from statistical associations between item preferences and pangenetic data associated with a group of individuals. In one embodiment, the pangenetic data correlated with the web items are derived by computing statistical associations which indicate the strength of association between the item preferences and pangenetic data associated with a group of individuals. In one embodiment, the pangenetic data correlated with the web items are derived from statistical associations between pangenetic data associated with individuals and online behaviors the individuals exhibit while interacting with the web items. In one embodiment, the pangenetic data correlated with the web items are derived from an item feedback matrix containing correlations between item preferences and pangenetic data associated with a group of individuals.

In one embodiment of a method for pangenetic based web search, the accessing of pangenetic data of the user is in accordance with an applied data mask, the method further comprising i) transmitting an authorization request for access to the pangenetic data associated with the user; ii) receiving an authorization which grants access to the pangenetic data; iii) accessing a data mask, wherein the data mask's parameters are associated with the authorization; and iv) applying the data mask to the pangenetic data.

In one embodiment, a program storage device is provided that is readable by a machine and contains a set of instructions which, when read by the machine, causes execution of a computer based method for providing internet search results for a user, wherein the method comprises i) receiving non-pangenetic data associated with a user query; ii) accessing pangenetic data associated with the user; iii) accessing a dataset containing pangenetic data and non-pangenetic data correlated with web items; iv) determining for each web item, the quantity of non-pangenetic matches between the non-pangenetic data correlated with that web item and the non-pangenetic data associated with the user query and the quantity of pangenetic matches between the pangenetic data correlated with that web item and the pangenetic data associated with the user; and v) transmitting as output, based on the quantity of non-pangenetic matches and the quantity of pangenetic matches determined for each web item, a listing of at least a portion of the web items as internet search results for the user.

In one embodiment, a computer database system for providing internet search results for a user comprises 1) a memory containing a first data structure containing pangenetic data associated with the user, and a second data structure containing pangenetic data and non-pangenetic data correlated with web items; and 2) a processor for: i) receiving non-pangenetic data associated with a user query; ii) accessing the first data structure; iii) accessing the second data structure; iv) determining for each web item, the quantity of non-pangenetic matches between the non-pangenetic data correlated with that web item and the non-pangenetic data associated with the user query and the quantity of pangenetic matches between the pangenetic data correlated with that web item and the pangenetic data associated with the user; and v) transmitting as output, based on the quantity of non-pangenetic matches and the quantity of pangenetic matches determined for each web item, a listing of at least a portion of the web items as internet search results for the user.

Figure 13:
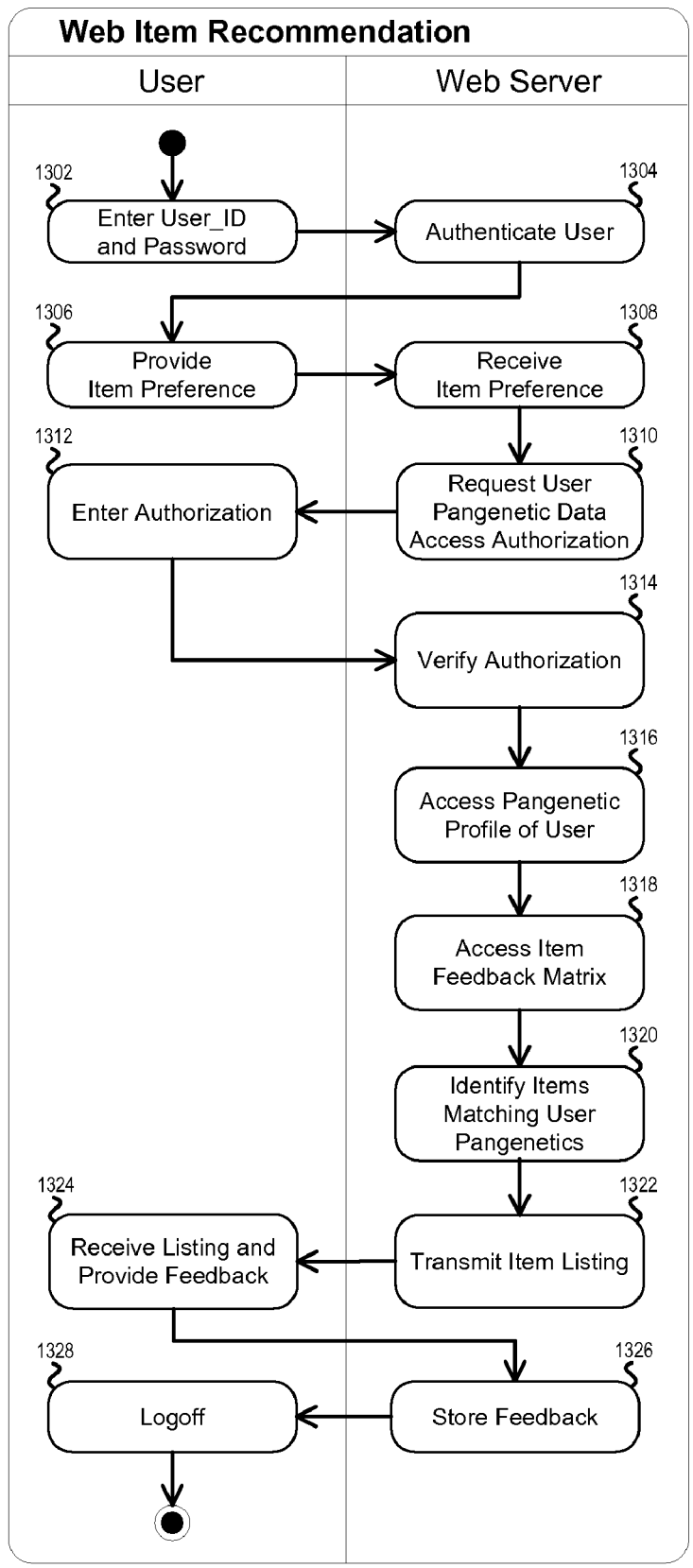
FIG. 13 illustrates an activity diagram depicting pangenetic based web item recommendation.

FIG. 13 illustrates a UML activity diagram depicting one embodiment of a method for pangenetic based online recommendation of items for a user. The method can comprise an enter User_ID and Password step 1302 in which the user can enter information, including biometric information, to logon and authenticate themself to the pangenetic based web server (a pangenetic database system), and an authenticate user step 1304 in which the web server attempts to verify the information entered by the user to authenticate the identity of the user. This secure logon is optional, but can enable access to saved preferences or attributes associated with the user such as those contained in a personal account profile, purchase history or saved shopping cart, for example. It can also serve a dual role and eliminate the need for later security/authorization steps, such as steps 1310-1314, in which security information is again provided to permit the web server to access the user's pangenetic data. In provide item preference step 1306, the user can directly provide non-pangenetic data indicating an item preference by entering a query or clicking a radio button or advertisement, or can indirectly provide the item preference from a personal account profile, purchase history or saved shopping cart. In receive item preference step 1308 the web server receives the non-pangenetic data indicating at least one item preference of the user. Next, in request user pangenetic data access authorization step 1310, the web server can request permission from the user to access their pangenetic profile. In enter authorization step 1312, the user can submit authorization information in the form of clicking an authorize button, entering a User_ID and password which authorizes access, submitting an electronic authorization certificate, or supplying input of biometric information, for example. In verify authorization step 1314, the web server verifies the authenticity or correctness of the authorization information supplied by the user by comparing it with an authorization profile of the user stored in the web server's database. In access pangenetic profile of user step 1316, the web server accesses pangenetic data associated with the user which can either be located in a database of the web server, in a separate pangenetic database server, or in a file contained on a computing device with which the user is interfacing with the web server through a network. In access item feedback matrix step 1318, the web server accesses a dataset (e.g., an item feedback matrix) containing correlations between item preferences and pangenetic attribute combinations. In identify items matching user pangenetics step 1320, the web server identifies item preferences represented in the item feedback matrix that are associated with the item preference of the user and have high enough pangenetic similarity to the user to be considered a match for the user. This can be achieved by determining the quantity of pangenetic attribute matches between the user and each relevant item preferences in the feedback matrix and selecting one or more item preferences having the highest number of matches, or by computing a pangenetic similarity value for each item preference to obtain normalized values for cross-comparison and then applying a predetermined threshold value to the pangenetic similarity value determined for each item preference in order to enable selection of one or more item preferences having the highest pangenetic similarity values. The web server can also output item preferences having low values to indicate non-recommended items, which indirectly indicates other items as recommended items that the user should focus on instead. Based on the quantity of pangenetic attribute matches determined for each item preference (or based on a pangenetic similarity score/value computed based on the quantity of matches), the item preferences can be ranked, and one or more of ranked item preferences can be selected based on rank and then transmitted as output in transmit item listing step 1322, wherein the selection of item preferences for output can be based on a predetermined threshold value applied to rank. In receive listing and provide feedback step 1324, the user receives the transmission which indicates the one or more recommended items, and optionally provides active or passive feedback with respect to one or more of those items. In store feedback step 1326 the feedback can be stored by the web server and used in the future to update or generate and item feedback matrix, or simply guide future selection of item preferences for the user who provided the feedback. In logoff step 1328, the user logs out to end the session and thereby terminates secure access to the web server. This logoff step can be automated based on closing the application, a timeout, or moving out of range of an optical sensor or RFID sensor which detects the presence of the authorized user to ensure that an unauthorized user does not inadvertently gain access the consumer's pangenetic data or pangenetic based results, particularly in a public setting where others might attempt to gain access to an individual's pangenetic data through an easily captured mobile device, for example.

In one embodiment, a method for pangenetic based online recommendation of items comprises i) receiving at least one item preference associated with the user; ii) accessing pangenetic data associated with the user; iii) accessing a dataset containing item preferences of individuals who also share the at least one item preference associated with the user, wherein pangenetic data of the individuals are correlated with the item preferences; iv) determining for each item preference, the quantity of matches between the pangenetic data associated with that item preference and the pangenetic data associated with the user; and v) transmitting as output, based on the quantity of matches determined for each item preference, a listing of at least a portion of the item preferences to indicate recommended items for the user. In addition to transmitting a listing of item preferences to the user, the system can transmit the listing to one or more other users, a database, a dataset, a computer readable memory, a computer readable medium, a computer processor, a computer network, a printout device, a visual display, and a wireless receiver.

In one embodiment, a method for pangenetic based online recommendation of items for a user can further comprise transmitting, as output, at least a portion of the item preferences to indicate non-recommended items for the user. In one embodiment, the pangenetic data associated with the user constitutes a pangenetic profile of the user. In one embodiment, the pangenetic data correlated with the item preferences are combinations of pangenetic data selected from pangenetic profiles of the individuals. In one embodiment, the pangenetic data correlated with the item preferences are pangenetic metadata. In one embodiment, the item preferences are ratings that indicate levels of satisfaction with the items indicated by the item preferences. In one embodiment, the ratings are average ratings of the items by the individuals. In one embodiment, the method can further comprise receiving one or more non-pangenetic attributes associated with the user, wherein the one or more non-pangenetic attributes associated with the user match one or more non-pangenetic attributes associated with the individuals. In one embodiment, the method can further comprise the steps of i) transmitting an authorization request for access to the pangenetic data associated with the user, and ii) receiving an authorization granting access to the pangenetic data associated with the user.

In one embodiment of a method for pangenetic based online recommendation of items for a user, the portion of the item preferences transmitted as output can be determined by a predetermined threshold applied to the quantity of matches determined for each item preference. In one embodiment, the listing is a rank listing, and wherein the rank of each item preference in the rank listing is based on the quantity of matches determined for each item preference. In one embodiment, the item preferences transmitted as output consists of item preferences having a rank within a range defined by at least one predetermined threshold applied to rank. In one embodiment, the rank of each item preference represented in the rank listing is determined by a score computed for each item preference based on the quantity of matches determined for each item preference. In one embodiment, the score for each item preference is computed using a quantitative similarity measure applied to the pangenetic data.

In one embodiment of a method for pangenetic based online recommendation of items for a user, the correlations between the pangenetic data and the item preferences contained in the dataset are previously determined based on statistical associations between item preferences and pangenetic data associated with the individuals. In one embodiment, the correlations between the pangenetic data and the item preferences contained in the dataset are determined by computing statistical associations which indicate the strength of association between item preferences and pangenetic data associated with the individuals. In one embodiment, the correlations between the pangenetic data and the item preferences contained in the dataset are determined by computing statistical associations between pangenetic data of individuals and online behaviors which indicate the item preferences of the individuals. In one embodiment, the dataset is an item feedback matrix.

In one embodiment of a method for pangenetic based online recommendation of items for a user, the method further comprises acts of i) receiving item preference data associated with the individuals, wherein the item preference data indicates item preferences of the individuals; ii) accessing pangenetic data associated with the individuals; iii) determining correlations between the item preference data and the pangenetic data associated with the individuals; and iv) storing the correlations between the item preference data and the pangenetic data to generate an item feedback matrix.

In one embodiment of a method for pangenetic based online recommendation of items for a user, the method further comprises acts of i) transmitting an authorization request for access to the pangenetic data associated with the user; ii) receiving an authorization which grants access to the pangenetic data; iii) accessing a data mask, wherein the data mask's parameters are associated with the authorization; and iv) applying the data mask to the pangenetic data.

In one embodiment of a method for pangenetic based online recommendation of items for a user, wherein the dataset comprises data records containing the item preferences of the individuals, the method further comprises acts of i) identifying one or more clusters of data records, wherein within each cluster the data records share a similar pattern of item preferences as determined by a quantitative similarity measure; ii) determining, by statistical association, pangenetic data that correlate with each of the one or more clusters; and iii) identifying, by using a quantitative similarity measure, the cluster having the highest pangenetic similarity to the user to provide the portion of the item preferences to be transmitted as output. In a further embodiment, the item preferences of the identified cluster comprise item rating values that are averaged prior to transmission as output. In another embodiment, the item preferences identified for transmission as output are a subset of item preferences selected from the identified cluster based on an item category relationship with the at least one item preference associated with the user.

In one embodiment of a method for pangenetic based online recommendation of items for a user, wherein the dataset comprises data records containing the item preferences of the individuals, and wherein the item preferences comprise item rating values, the method further comprises acts of i) identifying one or more clusters of data records, wherein within each cluster the data records share a similar pattern of item preferences as determined by a quantitative similarity measure; ii) determining, by statistical association, pangenetic data that correlate with each of the one or more clusters; iii) identifying, by using a quantitative similarity measure, the cluster having the highest pangenetic similarity to the user; and iv) identifying, by using a quantitative similarity measure within the cluster having the highest pangenetic similarity to the user, a subcluster of data records having the most similar pattern of item preferences to the user to provide the portion of the item preferences to be transmitted as output. In a further embodiment, the item preferences of the identified subcluster comprise item rating values that are averaged prior to transmission as output.

In one embodiment, a program storage device is provided that is readable by a machine and contains a set of instructions which, when read by the machine, causes execution of a computer based method for online recommendation of items for a user, wherein the method comprises i) receiving at least one item preference associated with the user; ii) accessing pangenetic data associated with the user; iii) accessing a dataset containing item preferences of individuals who also share the at least one item preference associated with the user, wherein pangenetic data of the individuals are correlated with the item preferences; iv) determining for each item preference, the quantity of matches between the pangenetic data correlated with that item preference and the pangenetic data associated with the user; and v) transmitting as output, based on the quantity of matches determined for each item preference, a listing of at least a portion of the item preferences to indicate recommended items for the user.

In one embodiment, a computer database system for online recommendation of items for a user can comprise 1) a memory containing a first data structure containing pangenetic data associated with the user, and a second data structure containing item preferences of individuals who also share at least one item preference associated with the user, wherein pangenetic data of the individuals are correlated with the item preferences; and 2) a processor for i) receiving the at least one item preference associated with the user; ii) accessing the first data structure; iii) accessing the second data structure; iv) determining for each item preference, the quantity of matches between the pangenetic data correlated with that item preference and the pangenetic data associated with the user; and v) transmitting as output, based on the quantity of matches determined for each item preference, a listing of at least a portion of the item preferences to indicate recommended items for the user.

Figure 14:
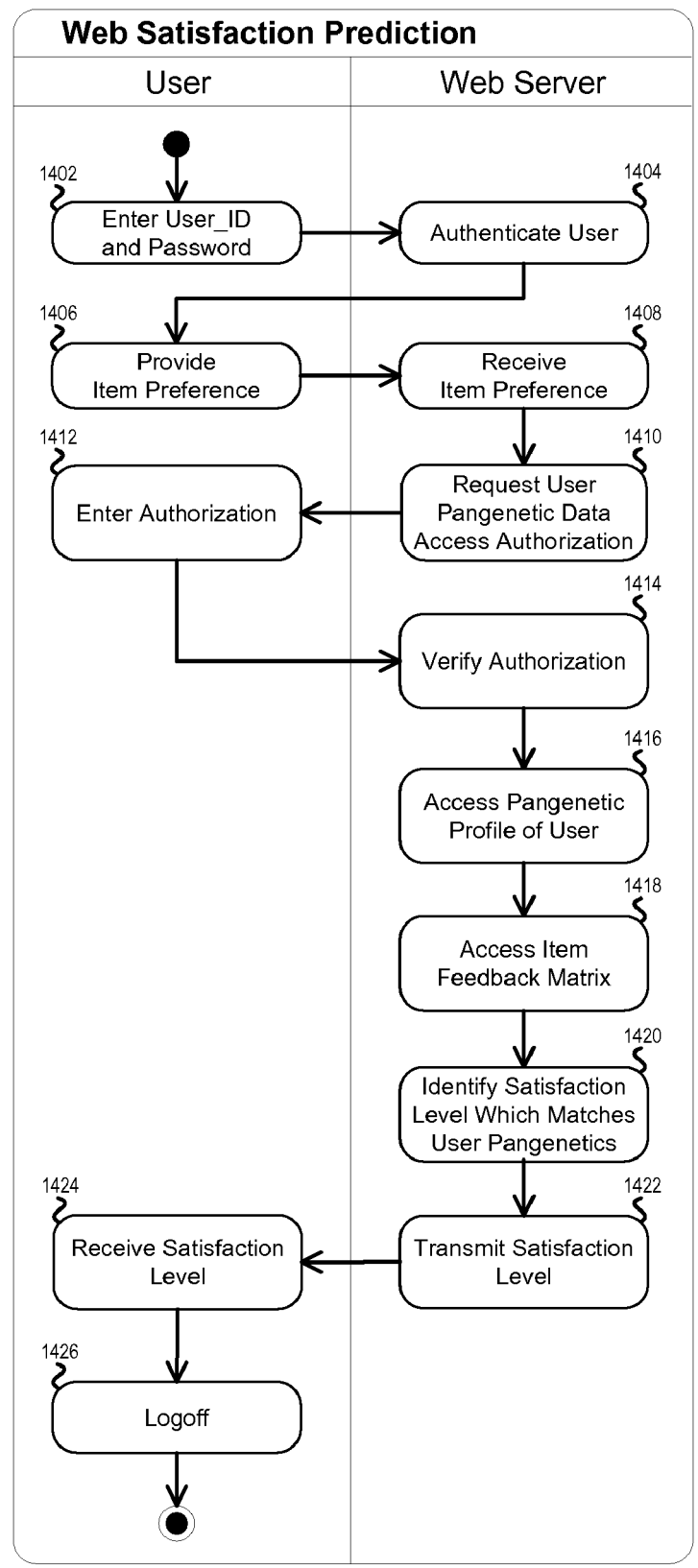
FIG. 14 illustrates an activity diagram depicting pangenetic based web satisfaction prediction.

FIG. 14 illustrates a UML activity diagram depicting one embodiment of a method for pangenetic based web satisfaction prediction (online prediction of user satisfaction with an item). The method can comprise an enter User_ID and Password step 1402 in which the user can enter information, including biometric information, to logon and authenticate themself to the pangenetic based web server (a pangenetic database system), and an authenticate user step 1404 in which the web server attempts to verify the information entered by the user to authenticate the identity of the user. This secure logon is optional, but can enable access to saved preferences or attributes associated with the user such as those contained in a personal account profile, purchase history or saved shopping cart, for example. It can also serve a dual role and eliminate the need for later security/authorization steps, such as steps 1410-1414, in which security information is again provided to permit the web server to access the user's pangenetic data. In provide item preference step 1406, the user can directly provide non-pangenetic data indicating at least one item preference by entering a query or clicking a radio button or advertisement, or can indirectly provide the item preference from a personal account profile, purchase history or saved shopping cart, for example. In receive item preference step 1408 the web server receives the non-pangenetic data indicating at least one item preference of the user. Next, in request user pangenetic data access authorization step 1410, the web server can request permission from the user to access their pangenetic profile. In enter authorization step 1412, the user can submit authorization information in the form of clicking an authorize button, entering a User_ID and password which authorizes access, submitting an electronic authorization certificate, or supplying input of biometric information, for example. In verify authorization step 1414, the web server verifies the authenticity or correctness of the authorization information supplied by the user by comparing it with an authorization profile of the user stored in the web server's database. In access pangenetic profile of user step 1416, the web server accesses pangenetic data associated with the user which can either be located in a database of the web server, in a separate pangenetic database server, or in a file contained on a computing device with which the user is interfacing with the web server through a network. In access item feedback matrix step 1418, the web server accesses a dataset (e.g., an item feedback matrix) containing correlations between different pangenetic attribute combinations and one or more levels of satisfaction (i.e., satisfaction levels) associated with the item preference of the user. In identify satisfaction level which matches user pangenetics step 1420, the web server identifies the level of satisfaction having the highest pangenetic similarity to the user. This can be achieved by determining the quantity of pangenetic attribute matches between the user and each relevant satisfaction level represented in the feedback matrix and selecting the satisfaction level having the highest number of matches, or by computing a pangenetic similarity value for each satisfaction level to obtain normalized values for cross-comparison and then selecting the satisfaction level having the highest value as the predicted level of satisfaction the user will experience with the item indicated by their item preference. The selected level of satisfaction can be transmitted as output in transmit satisfaction level step 1422. In receive satisfaction level step 1424, the user receives the transmission indicating the level of satisfaction the web server predicts they will experience with respect to the item preference. In logoff step 1426, the user logs out to end the session and thereby terminates secure access to the web server. This logoff step can be automated based on closing the application, a time-out, or moving out of range of an optical sensor or RFID sensor which detects the presence of the authorized user to ensure that an unauthorized user does not inadvertently gain access the consumer's pangenetic data or pangenetic based results, particularly in a public setting where others might attempt to gain access to an individual's pangenetic data through an easily captured mobile device, for example.

In one embodiment, a method for online prediction of user satisfaction with an item comprises i) receiving at least one item preference associated with a user; ii) accessing pangenetic data associated with the user; iii) accessing a dataset containing one or more levels of satisfaction associated with the at least one item preference, wherein pangenetic data are correlated with the one or more levels of satisfaction; iv) determining for each level of satisfaction, the quantity of matches between the pangenetic data correlated with that level of satisfaction and the pangenetic data associated with the user; and v) transmitting as output, based on the quantity of matches determined for each level of satisfaction, a level of satisfaction the user is predicted to experience with respect to the at least one item preference. In addition to transmitting a listing the predicted satisfaction level to the user, the system can transmit the predicted satisfaction level to one or more other users, a database, a dataset, a computer readable memory, a computer readable medium, a computer processor, a computer network, a printout device, a visual display, and a wireless receiver.

In one embodiment of a method for online prediction of user satisfaction with an item, the level of satisfaction for which the largest quantity of matches is determined is the satisfaction level the user is predicted to experience. In one embodiment, the method further comprises computing a score for each level of satisfaction using a quantitative similarity measure that processes the quantity of matches, and selecting the level of satisfaction having the highest score as the level of satisfaction the user is predicted to experience. In one embodiment, the pangenetic data correlated with the one or more levels of satisfaction are pangenetic metadata. In one embodiment, the pangenetic data associated with the user constitutes a pangenetic profile of the user. In one embodiment, the pangenetic data correlated with the one or more levels of satisfaction are combinations of pangenetic data selected from pangenetic profiles associated with a group of individuals. In one embodiment, the levels of satisfaction are the average levels of satisfaction of a group of individuals. In one embodiment, the method further comprises receiving one or more non-pangenetic attributes associated with the user, wherein the one or more non-pangenetic attributes associated with the user match one or more non-pangenetic attributes associated with the group of individuals. In one embodiment, the method further comprises the steps of transmitting an authorization request for access to the pangenetic data associated with the user, and receiving an authorization granting access to the pangenetic data associated with the user.

In one embodiment of a method for online prediction of user satisfaction with an item, the correlations between the pangenetic data and the one or more levels of satisfaction contained in the dataset are previously determined based on statistical associations between levels of satisfaction and pangenetic data associated with a group of individuals. In one embodiment, the correlations between the pangenetic data and the one or more levels of satisfaction contained in the dataset are determined by computing statistical associations which indicate the strength of association between levels of satisfaction and pangenetic data associated with a group of individuals. In one embodiment, the correlations between the pangenetic data and the one or more levels of satisfaction contained in the dataset are determined by computing statistical associations between pangenetic data of individuals and online behaviors which indicate levels of satisfaction of the individuals. In one embodiment, the correlations between the pangenetic data and the one or more levels of satisfaction contained in the dataset comprise statistical associations indicating level of certainty, and wherein a level of certainty that the user will experience the predicted level of satisfaction is also transmitted as output.

In one embodiment of a method for online prediction of user satisfaction with an item, the dataset is an item feedback matrix and the method further comprises i) receiving level of satisfaction data associated with a group of individuals, wherein the level of satisfaction data indicates levels of satisfaction of the individuals with the at least one item preference; ii) accessing pangenetic data associated with the individuals; iii) determining correlations between the levels of satisfaction of the individuals and the pangenetic data associated with the individuals; and iv) storing the correlations between the levels of satisfaction and the pangenetic data to generate an item feedback matrix.

In one embodiment of a method for online prediction of user satisfaction with an item, accessing of the pangenetic data associated with the user is in accordance with an applied data mask and the method further comprises i) transmitting an authorization request for access to the pangenetic data associated with the user; ii) receiving an authorization which grants access to the pangenetic data; iii) accessing a data mask, wherein the data mask's parameters are associated with the authorization; and iv) applying the data mask to the pangenetic data.

In one embodiment, a program storage device is provided that is readable by a machine and contains a set of instructions which, when read by the machine, causes execution of a computer based method for online prediction of user satisfaction with an item, wherein the method comprises i) receiving at least one item preference associated with a user; ii) accessing pangenetic data associated with the user; iii) accessing a dataset containing one or more levels of satisfaction associated with the at least one item preference, wherein pangenetic data are correlated with the one or more levels of satisfaction; iv) determining for each level of satisfaction, the quantity of matches between the pangenetic data correlated with that level of satisfaction and the pangenetic data associated with the user; and v) transmitting as output, based on the quantity of matches determined for each level of satisfaction, a level of satisfaction the user is predicted to experience with respect to the at least one item preference.

In one embodiment, a computer database system for online prediction of user satisfaction with an item comprises 1) a memory containing a first data structure containing pangenetic data associated with the user, and a second data structure containing one or more levels of satisfaction associated with at least one item preference associated with the user, wherein pangenetic data are correlated with the one or more levels of satisfaction; and 2) a processor for i) receiving the at least one item preference associated with the user; ii) accessing the first data structure; iii) accessing the second data structure; iv) determining for each level of satisfaction, the quantity of matches between the pangenetic data correlated with that level of satisfaction and the pangenetic data associated with the user; and v) transmitting as output, based on the quantity of matches determined for each level of satisfaction, a level of satisfaction the user is predicted to experience with respect to the at least one item preference.

Figure 15:
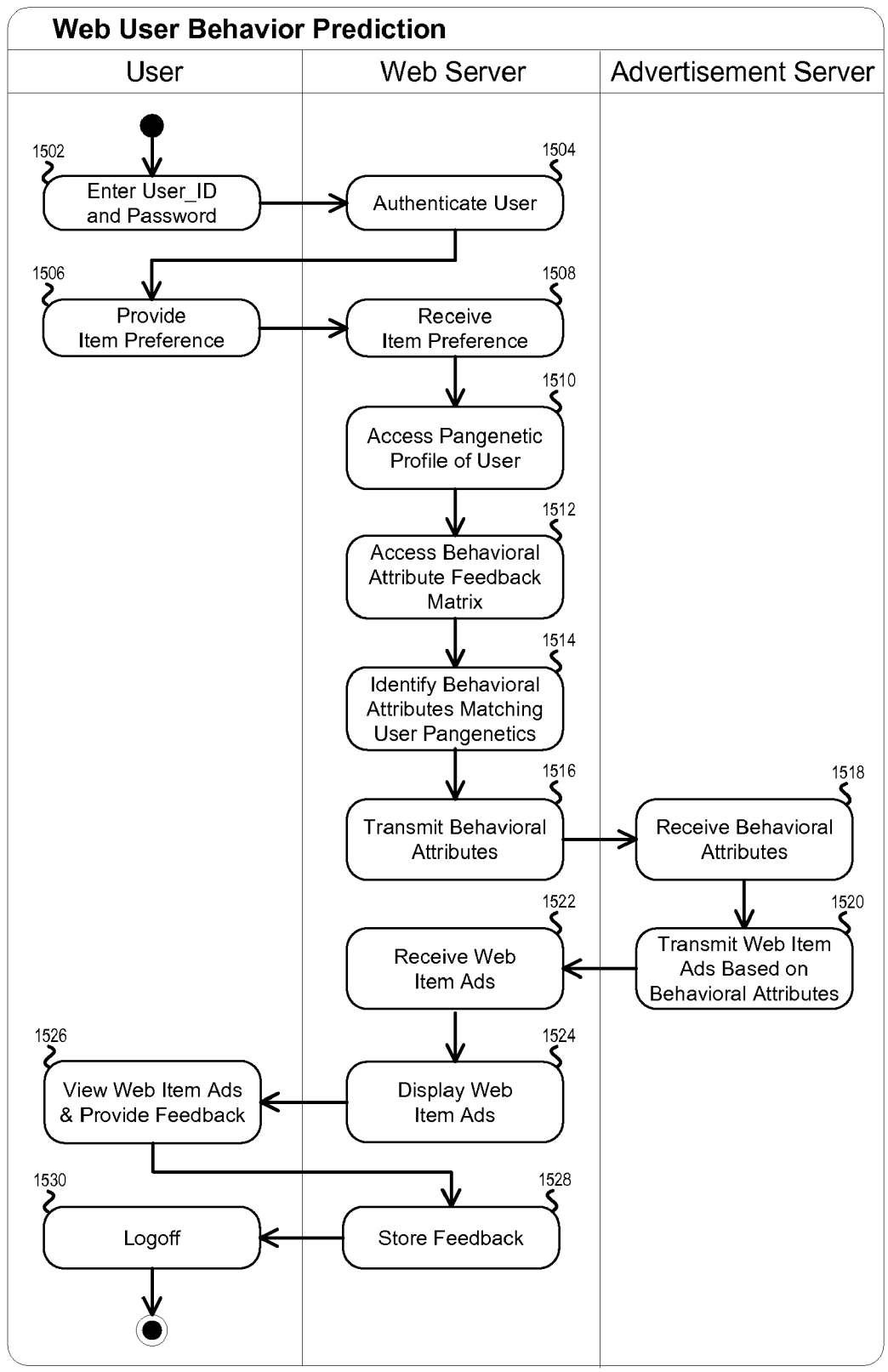
FIG. 15 illustrates an activity diagram depicting pangenetic based web user behavior prediction.

FIG. 15 illustrates a UML activity diagram depicting one embodiment of a method for pangenetic based prediction of web user behavior. The method can comprise an enter User_ID and Password step 1502 in which the user can enter information, including biometric information, to logon and authenticate themselves to the pangenetic based web server (a pangenetic database system), and an authenticate user step 1504 in which the web server attempts to verify the information entered by the user to authenticate the identity of the user. This secure logon is optional, but can enable access to saved preferences or attributes associated with the user such as those contained in a personal account profile, purchase history or saved shopping cart, for example. It can also serve a dual role and eliminate the need for later security/authorization steps in which security information is again provided to permit the web server to access the user's pangenetic data. In provide item preference step 1506, the user can provide non-pangenetic data through their actions which indicate a behavior towards a presented web item. In receive item preference step 1508 the web server receives the non-pangenetic data indicating the behavior of the user towards the web item. In access pangenetic profile of user step 1510, the web server accesses pangenetic data associated with the user which can either be located in a database of the web server, in a separate pangenetic database server, or in a file contained on a computing device with which the user is interfacing with the web server through a network. In access behavioral attribute feedback matrix step 1512, the web server accesses a dataset (e.g., a pangenetic based behavioral item feedback matrix) containing correlations between different pangenetic attribute combinations and behavioral attributes (i.e., non-pangenetic attributes indicating user behaviors) that are associated with the item preference of the user. In identify behavioral attributes matching user pangenetics step 1514, the web server identifies one or more behavioral attributes (behavioral items) correlated with pangenetic attributes having the highest pangenetic similarity to the user's pangenetic profile. This can be achieved by determining the quantity of pangenetic attribute matches between the user and each behavioral attribute represented in the feedback matrix and selecting the behavioral having the highest number of matches, or by computing a pangenetic similarity value for each behavioral attribute to obtain normalized values for cross-comparison and then selecting the behavioral attribute having the highest value as the behavior the user is predicted to exhibit. Alternatively, a plurality of behavioral attributes can be selected based on at least one predetermined threshold value applied to quantity of matches or pangenetic similarity values determined for the behavioral attributes. The selected one or more behavioral attributes can be transmitted as output in transmit behavioral attributes step 1516. Additionally, if the behavioral item feedback matrix contains correlations indicating or associated with values (e.g., statistical values, scores) indicating level of certainty, probability or likelihood of the user to exhibit the behavioral attributes, those values can be transmitted with the behavioral attributes. In receive behavioral attributes step 1518, another web server such as an advertisement server can receive the transmission of behavioral attributes indicating behaviors predicted for the user. While an advertisement server is illustrated in this example, the server could be of other types and for purposes other than selecting advertisements, and the server function could be integrated within the pangenetic based web server itself. In this embodiment, the advertisement server can use the behavioral attributes to search its database for ads correlated with the received behavioral attributes. Similar to an item feedback matrix, ads that have the strongest correlation with the received behavioral data can be selected for the user. In transmit web item ads based on behavioral attributes step 1520, the one or more selected ads are transmitted to the pangenetic based web server. In received web item ads step 1522, the web server receives the web ads from the advertisement server. In display web item ads step 1524 the web server displays the web ads to the user. In view item ads and provide feedback step 1526, the user views the displayed web ads and can provide active feedback. or alternatively, passive user feedback can be collected by the web server by monitoring the behavioral response of the user to the displayed ads. In store feedback step 1528 the web server stores the feedback obtained from the user. In logoff step 1530, the user logs out to end the session and thereby terminates secure access to the web server. This logoff step can be automated based on closing the application, a time-out, or moving out of range of an optical sensor or RFID sensor which detects the presence of the authorized user to ensure that an unauthorized user does not inadvertently gain access the consumer's pangenetic data or pangenetic based results, particularly in a public setting where others might attempt to gain access to an individual's pangenetic data through an easily captured mobile device, for example. In one embodiment, the advertisement server could be similar to Google's AdWords server.

In one embodiment, a method for pangenetic web based prediction of user behavior comprises i) receiving at least one item preference of a user; ii) accessing pangenetic data associated with the user; iii) accessing a dataset containing one or more non-pangenetic attributes associated with the at least one item preference of the user, wherein pangenetic data are correlated with the one or more non-pangenetic attributes and each non-pangenetic attribute indicates a user behavior; iv) determining for each non-pangenetic attribute, the quantity of matches between the pangenetic data correlated with that non-pangenetic attribute and the pangenetic data associated with the user; and v) transmitting as output, based on the quantity of matches determined for each non-pangenetic attribute, at least one non-pangenetic attribute to indicate at least one behavior predicted for the user. The transmission can be to any of several destinations including the user, one or more other users, a database, a dataset, a computer readable memory, a computer readable medium, a computer processor, a computer network, a printout device, a visual display, and a wireless receiver. In one embodiment, the at least one non-pangenetic attribute transmitted as output is used for a task selected from the group consisting of selecting data for retrieval, selecting data for visual display, selecting the locations of data in a visual display, formulating a internet search query, and selecting web based items for recommendation to a user.

In one embodiment of a method for pangenetic web based prediction of user behavior, the non-pangenetic attribute having the largest quantity of pangenetic matches with the user is the at least one non-pangenetic attribute transmitted as output. In one embodiment, the method further comprises computing a score for each non-pangenetic attribute using a quantitative similarity measure that processes the quantity of matches, and selecting the non-pangenetic attribute having the highest score for transmission as output.

In one embodiment of a method for pangenetic web based prediction of user behavior the pangenetic data correlated with the one or more non-pangenetic attributes are pangenetic metadata. In one embodiment, the pangenetic data associated with the user constitutes a pangenetic profile of the user. In one embodiment, the pangenetic data correlated with the one or more non-pangenetic attributes are combinations of pangenetic data selected from pangenetic profiles associated with a group of individuals. In one embodiment, the method further comprises receiving one or more non-pangenetic attributes associated with the user, wherein the one or more non-pangenetic attributes associated with the user match one or more non-pangenetic attributes associated with the group of individuals. In one embodiment, the quantity of matches determined for each non-pangenetic attribute is used to compute a pangenetic similarity value for each non-pangenetic attribute, wherein non-pangenetic attributes having pangenetic similarity values meeting a predetermined threshold value are transmitted as output. In one embodiment, the method further comprises transmitting an authorization request for access to the pangenetic data associated with the user, and receiving an authorization granting access to the pangenetic data associated with the user. In one embodiment, the accessing of pangenetic data associated with the user is performed in accordance with an applied data mask, wherein the method further comprises i) transmitting an authorization request for access to the pangenetic data associated with the user; ii) receiving an authorization which grants access to the pangenetic data; iii) accessing a data mask, wherein the data mask's parameters are associated with the authorization; and iv) applying the data mask to the pangenetic data.

In one embodiment of a method for pangenetic web based prediction of user behavior, the associations between the pangenetic data and the one or more non-pangenetic attributes contained in the dataset are previously determined based on statistical associations between non-pangenetic attributes and pangenetic data associated with a group of individuals. In one embodiment, the correlations between the pangenetic data and the one or more non-pangenetic attributes contained in the dataset are determined by the results of computing statistical associations which indicate the strength of association between non-pangenetic attributes and pangenetic data associated with a group of individuals. In one embodiment, the pangenetic data and the one or more non-pangenetic attributes contained in the dataset comprise statistical associations indicating level of certainty, and a level of certainty that the user will exhibit the predicted behavior is also transmitted as output.

In one embodiment of a method for pangenetic web based prediction of user behavior, the dataset is an item feedback matrix and the method further comprises i) receiving non-pangenetic attribute data associated with a group of individuals, wherein the non-pangenetic attribute data indicate behaviors of the individuals with respect to the at least one item preference; ii) accessing pangenetic data associated with the individuals; iii) determining correlations between the non-pangenetic attribute data and the pangenetic data associated with the individuals; and iv) storing the correlations between the non-pangenetic attribute data and the pangenetic data to generate an item feedback matrix.

In one embodiment, a program storage device is provided that is readable by a machine and contains a set of instructions which, when read by the machine, causes execution of a computer based method for predicting user behavior, wherein the method comprises i) receiving at least one item preference of a user; ii) accessing pangenetic data associated with the user; iii) accessing a dataset containing one or more non-pangenetic attributes associated with the at least one item preference of the user, wherein pangenetic data are correlated with the one or more non-pangenetic attributes and each non-pangenetic attribute indicates a user behavior; iv) determining for each non-pangenetic attribute, the quantity of matches between the pangenetic data correlated with that non-pangenetic attribute and the pangenetic data associated with the user; and v) transmitting as output, based on the quantity of matches determined for each non-pangenetic attribute, at least one non-pangenetic attribute to indicate at least one behavior predicted for the user.

In one embodiment, a computer database system for predicting user behavior comprises 1) a memory containing a first data structure containing pangenetic data associated with a user, and a second data structure containing one or more non-pangenetic attributes associated with at least one item preference of the user, wherein pangenetic data are correlated with the one or more non-pangenetic attributes and each non-pangenetic attribute indicates a user behavior; and 2) a processor for i) receiving the at least one item preference associated with the user; ii) accessing the first data structure; iii) accessing the second data structure; iv) determining for each non-pangenetic attribute, the quantity of matches between the pangenetic data correlated with that non-pangenetic attribute and the pangenetic data associated with the user; and v) transmitting as output, based on the quantity of matches determined for each non-pangenetic attribute, at least one non-pangenetic attribute to indicate at least one behavior predicted for the user.

Mobile devices (i.e., wireless computing and communications devices) can be utilized advantageously by consumers and other users for web based pangenetic data transactions because they can provide the ability to immediately request access to pangenetic information, authenticate themselves on the system, allow approval for access to the pangenetic information, and receive transmitted authorizations, approvals or denials with respect to selection of and payment for various products and services, for example. However, use of mobile devices place additional requirements on the system due to security concerns and memory limitations.

In terms of security and authentication, the mobile device may use any number of encryption techniques including but not limited to Wired Equivalent Privacy (WEP) encryption, Wi-Fi Protected Access (WPA), Temporal Key Integrity Protocol (TKIP), Lightweight Extensible Authentication Protocol (LEAP), Remote Authentication Dial In User Service (RADIUS), and WLAN Authentication and Privacy Infrastructure. In addition, the mobile devices may use one or more physical types of security including but not limited to smart cards and/or USB tokens. Software tokens may also be used as a form of security.

Additionally with respect to authentication, the mobile device may base authentication on simple password based authentication, biometric identification (e.g. fingerprint recognition or retinal scan) or combinations thereof. Additionally, hardware type solutions may be used in which smart cards, identification chips, or other devices personally associated with the user are utilized in part or wholly for identification and/or authentication. The authorization interface in the mobile device provides the appropriate combination of authentication protocols and procedures to insure that only an authorized individual is authenticated.

In addition to the secure connections, which may be established between the wireless devices and access nodes, pangenetic servers or web service provider servers, Virtual Private Networks (VPNs) can be used to establish secure end-to-end connections between devices. In one embodiment, wireless security is utilized to establish a secure connection to a server, and a VPN is subsequently established to ensure secure transmission along the entire data path. Similarly, a VPN may be established between the user mobile device and a web server, and a VPN may be established between the web server and a pangenetic data server.

In order to minimize data storage requirements at the mobile devices as well as to limit the amount of pangenetic data that is exposed to the wireless link, in one embodiment little or no pangenetic data is transmitted to the mobile units, but rather is transferred, after appropriate masking, from the pangenetic database server to the web server. In a further embodiment, a second "wireless mask" is utilized to allow the transmission of small amounts of critical pangenetic data to a mobile device. In one embodiment, key segments of the pangenetic information can be viewed through an appropriate presentation or Graphical User Interface (GUI). For example, a consumer or their physician may be seeking web based treatment information for a particular ailment and want to know the overlap of key pangenetic data with other individuals having the ailment. In one embodiment, a comparison of a large amount of masked pangenetic data is performed and used by a web search system to determine the appropriateness of web based information and/or item offerings for a consumer. The consumer may then receive, on their wireless device, a transmission of the key overlapping pangenetic attributes that represent the particular pangenetic attributes shared in common between the consumer making the inquiry (i.e., query, or request) and other consumers who found the information or item offers to be satisfactory. In one embodiment, a second wireless mask is used to reduce the amount of data transmitted. In an alternate embodiment, a mathematical or statistical method is used to determine what subset of pangenetic data should be transmitted to the mobile units. The above functionalities also apply to non-medical applications of the system.

Figure 16:
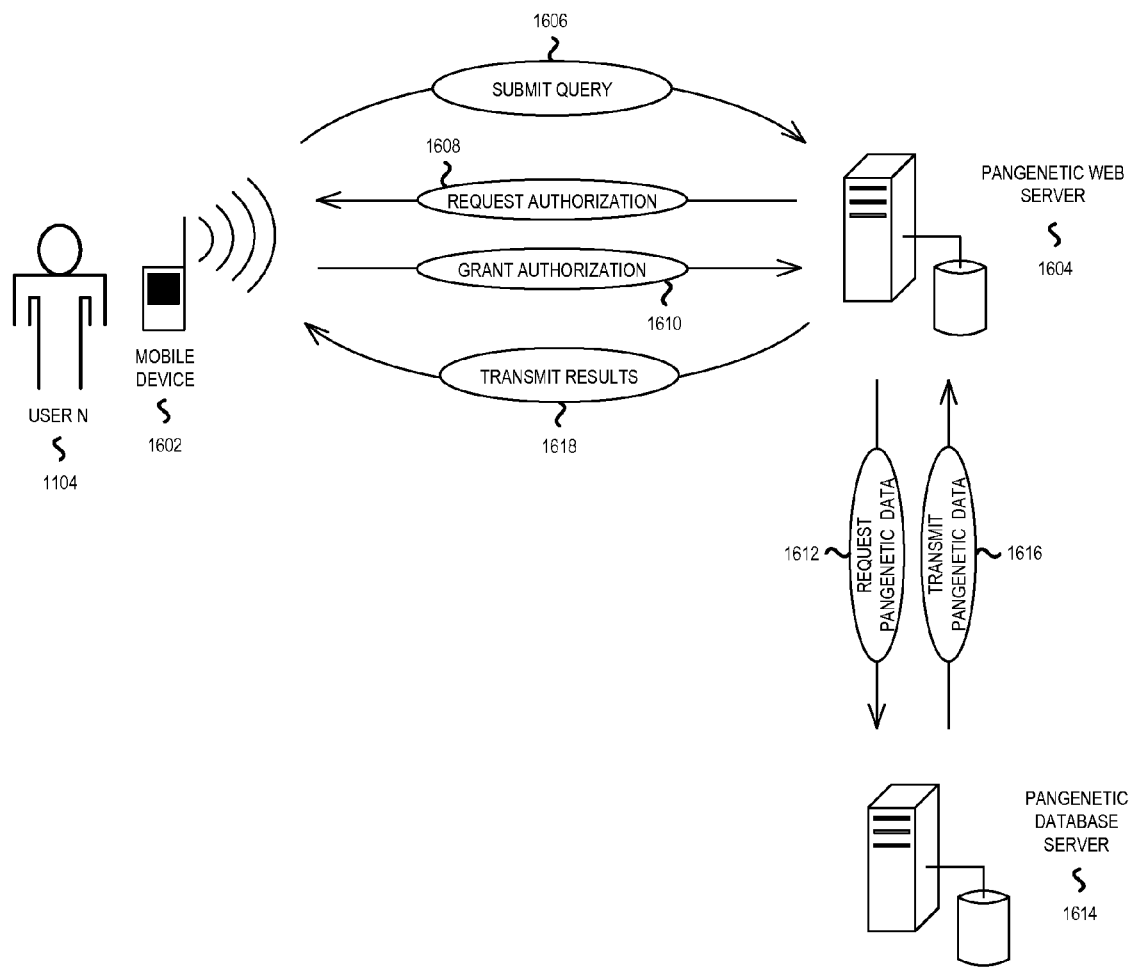
FIG. 16 illustrates a pangenetic based web search, recommendation and prediction database system for a mobile environment.

FIG. 16 illustrates a UML use case diagram depicting one embodiment of a pangenetic based web search, recommendation and prediction database system for a mobile environment. In the embodiment depicted, user N 1104 uses mobile device 1602 to submit a query comprising a web search request, an item recommendation request, a satisfaction prediction request, or a request to access their pangenetic data to pangenetic web server 1604, in submit query use case 1606. In request authorization use case 1608, the pangenetic web server 1604 can request authorization granting access to the pangenetic data profile associated with user N 1104. In grant authorization use case 1610, user N 1104 can utilize mobile device 1602 to transmit an authorization which can comprise authentication/security information to grant authorization to pangenetic web server 1604 to access their pangenetic data. In request pangenetic data use case 1612, the pangenetic web server 1604 can request access to pangenetic data stored on pangenetic database server 1614, where access can be in accordance with one or more data masks as appropriate. In transmit pangenetic data use case 1616, the pangenetic data is either accessed and read by pangenetic web server 1604 directly from the memory of pangenetic database server 1614, or received as a file or datastream. Pangenetic web server 1604 can then utilize the pangenetic data in a method of pangenetic based web search, item recommendation, satisfaction prediction or user behavior prediction. In transmit results use case 1618, the results determined by pangenetic web server 1604 through one of the preceding methods can be transmitted to the mobile device 1602 of user N 1104. Although not indicated in this diagram, the results can be displayed, stored or further processed by mobile device 1602, and user N 1104 can respond to the results received by providing feedback to pangenetic web server 1604, for example.

In one embodiment, a mobile computing device for providing internet search results to a user comprises 1) a transmitter for sending, to a second computing device via a network, one or more transmissions of non-pangenetic data associated with a user query and an authorization granting access to pangenetic data associated with the user, whereupon receipt of the one or more transmissions via the network causes the second computing device to execute steps of i) accessing the pangenetic data associated with the user; ii) accessing a dataset (e.g., an item feedback matrix) containing pangenetic data and non-pangenetic data correlated with web items; iii) determining for each web item, the quantity of non-pangenetic matches between the non-pangenetic data correlated with that web item and the non-pangenetic data associated with the user query and the quantity of pangenetic matches between the pangenetic data correlated with that web item and the pangenetic data associated with the user; and 2) a receiver for receiving from the network, based on the quantity of non-pangenetic matches and the quantity of pangenetic matches determined for each web item, output comprising a listing of at least a portion of the web items as internet search results for the user.

In one embodiment, a mobile computing device for online recommendation of items for a user comprises 1) a transmitter for sending, to a second computing device via a network, one or more transmissions of at least one item preference associated with the user and an authorization granting access to pangenetic data associated with the user, whereupon receipt of the one or more transmissions via the network causes the second computing device to execute steps of i) accessing the pangenetic data associated with the user; ii) accessing a dataset (e.g., an item feedback matrix) containing item preferences of individuals who also share the at least one item preference associated with the user, wherein pangenetic data of the individuals are correlated with the item preferences; and iii) determining for each item preference, the quantity of matches between the pangenetic data correlated with that item preference and the pangenetic data associated with the user; and 2) a receiver for receiving from the network, based on the quantity of matches determined for each item preference, output comprising a listing of at least a portion of the item preferences to indicate recommended items for the user.

In one embodiment, a mobile computing device for online prediction of user satisfaction with an item comprises 1) a transmitter for sending, to a second computing device via a network, one or more transmissions of at least one item preference associated with a user and an authorization granting access to pangenetic data associated with the user, whereupon receipt of the one or more transmissions via the network causes the second computing device to execute steps of i) accessing pangenetic data associated with the user; ii) accessing a dataset (e.g., an item feedback matrix) containing one or more levels of satisfaction correlated with the at least one item preference, wherein pangenetic data are associated with the one or more levels of satisfaction; and iii) determining for each level of satisfaction, the quantity of matches between the pangenetic data associated with that level of satisfaction and the pangenetic data associated with the user; and 2) a receiver for receiving from the network, based on the quantity of matches determined for each level of satisfaction, output indicating a level of satisfaction the user is predicted to experience with respect to the at least one item preference.

In one or more of the embodiments of a mobile computing device as disclosed above, the receiver of the mobile computing device is also for receiving, from the second computing device via the network, an authorization request for access to the pangenetic data associated with the user, and wherein the transmitter of the mobile computing device is also for sending, to the second computing device via the network, an authorization granting access to the pangenetic data associated with the user.

Figure 17:
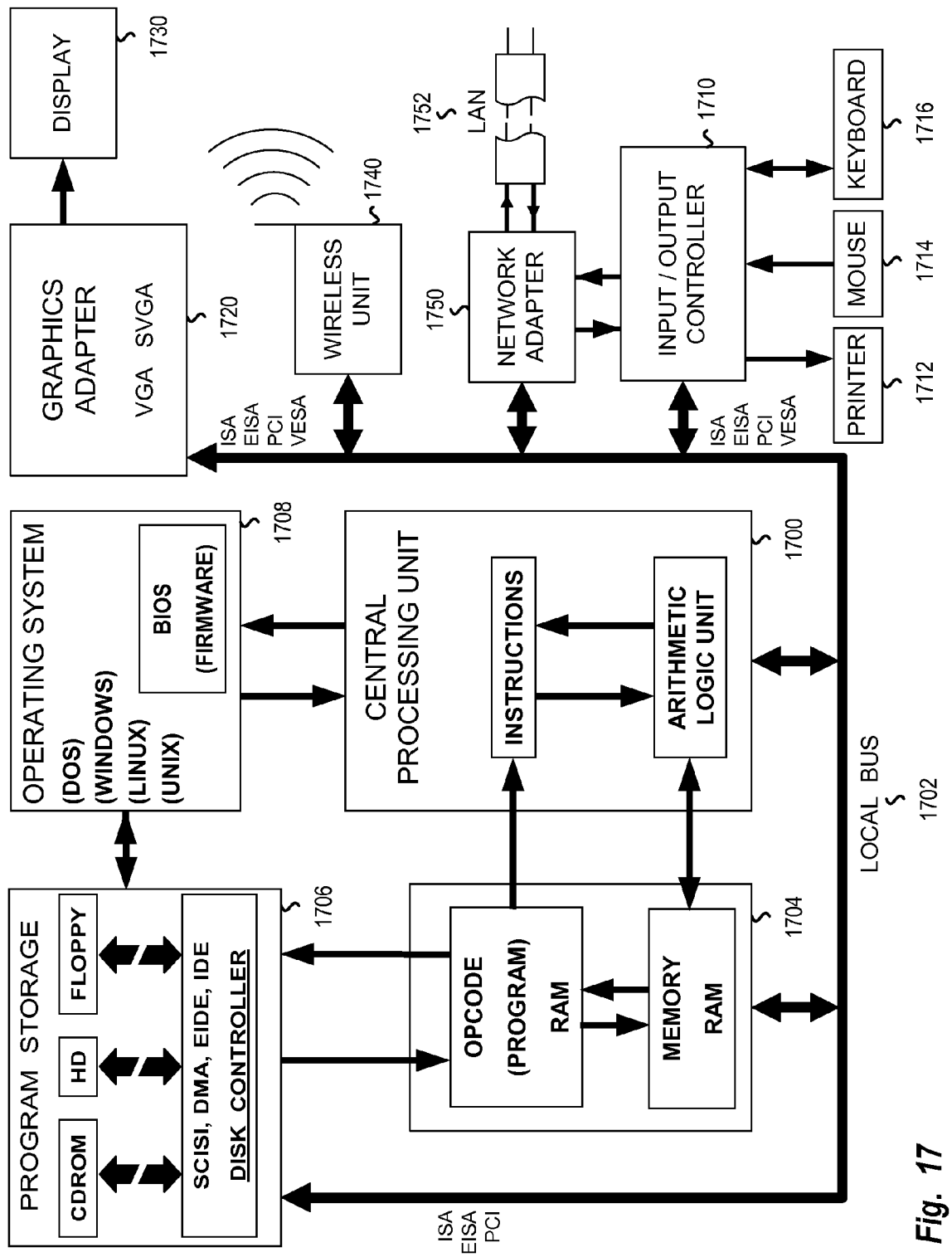
FIG. 17 illustrates a computing system on which the present method, software, database and system can be implemented.

FIG. 17 illustrates a representative computing system on which embodiments of the present method and system can be implemented. With respect to FIG. 17, a Central Processing Unit (CPU) 1700 is connected to a local bus 1702 which is also connected to Random Access Memory (RAM) 1704 and disk controller and storage system 1706. CPU 1700 is also connected to an operating system including BIOS 1708 which contains boot code and which can access disk controller and storage system 1706 to provide an operational environment and to run an application (e.g. service profiling or selection). The representative computing system includes a graphics adaptor 1720, display 1730, a wireless unit 1740 (i.e., a data receiver/transmitter device), a network adapter 1750 that can be connected to a LAN 1752 (Local Area Network), and an I/O controller 1710 that can be connected to a printer 1712, mouse 1714, and keyboard 1716.

It will be appreciated by one of skill in the art that the present methods, systems, software and databases can be implemented on a number of computing platforms, and that FIG. 17 is only a representative computing platform, and is not intended to limit the scope of the claimed invention. For example, multiprocessor units with multiple CPUs or cores can be used, as well as distributed computing platforms in which computations are made across a network by a plurality of computing units working in conjunction using a specified algorithm. The computing platforms may be fixed or portable, and data collection can be performed by one unit (e.g. a handheld unit) with the collected information being reported to a fixed workstation or database which is formed by a computer in conjunction with mass storage. Similarly, a number of programming languages can be used to implement the methods and to create the systems disclosed herein, those programming languages including but not limited to C, Java, php, C++, perl, visual basic, SQL and other languages which can be used to cause the representative computing system of FIG. 17 to perform the steps disclosed herein.

Figure 18:
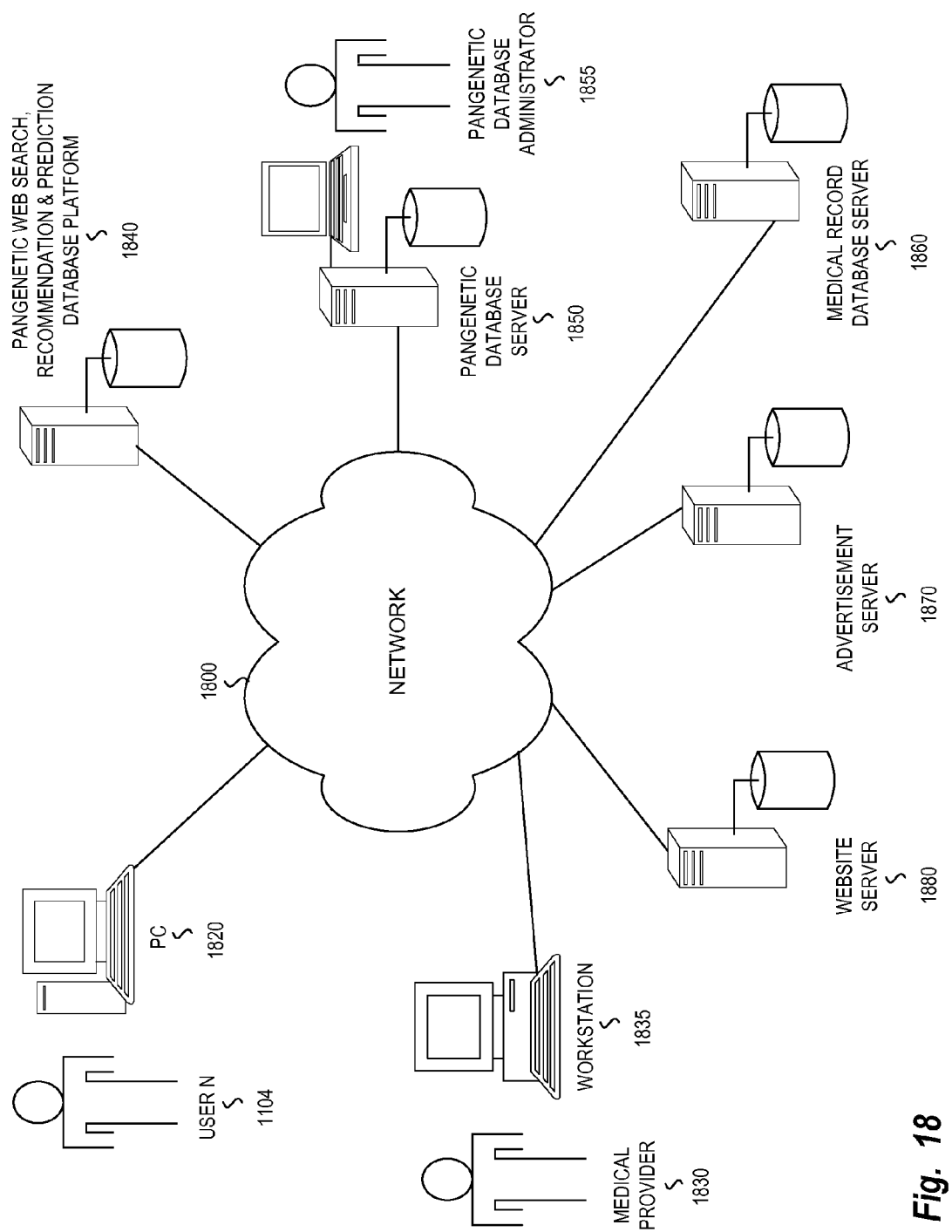
FIG. 18 illustrates a representative deployment diagram for a pangenetic based web search, recommendation and prediction database system.

FIG. 18. illustrates a representative deployment diagram for a pangenetic web search, recommendation and prediction database system. With respect to FIG. 18, the interconnection of various computing systems over a network 1800 to realize the pangenetic based systems of FIGS. 11 and 16, and the masked database transaction system of FIG. 9 is illustrated. In one embodiment, user N 1104 can use PC 1820 to interface with the system and more specifically to enter and receive data. Similarly, the medical provider 1830 can use workstation 1835 to interface with the system and to enter and receive data. Pangenetic database administrator 1855 uses an external pangenetic database server 1850 for the storage of pangenetic data, potentially in the form of pangenetic based Electronic Medical Records (EMRs), Electronic Health Records (EHRs), or Personal Health records (PHRs) for large populations. In one embodiment, the pangenetic database server 1850 is a medical record database server. In another embodiment, a dedicated medical record database server 1860 is connected to the system and provides pangenetic data for user by the system. User N 1104 can interact with pangenetic web search, recommendation and prediction database platform 1840 via network 1800 to request web searches, item recommendations and satisfaction predictions. Medical provider 1830 can similarly interact with pangenetic web search, recommendation and prediction database platform 1840 via network 1800 to request web searches, item recommendations and satisfaction/behavior predictions on behalf of themself and user N 1104. In one embodiment, workstation 1835 can provide the same functionality as pangenetic web search, recommendation and prediction database platform 1840. In one embodiment, workstation 1835 can provide the functionality provided by either pangenetic database server 1850 or medical record database server 1860. In one embodiment, pangenetic web search, recommendation and prediction database platform 1840 can provide the functionality provided by pangenetic database server 1850 or medical record database server 1860. In one embodiment, pangenetic database server 1850 can be the same as pangenetic database server 1614 of FIG. 16. In one embodiment, pangenetic web search, recommendation and prediction database platform 1840 can be the same as pangenetic web server 1604 of FIG. 16. In one embodiment, user N 1104 can use mobile device 1602 of FIG. 16 instead of PC 1820 to interface with the system. In one embodiment, medical provider 1830 can use a mobile computing device instead of workstation 1835 to interface with the system. Website server 1880 can be utilized to provide web item data and access to websites and webpages via network 1800 to the pangenetic web search, recommendation and prediction database platform 1840, as well as directly to user N 1104 and medical provider 1830. Advertisement server 1870 can provide dedicated advertisement items to be selected by pangenetic web search, recommendation and prediction database platform 1840 and displayed to user N 1104 and medical provider 1830, as depicted by the method illustrated in FIG. 15. All of the aforementioned computing systems are interconnected via network 1800.

As illustrated in an embodiment depicted by FIG. 18, a pangenetic web search, recommendation and prediction database platform 1840 can be utilized to host the software based components of pangenetic web search, recommendation and prediction database systems such as system 900 of FIG. 9, system 1100 of FIG. 11, and the system of FIG. 16, and data can be collected as illustrated in FIGS. 9-16. Once search results, recommendations and/or predictions are determined, they can be displayed to user N 1104 via PC 1820 and/or to medical provider 1830 via workstation 1835. In an alternate embodiment, the software-based components of the above pangenetic web search, recommendation and prediction database systems can reside on workstation 1835 operated by medical provider 1830 or on PC 1820 operated by user N 1104. In another embodiment, pangenetic database administrator 1855 can maintain and operate the above pangenetic web search, recommendation and prediction database systems and host their software-based components on pangenetic database server 1850. Another embodiment is also possible in which the above pangenetic web search, recommendation and prediction database systems are distributed across the various computing platforms. Similarly, other parties and hosting machines not illustrated in FIG. 18 may also be used to create the above pangenetic web search, recommendation and prediction database systems. All of the aforementioned computing systems can be interconnected via network 1800.

The methods, systems, software and databases described herein can also be implemented on one or more specialized computing platforms, those platforms having been customized to provide the capabilities described herein. The specialized computing platforms may have specialized operating systems, database tools, graphical user interfaces, communications facilities and other customized hardware and/or software which allow use for the specific application which could not be run on a general purpose computing platform.

Although the systems and methods described herein are frequently described in reference to one or more computers owned and operated by the actors in the system (e.g., users, a pangenetic database administrator), the determination of web search results, item recommendations and user related predictions can be achieved through use of distributed computing systems or cloud computing, wherein the actor requests an action through an interface (typically a webpage) and the determination is made using computing resources at one or more server farms, those resources obtaining the appropriate information (pangenetic data, non-pangenetic data) from a variety of sources, and combining that information to make the required calculations and determinations. When using a cloud computing system, the subsequent calculations may be performed at alternate locations.

Pangenetic information may be stored in a number of formats, on a variety of media, and in a centralized or distributed manner. In one embodiment, the data is stored in one location with a label associating that data with a particular user, and one or more indices marking or identifying segments of pangenetic data. In an alternate embodiment, the pangenetic data is stored at a plurality of locations with one or more identifiers or labels associating that information with a particular user. In this embodiment, secure communications protocols can be used to allow the system to access all necessary portions of the data and to compile the data in a way that allows the determination of correspondences and applicability to be made. For example, a website or web application may be authorized to compile certain segments of genetic or epigenetic sequences stored in one location with demographic or lifestyle information stored in another location to determine web items or recommendations that are most appropriate for a particular user. By collecting the relevant information from a plurality of sources, the system is able to construct an appropriate file for making the determination. In one embodiment, the datasets of the methods of the present invention may be combined into a single dataset. In another embodiment the datasets may be kept separated. Separate datasets may be stored on a single computing device or distributed across a plurality of devices. As such, a memory for storing such datasets, while referred to as a singular memory, may in reality be a distributed memory comprising a plurality of separate physical or virtual memory locations distributed over a plurality of devices such as over a computer network. Data, datasets, databases, methods and software of the present invention can be embodied on a computer-readable media (medium), computer-readable memory (including computer readable memory devices), and program storage devices readable by a machine.

In one embodiment, the datasets of the methods of the present invention may be combined into a single dataset. In another embodiment the datasets may be kept separated. Separate datasets may be stored on a single computing device or distributed across a plurality of devices. As such, a memory for storing such datasets, while referred to as a singular memory, may in reality be a distributed memory comprising a plurality of separate physical or virtual memory locations distributed over a plurality of devices such as over a computer network. Data, datasets, databases, methods and software of the present invention can be embodied on a computer-readable media (medium), computer-readable memory (including computer readable memory devices), and program storage devices readable by a machine.

In one embodiment, at least a portion of the data for one or more individuals is obtained from medical records, such as a Personal Health Record (PHR), Electronic Health Record (EHR) or Electronic Medical Record (EMR). In one embodiment, at least a portion of the data for one or more individuals is accessed, retrieved or obtained (directly or indirectly) from a centralized medical records database. In one embodiment, at least a portion of the data for one or more individuals is accessed or retrieved from a centralized medical records database over a computer network.

A number of interfaces can be used to support access by different users and other parties, including computer systems, requiring access to the system. In one embodiment an interface is presented over the web, using protocols such as http and https in combination with Hypertext Markup Language (HTML), Java, and other programming and data description/presentation tools which allow information to be presented to and received from the user or users. The interface may contain a number of active elements such as applets or other code which actively constructs display elements and which prompts the user for specific information and which actively creates queries or formulates or formats results for presentation, transmission (e.g. downloading), or storage. In one embodiment the interface allows users to sort data such that products, service and providers can be listed by a particular parameter or sets of parameters. For example, in one embodiment the user can request a presentation of most appropriate (highly matched) web items which are sub-ranked according to appropriateness for the age and/or gender of the user. In an alternate embodiment, a graphical presentation (map) is presented which indicates the most appropriate web items by color or icon. The interface can allow authorized queries to the different databases in the system, and within the constraints of the authorizations and permissions, make the determinations of applicability (appropriateness) of web items based on the pangenetic data of the user. In one embodiment, the user interface at one location (e.g. subscriber location) works in conjunction with a user interface in another location (e.g. medical provider, healthcare provider) to allow pangenetic data to be accessed for making a determination of appropriateness of a web based information or product/service offerings.

The embodiments of the present invention may be implemented with any combination of hardware and software. If implemented as a computer-implemented apparatus, the present invention is implemented using means for performing all of the steps and functions disclosed above.

The embodiments of the present invention can be included in an article of manufacture (e.g., one or more computer program products) having, for instance, computer useable (i.e., readable) media. The media has embodied therein, for instance, computer readable program code means for providing and facilitating the mechanisms of the present invention. The article of manufacture can be included as part of a computer system or sold separately.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of the present invention is not limited to the particular examples and implementations disclosed herein, but is intended to cover modifications within the spirit and scope thereof as defined by the appended claims and any and all equivalents thereof.

The invention claimed is:

1. A computer based method for online recommendation of items for a user, comprising:
   a) receiving at least one item preference associated with the user along with one or more non-pangenetic attributes associated with the user;
   b) accessing pangenetic data associated with the user wherein the pangenetic data associated with the user constitutes a pangenetic profile of the user, wherein said accessing step is in accord with a previously set user identification and authorization protocol whereby said pangenetic profile is associated with said user and is masked according to a predetermined data mask:
   c) accessing a dataset containing item preferences of individuals who also share the at least one item preference associated with the user, wherein pangenetic and non-pangenetic data of the individuals are correlated with the item preferences and wherein the pangenetic data correlated with the item preferences are combinations of pangenetic data selected from pangenetic profiles of the individuals, and further wherein the one or more non-pangenetic attributes associated with the user match one or more non-pangenetic attributes associated with the individuals, wherein the correlations between the pangenetic data and the item preferences contained in the dataset are previously determined based on statistical associations between item preferences and pangenetic data associated with the individuals;
   d) determining for each item preference, the quantity of matches between the pangenetic data associated with that item preference and the pangenetic data associated with the user; and
   e) transmitting as output, based on the quantity of matches determined for each item preference, a listing of at least a portion of the item preferences to indicate recommended items for the user wherein the portion of the item preferences transmitted as output is determined by a predetermined threshold applied to the quantity of matches determined for each item preference.

2. The computer based method of claim 1, wherein the transmitting in step (e) is to at least one destination selected from the group consisting of the user, a database, a dataset, a computer readable memory, a computer readable medium, a computer processor, a computer network, a printout device, a visual display, and a wireless receiver.

3. The computer based method of claim 1, further comprising transmitting as output at least a portion of the item preferences to indicate non-recommended items for the user.

4. The computer based method of claim 1, wherein the pangenetic data correlated with the item preferences are pangenetic metadata.

5. The computer based method of claim 1, wherein the item preferences are ratings that indicate levels of satisfaction with the items indicated by the item preferences.

6. The computer based method of claim 5, wherein the ratings are average ratings of the items by the individuals.

7. The computer based method of claim 1, further comprising the steps of i) transmitting an authorization request for access to the pangenetic data associated with the user, and ii) receiving an authorization granting access to the pangenetic data associated with the user.

8. The computer based method of claim 1, wherein the receiving in step (a) is from a mobile computing device, and wherein the transmitting in step (e) is to the mobile computing device.

9. The computer based method of claim 1, wherein the listing is a rank listing, and wherein the rank of each item preference in the rank listing is based on the quantity of matches determined for each item preference.

10. The computer based method of claim 9, wherein the portion of the item preferences transmitted as output consists of item preferences having a rank within a range defined by at least one predetermined threshold applied to rank.

11. The computer based method of claim 9, wherein the rank of each item preference represented in the rank listing is determined by a score computed for each item preference based on the quantity of matches determined for each item preference.

12. The computer based method of claim 11, wherein the score for each item preference is computed using a quantitative similarity measure applied to the pangenetic data.

13. The computer based method of claim 1, wherein the correlations between the pangenetic data and the item preferences contained in the dataset are determined by computing statistical associations between pangenetic data of individuals and online behaviors which indicate the item preferences of the individuals.

14. The computer based method of claim 1, wherein the dataset is an item feedback matrix.

15. The computer based method of claim 1, wherein the accessing in step (b) is in accordance with an applied data mask, the method further comprising: i) transmitting an authorization request for access to the pangenetic data associated with the user; ii) receiving an authorization which grants access to the pangenetic data; iii) accessing a data mask, wherein the data mask's parameters are associated with the authorization; and iv) applying the data mask to the pangenetic data.

16. The computer based method of claim 1, wherein the dataset comprises data records containing the item preferences of the individuals, the method further comprising:
   i) identifying one or more clusters of data records, wherein within each cluster the data records share a similar pattern of item preferences as determined by a quantitative similarity measure;
   ii) determining, by statistical association, pangenetic data that correlate with each of the one or more clusters; and
   iii) identifying, by using a quantitative similarity measure, the cluster having the highest pangenetic similarity to the user to provide the portion of the item preferences to be transmitted as output in step (e).

17. The computer based method of claim 16, wherein the item preferences of the identified cluster comprise item rating values that are averaged prior to transmission as output.

18. The computer based method of claim 16, wherein the item preferences identified for transmission as output are a subset of item preferences selected from the identified cluster based on an item category relationship with the at least one item preference associated with the user.

19. The computer based method of claim 1, wherein the dataset comprises data records containing the item preferences of the individuals, and wherein the item preferences comprise item rating values, the method further comprising:
   i) identifying one or more clusters of data records, wherein within each cluster the data records share a similar pattern of item preferences as determined by a quantitative similarity measure;
   ii) determining, by statistical association, pangenetic data that correlate with each of the one or more clusters;
   iii) identifying, by using a quantitative similarity measure, the cluster having the highest pangenetic similarity to the user; and
   iv) identifying, by using a quantitative similarity measure within the cluster having the highest pangenetic similarity to the user, a subcluster of data records having the most similar pattern of item preferences to the user to provide the portion of the item preferences to be transmitted as output in step (e).

20. The computer based method of claim 19, wherein the item preferences of the identified subcluster comprise item rating values that are averaged prior to transmission as output.

21. The computer based method of claim 1, further comprising receiving feedback from the user with respect to one or more of the item preferences contained in the listing transmitted as output.

22. A program storage device readable by a machine and containing a set of instructions which, when read by the machine, causes execution of a computer based method for online recommendation of items for a user, comprising:
   a) receiving at least one item preference associated with the user along with one or more non-pangenetic attributes associated with the user;
   b) accessing pangenetic data associated with the user wherein the pangenetic data associated with the user constitutes a pangenetic profile of the user, wherein said accessing step is in accord with a previously set user identification and authorization protocol whereby said pangenetic profile is associated with said user and is masked according to a predetermined data mask;
   c) accessing a dataset containing item preferences of individuals who also share the at least one item preference associated with the user, wherein pangenetic and non-pangenetic data of the individuals are correlated with the item preferences and wherein the pangenetic data correlated with the item preferences are combinations of pangenetic data selected from pangenetic profiles of the individuals, and further wherein the one or more non-pangenetic attributes associated with the user match one or more non-pangenetic attributes associated with the individuals, wherein the correlations between the pangenetic data and the item preferences contained in the dataset are previously determined based on statistical associations between item preferences and pangenetic data associated with the individuals;
   d) determining for each item preference, the quantity of matches between the pangenetic data correlated with that item preference and the pangenetic data associated with the user; and
   e) transmitting as output, based on the quantity of matches determined for each item preference, a listing of at least a portion of the item preferences to indicate recommended items for the user wherein the portion of the item preferences transmitted as output is determined by a predetermined threshold applied to the quantity of matches determined for each item preference.

23. The program storage device of claim 22, wherein the transmitting in step (e) is to at least one destination selected from the group consisting of the user, a database, a dataset, a computer readable memory, a computer readable medium, a computer processor, a computer network, a printout device, a visual display, and a wireless receiver.

24. A computer database system for online recommendation of items for a user, comprising:
   a) a memory containing:
      i) a first data structure containing pangenetic data associated with the user wherein the pangenetic data associated with the user constitutes a pangenetic profile of the user;
      ii) a second data structure containing item preferences of individuals who also share at least one item preference associated with the user, wherein pangenetic data and non-pangenetic of the individuals are correlated with the item preferences;
   b) a processor for:
      i) receiving the at least one item preference associated with the user along with one or more non-pangenetic attributes associated with said user;
      ii) accessing the first data structure, wherein said accessing step is in accord with a previously set user identification and authorization protocol whereby said pangenetic profile is associated with said user and is masked according to a predetermined data mask;
      iii) accessing the second data structure;
      iv) determining for each item preference, the quantity of matches between the pangenetic data correlated with that item preference and the pangenetic data associated with the user and wherein the pangenetic data correlated with the item preferences are combinations of pangenetic data selected from pangenetic profiles of the individuals, and further wherein the one or more non-pangenetic attributes associated with the user match one or more non-pangenetic attributes associated with the individuals, wherein the correlations between the pangenetic data and the item preferences contained in the dataset are previously determined based on statistical associations between item preferences and pangenetic data associated with the individuals; and
      v) transmitting as output, based on the quantity of matches determined for each item preference, a listing of at least a portion of the item preferences to indicate recommended items for the user wherein the portion of the item preferences transmitted as output in step is determined by a predetermined threshold applied to the quantity of matches determined for each item preference.

25. The computer database system of claim 24, wherein the transmitting in part (v) is to at least one destination selected from the group consisting of the user, a database, a dataset, a computer readable memory, a computer readable medium, a computer processor, a computer network, a printout device, a visual display, and a wireless receiver.

* * * * *

UNITED STATES PATENT AND TRADEMARK OFFICE
CERTIFICATE OF CORRECTION

| | | |
|---|---|---|
| PATENT NO. | : 8,386,519 B2 | Page 1 of 2 |
| APPLICATION NO. | : 12/346707 | |
| DATED | : February 26, 2013 | |
| INVENTOR(S) | : Kenedy et al. | |

It is certified that error appears in the above-identified patent and that said Letters Patent is hereby corrected as shown below:

On Title Page 2, in Item (56), under "U.S. PATENT DOCUMENTS",
in Column 1, Line 78, delete "Gessaman" and insert -- Geesaman --, therefor.

On Title Page 3, in Item (56), under "OTHER PUBLICATIONS", in Column 1, Line 26, delete "Genome Research. 2000 10: 950-958." and insert -- Genome Research. 2000 Jul;10(7): 950-958. --, therefor.

On Title Page 3, in Item (56), under "OTHER PUBLICATIONS", in Column 2, Line 17, delete "ECML/PKDD04" and insert -- ECML/PKDD '04 --, therefor.

On Title Page 3, in Item (56), under "OTHER PUBLICATIONS", in Column 2, Line 26, delete "Apr. 2006. 62" and insert -- Apr. 2006, 62 --, therefor.

On Title Page 3, in Item (56), under "OTHER PUBLICATIONS", in Column 2, Line 36, delete "Leveraing" and insert -- Leveraging --, therefor.

On Title Page 3, in Item (56), under "OTHER PUBLICATIONS", in Column 2, Line 37, delete "experiental" and insert -- experiential --, therefor.

On Title Page 3, in Item (56), under "OTHER PUBLICATIONS", in Column 2, Line 37, delete "Anautomated" and insert -- An automated --, therefor.

On Title Page 3, in Item (56), under "OTHER PUBLICATIONS", in Column 2, Line 39, delete "InformationJournal" and insert -- Information Journal --, therefor.

In the Specification

In Column 9, Line 23, delete "PageRank" and insert -- Page Rank --, therefor.

Signed and Sealed this
Fifth Day of November, 2013

Teresa Stanek Rea
*Deputy Director of the United States Patent and Trademark Office*

CERTIFICATE OF CORRECTION (continued)
U.S. Pat. No. 8,386,519 B2

In Column 29, Line 63, delete "an pangenetic profile, from an pangenetic" and insert -- a pangenetic profile, from a pangenetic --, therefor.

In Column 30, Line 61, delete "an pangenetic" and insert -- a pangenetic --, therefor.

In Column 37, Line 49, delete "904," and insert -- 906, --, therefor.

In Column 59, Line 38, delete "adaptor" and insert -- adapter --, therefor.

In Column 59, Line 63, delete "FIG. 18." and insert -- FIG.18 --, therefor.